United States Patent
Gentschev et al.

(10) Patent No.: US 7,335,629 B2
(45) Date of Patent: Feb. 26, 2008

(54) SUPPORT-FIXED BLEACHING CATALYST COMPLEX COMPOUNDS SUITABLE AS CATALYSTS FOR PEROXYGEN COMPOUNDS

(75) Inventors: Pavel Gentschev, Düsseldorf (DE); Steve Döring, Düsseldorf (DE); Jacques Breyer, Heusden-Destelbergen (BE); Antonio Machin, Barcelona (ES)

(73) Assignee: Henkel Kommanditgesellschaft Auf Aktien, Duesseldorf (DE)

( * ) Notice: Subject to any disclaimer, the term of this patent is extended or adjusted under 35 U.S.C. 154(b) by 188 days.

(21) Appl. No.: 10/873,071

(22) Filed: Jun. 21, 2004

(65) Prior Publication Data

US 2004/0266641 A1    Dec. 30, 2004

Related U.S. Application Data

(63) Continuation of application No. PCT/EP02/14290, filed on Dec. 16, 2002.

(30) Foreign Application Priority Data

Dec. 21, 2001 (DE) ................... 101 63 331

(51) Int. Cl.
C11D 1/00 (2006.01)
C11D 3/26 (2006.01)
C11D 3/37 (2006.01)
C11D 3/395 (2006.01)
C11D 7/54 (2006.01)

(52) U.S. Cl. ............. 510/311; 510/350; 510/351; 510/367; 510/372; 510/376; 510/475; 510/499; 510/500; 8/111; 540/465; 540/474

(58) Field of Classification Search ............. None
See application file for complete search history.

(56) References Cited

U.S. PATENT DOCUMENTS

| 3,234,258 A | | 2/1966 | Morris |
|---|---|---|---|
| 3,873,668 A | | 3/1975 | Melby |
| 4,104,466 A | | 8/1978 | Tsuchida et al. |
| 4,230,828 A | | 10/1980 | Gaul, Jr. et al. |
| 5,075,041 A | | 12/1991 | Lutz |
| 5,114,611 A | | 5/1992 | Van Kralingen et al. |
| 5,194,416 A | | 3/1993 | Jureller et al. |
| 5,560,748 A | * | 10/1996 | Surutzidis et al. ............ 8/111 |
| 5,580,485 A | | 12/1996 | Feringa et al. |
| 5,880,299 A | | 3/1999 | Ponsati Obiols et al. |
| 6,452,053 B2 | | 9/2002 | Fischer et al. |

FOREIGN PATENT DOCUMENTS

| DE | 26 45 079 A1 | 4/1978 |
|---|---|---|
| DE | 195 39 846 C1 | 11/1996 |
| DE | 100 19 878 A1 | 10/2001 |
| DE | 100 29 601 A1 | 12/2001 |
| EP | 0 544 490 A1 | 6/1993 |
| EP | 0 549 271 A1 | 6/1993 |
| EP | 0 392 592 B1 | 11/1994 |
| EP | 0 408 131 B1 | 5/1995 |
| EP | 0 384 503 B1 | 6/1995 |
| EP | 0 443 651 B1 | 10/1995 |
| EP | 0 458 397 B1 | 3/1997 |
| EP | 0 458 398 B1 | 3/1997 |
| EP | 0 909 809 A2 | 4/1999 |
| WO | WO 96/06157 A1 | 2/1996 |
| WO | WO 97/48710 A1 | 12/1997 |
| WO | WO 98/39405 A1 | 9/1998 |
| WO | WO 98/44162 A1 | 10/1998 |
| WO | WO 01/18166 A2 | 3/2001 |
| WO | WO 01/48138 A2 | 7/2001 |

OTHER PUBLICATIONS

Zhang et al; Catalytic oxidation over metalloporphyrin encapsulated in Nb-doped mesoporous silica, Book of Abstracts, 213th ACS National Meeting, San Francisco, Apr. 13-17, 1997, Coll-348.*
Tsuchida et al., "Polymer-Metal Complexes", Advances in Polymer Science, vol. 24, pp. 1-87, XP001146742 (1977).
K. Wieghardt, "Die aktiven Zentren in manganhaltigen Metalloproteinen und anorganische Modellkomplexe", Angew. Chem. vol. 101, pp. 1179-1198 (1995).
De Vos et al., "Heterogenization of Mn and Fe complex oxidation catalysts", Catalysis Today, vol. 57, pp. 105-114 (2000).

* cited by examiner

Primary Examiner—Gregory R. Del Cotto
(74) Attorney, Agent, or Firm—Woodcock Washburn LLP

(57) ABSTRACT

The present invention relates to support-fixed bleaching catalyst(s)suitable or the catalysis of peroxide compounds, characterized in that the support-fixed bleaching catalyst(s) is/are covalently bonded to a support by means of at least one organic ligand of the bleaching catalyst. The bleaching catalyst(s) form(s) a complex with at least on transition metal. The invention further relates to support-fixed bleaching catalysts for the catalysis of peroxide compounds, where at least one ligand, covalently bonded to a support, is a transition-metal-free ligand, which chelates with transition metal, derived from another source, preferably from the bleaching composition and/or added water and thus forms the complex with a transition metal.

29 Claims, No Drawings

SUPPORT-FIXED BLEACHING CATALYST COMPLEX COMPOUNDS SUITABLE AS CATALYSTS FOR PEROXYGEN COMPOUNDS

CROSS REFERENCE TO RELATED APPLICATIONS

This application is a continuation of PCT/EP02/14290, filed Dec. 16, 2002, which claims the benefit of De 101 63 331.9, filed Dec. 21, 2001, the complete disclosures of which are hereby incorporated by reference in their entirety.

FIELD OF INVENTION

The present invention relates to support-fixed bleaching catalyst complex compounds, to compositions comprising support-fixed bleaching catalyst complex compounds and to the use of support-fixed complex compounds as bleaching catalysts. The invention relates in particular to support-fixed bleaching catalyst complex compounds of transition metals having nitrogen-containing polydentate ligands as catalysts for peroxygen compounds, preferably suitable for the bleaching of color stains during the laundering of textiles and the cleaning of hard surfaces, those of tableware, for example, and also to detergents, cleaning products and disinfectants which comprise these catalysts.

BACKGROUND

Inorganic peroxygen compounds, especially hydrogen peroxide and solid peroxygen compounds which dissolve in water to release hydrogen peroxide, such as sodium perborate and sodium carbonate perhydrate, have long been used as oxidizing agents for purposes of disinfection and bleaching. The oxidizing action of these substances in dilute solutions is heavily dependent on the temperature; for instance, with $H_2O_2$ or perborate in alkaline bleaching liquors, sufficiently rapid bleaching of soiled textiles is obtained only at temperatures above about 80° C. At lower temperatures the oxidizing action of the inorganic peroxygen compounds can be enhanced by adding what are called bleach activators, for which numerous proposals have been disclosed in the literature, principally from the classes of the N-acyl or O-acyl compounds, examples being polyacylated alkylenediamines, especially tetraacetylethylenediamine, acylated glycolurils, especially tetraacetylglycoluril, N-acylated hydantoins, hydrazides, triazoles, hydrotriazines, urazoles, diketopiperazines, sulfurylamides and cyanurates, and also carboxylic anhydrides, especially phthalic anhydride, carboxylic esters, especially sodium nonanoyloxybenzenesulfonate, sodium isononanoyloxybenzenesulfonate and acylated sugar derivatives, such as pentaacetylglucose. By addition of these substances the bleaching action of aqueous peroxide liquors can be increased to such an extent that even at temperatures around 60° C. essentially the same activities occur as with the peroxide liquor alone at 95° C.

Given the concern for energy-saving laundering and bleaching methods, in recent years application temperatures well below 60° C. have gained in importance, in particular below 45° C. down to the cold water temperature, below 20° C.

The prior art has disclosed the use of transition metal salts and transition metal complexes, as proposed for example in European patent applications EP 392 592, EP 443 651, EP 458 397, EP 544 490, EP 549 271 and WO 01/48138, referred to as bleaching catalysts.

It has now been observed that textiles, particularly coloreds, fade after a number of washes. Without wishing to be bound to any particular theory, it is supposed that the catalysts used in the prior art not only catalyze the peroxygen compounds but also directly contact the surfaces to be bleached, such as textile surfaces, and remain at least partly on their surfaces even when the cleaning operation has ended. The transition metal salts containing in the complex compounds are washed out in detectable amounts during the washing operation, and these transition metal salts can then be oxidized and so cause color damage, since they directly contact the article to be bleached: textiles, for example. Mn(II), for example, is demonstrably oxidized to manganese dioxide, $MnO_2$. Manganese dioxide is a not unhazardous oxidizing agent which is very strong, particularly toward readily oxidizable substances, such as organic dye compounds. In the case of the transition metal salts which have been washed out there is a risk, presumably owing to the high reactivity of the oxidizing intermediates formed from them and the peroxygen compounds, of fiber damage and/or color change in colored textiles and, in extreme cases, the risk of oxidative damage to the textiles.

All of the bleaching catalysts known in the art have the disadvantage that they can contact the surfaces of the articles to be bleached to an increased extent, may adhere to those surfaces and may even penetrate the surfaces of the articles to be bleached—for example, they may penetrate into the depth of the textile—so that there is an increased risk of unwanted color changes and in rare cases, with textiles, there may even be holes, as a result of fiber damage.

SUMMARY

It is an object of the present invention to provide bleaching catalysts which overcome above disadvantages in the state of the art. In particular it is an object of the present invention to provide complex compounds free of transition metal salt and/or complex compounds containing transition metal salts which are suitable as bleaching catalysts and which significantly prevent the risk of unwanted color changes and/or fiber damage as compared with the prior art or which even prevent said risk.

Yet another object of the present invention is to provide complex compounds free from transition metal salt and/or complex compounds containing transition metal salt which are suitable as bleaching catalysts and which catalyze the oxidizing action and bleaching action of inorganic peroxygen compounds at low temperatures, below 80° C., in particular in the temperature range from about 15° C. to 45° C.

It is an object of the present invention to overcome the disadvantages in the state of the art and also to improve the bleaching catalyst properties and additionally to lower the amount of peroxide required while maintaining the same bleaching performance.

DETAILED DESCRIPTION

It has now surprisingly been found that the bleaching catalyst complexes more fixed or covalently bonded on at least one support via at least one organic ligand overcome the aforementioned disadvantages of the state of the art. In particular it has been found that the amount of peroxide used can be reduced to bring about the same bleaching action as in comparison to the same bleaching catalyst complexes not bonded on a support. It has surprisingly been found that bleaching catalyst complexes of the invention, fixed or covalently bonded on at least one support via at least one organic ligand and containing transition metal, in particular having nitrogen-containing polydentate ligands, also possess an improved action in catalyzing bleaching.

The effect of the polymeric support is advantageously to prevent accumulation of the catalyst in the fabric. In particular the supports are selected such that the catalyst is in a solid form or heterogeneous catalysis can take place. Known disadvantages of heterogeneous catalysis, such as the phase change of substrate and catalyst, do not apply here, since the catalysis of activated bleaching-active peroxygen compounds does not have to take place directly at the site of staining. The half-life of customary peroxygen compounds (e.g., peracetic acid) is generally sufficiently high that the peroxygen compounds are able to reach the site of staining (the site of action) via diffusion. A further advantage of the support-fixed catalysts is the ability for the catalysts to be used again and the readiness with which the catalyst material can be separated off. Reference is given in particular to those supports (preferably of flexible, polymeric materials) which are suitable for use, for example, in a washing machine.

The object of the invention is achieved by means of a support-fixed bleaching catalyst(s) suitable for catalyzing peroxide compounds, the support-fixed bleaching catalyst or catalysts being bonded covalently to a support via at least one organic ligand of the bleaching catalyst, and the bleaching catalyst or catalysts forming a complex with at least one transition metal. By covalent bonding is meant here, preferably, those chemical bonds which are not cleaved in aqueous solutions, and in particular are not cleaved in acid-containing or base-containing solutions. In particular the covalent bond between bleaching catalyst and support will not be opened under typical wash conditions (basic, pH>9, >60 min, aqueous surfactant solution, temperature>30° C.) or else acidic conditions (e.g., pH 3). Examples of particularly suitable compounds which are both acid-stable and base-stable include secondary and tertiary amines, C—C linkages or ether bonds. (R—H$_2$C—N$_{(tert.)}$—R$_2$, (R—H$_2$C—NH$_{(sec.)}$—R, R—H$_2$C—CH$_2$—R bonds or R—H$_2$C—O—CH$_2$—R— (ether bonds).

It has been found that even free ligands which are covalent on a support can be used which forms the transition metal complex only at the site of use, with a transition metal originating from a different source: for example, from the bleach composition and/or from the water used.

The object of the invention is hence also achieved by means of a support-fixed bleaching catalyst(s) for the catalysis of peroxide compounds, where one ligand covalently bonded on a support is a transition-metal-free ligand which chelates with a transition metal originating from another source, preferably from the bleach composition and/or added water, and so forms the transition metal complex.

It has additionally been found that the support-fixed bleaching catalyst is suitable for activating peroxygen compounds and/or oxygen. Accordingly it is also possible to use peroxygen-free compositions if sufficient amounts of oxygen are available at the site of use.

In the context of this invention one or more transition metal complexes may be attached via one or more ligands to at least one support. It is self-evident that not only the ligands which can be used in accordance with the invention but also the complexes can be identical or different.

The term "optional" as used in the description embraces all conceivable variations. Compounds and groups which are substituted "optionally" therefore embrace unsubstituted and substituted compounds and groups, respectively, for the purposes of this invention.

For the purposes of this invention the terms "alkyl, alkoxy, aryl, alkenyl, alkylene, arylene, amines, halogen, carboxylated derivatives, cycloalkyl, carbonyl derivatives, C1-C6 heterocycloalkyl, heterocycloalkyl, heteroaryl, heteroarylene, sulfonate, sulfate, phosphonate, phosphate, phosphine, phosphine oxide", unless specified otherwise, are as follows:

Alkyl=linear or branched C1-C8 alkyl.
Alkenyl=C2-C6 alkenyl.
Cycloalkyl=C3-C8 cycloalkyl.
Alkoxy=C1-C6 alkoxy.
Aryl=homoaromatics having a molecular weight of $\leq 300$.

Alkylene=methylene; 1,1-ethylene; 1,2-ethylene; 1,1-propylidene; 1,2-propylene; 1,3-propylene, 2,2-propylidene; butan-2-ol-1,4-diyl; propan-2-ol-1,3-diyl; 1,4-butylene; cyclohexane-1,1-diyl; cyclohexane-1,2-diyl; cyclohexane-1,3-diyl; cyclohexane-1,4-diyl; cyclopentane-1,1-diyl; cyclopentane-1,2-diyl; and/or cyclopentane-1,3-diyl. Arylene=1,2-phenylene; 1,3-phenylene; 1,4-phenylene; 1,2-naphthylene; 1,3-naphthylene; 1,4-naphthylene, 2,3-naphthylene; 1-hydroxy-2,3-phenylene; 1-hydroxy-2,4-phenylene; 1-hydroxy-2,5-phenylene; and/or/or 1-hydroxy-2,6-phenylene.

Heteroaryl=pyridinyl; pyrimidinyl; pyrazinyl; triazolyl; pyridazinyl; 1,3,5-triazinyl; quinolinyl. Isoquinolinyl; quinoxalinyl; imidazolyl; pyrazolyl; benzimidazolyl; thiazolyl; oxazolidinyl; pyrrolyl; carbazolyl; indolyl; and/or isoindolyl, in which the heteroaryl is connected to the compound via a ring atom of the respective heteroaryl radical.

Heteroarylene=pyridinediyl; quinolinediyl; pyrazodiyl; pyrazolediyl; triazolediyl; pyrazinediyl; and/or imidazolediyl, in which the heteroarylene bridges the compound via an atom of the chosen heteroarylene; particular preference is given to pyridine-2,3-diyl; pyridine-2,4-diyl; pyridine-2,5-diyl; pyridine-2,6-diyl; pyridine-3,4-diyl; pyridine-3,5-diyl; quinoline-2,3-diyl; quinoline-2,4-diyl; quinoline-2,8-diyl; isoquinoline-1,3-diyl; isoquinoline-1,4-diyl; pyrazole-1,3-diyl; pyrazole-3,5-diyl; triazole-3,5-diyl; triazole-1,3-diyl; pyrazine-2,5-diyl; and/or imidazole-2,4-diyl.

C1-C6 heterocycloalkyl=piperidinyl; piperidine; 1,4-piperazine, tetrahydrothiophene; tetrahydrofuran; 1,4,7-triazacyclononane; 1,4,8,11-tetraazacyclotetradecane; 1,4,7,10,13-pentaazacyclopentadecane; 1,4-diaza-7-thiacyclononane; 1,4-diaza-7-oxacyclononane; 1,4,7,10-tetraazacyclododecane; 1,4-dioxane; 1,4,7-trithiaacyclononane; pyrrolidine; and/or tetrahydropyran, in which the heterocycloalkyl can be joined to the —C1-C6 alkyl via a ring atom of the chosen heterocycloalkyl.

Heterocycloalkylene=piperidin-1,2-ylene; piperidin-2,6-ylene; piperidin-4,4-ylidene; 1,4-piperazin-1,4-ylene; 1,4-piperazin-2,3-ylene; 1,4-piperazin-2,5-ylene; 1,4-piperazin-2,6-ylene; 1,4-piperazin-1,2-ylene; 1,4-piperazin-1,3-ylene; 1,4-piperazin-1,4-ylene; tetrahydrothiophen-2,5-ylene; tetrahydrothiophen-3,4-ylene; tetrahydrothiophen-2,3-ylene; tetrahydrofuran-2,5-ylene; tetrahydrofuran-3,4-ylene; tetrahydrofuran-2,3-ylene; pyrrolidin-2,5-ylene; pyrrolidin-3,4-ylene; pyrrolidin-2,3-ylene; pyrrolidin-1,2-ylene; pyrrolidin-1,3-ylene; pyrrolidin-2,2-ylene; 1,4,7-triazacyclonon-1,4-ylene; 1,4,7-triazacyclonon-2,3-ylene; 1,4,7-triazacyclonon-2,9-ylene; 1,4,7-triazacyclonon-3,8-ylene; 1,4,7-triazacyclonon-2,2-ylidene; 1,4,8,11-tetraazacyclotetradec-1,4-ylene; 1,4,8,11-tetraazacyclotetradec-1,8-ylene; 1,4,8,11-tetraazacyclotetradec-2,3-ylene; 1,4,8,11-tetraazacyclotetradec-2,5-ylene; 1,4,8,11-tetraazacyclotetradec-1,2-ylene; 1,4,8,11-tetraazacyclotetradec-2,2-ylidene; 1,4,7,10-tetraazacyclododec-1,4-ylene; 1,4,7,10-tetraazacyclododec- 1,7-ylene; 1,4,7,10-tetraazacyclododec-1,2-ylene; 1,4,7,10-tetraazacyclododec-2,3-ylene; 1,4,7,10-tetraazacyclododec-2,2-ylidene; 1,4,7,10,13-pentaazacyclopentadec-1,4-ylene; 1,4,7,10,13-pentaazacyclopentadec-1,7-ylene; 1,4,7,10,13-pentaazacyclopentadec-2,3-ylene; 1,4,7,10,13-pentaazacyclopentadec-1,2-ylene; 1,4,7,10,13-pentaazacyclopentadec-2,2-ylidene; 1,4-diaza-7-thiacyclonon-1,4-ylene; 1,4-diaza-7-thiacyclonon-1,2-ylene; 1,4-diaza-7-thiacyclonon-2,3-ylene; 1,4-diaza-7-thiacyclonon-6,8-ylene; 1,4-diaza-7-thiacyclonon-2,2-ylidene; 1,4-diaza-7-oxacyclonon-1,4-ylene; 1,4-diaza-7-oxacyclonon-1,2-ylene; 1,4-diaza-7-oxacyclonon-2,3-ylene; 1,4-diaza-7-oxacyclonon-6,8-ylene; 1,4-diaza-7-oxacyclonon-2,2-ylidene; 1,4-dioxan-2,3-ylene; 1,4-dioxan-2,6-ylene; 1,4-dioxan-2,2-ylidene; tetrahydropyran-2,3-ylene; tetrahydropyran-2,6-ylene; tetrahydropyran-2,5-ylene; tetrahydropyran-2,2-ylidene; 1,4,7-trithiacyclonon-2,3-ylene; 1,4,7-trithiacyclonon-2,9-ylene; and/or 1,4,7-trithiacyclonon-2,2-ylidene.

Heterocycloalkyl=pyrrolinyl; pyrrolidinyl; morpholinyl; piperidinyl; piperazinyl; hexamethylenimine; 1,4-piperazinyl; tetrahydrothiophenyl; tetrahydrofuranyl; 1,4,7-triazacyclononanyl; 1,4,8,11-tetraazacyclotetradecanyl; 1,4,7,10,13-pentaazacyclopentadecanyl; 1,4-diaza-7-thiacyclononanyl; 1,4-diaza-7-oxacyclononanyl; 1,4,7,10-tetraazacyclododecanyl; 1,4-dioxanyl; 1,4,7-trithiacyclononanyl; tetrahydropyranyl; and/or oxazolidinyl, the heterocycloalkyl being connected to the compound via a ring atom of the respective heterocycloalkyl.

Amine=—N(R)2 in which each R independently of the other is selected from the group consisting of: H; C1-C6 alkyl; C1-C6 alkyl-C6H5; and/or phenyl, it being possible for the two Rs to form an —NC3 to —NC5 heterocyclic ring closure.

Halogen=F; Cl; Br and/or I.

Sulfonate=—S(O)2OR, in which R=H; C1-C6 alkyl; phenyl; C1-C6 alkyl-C6H5; Li; Na; K; Cs; Mg; and/or Ca.

Sulfate=—OS(O)2OR, in which R=H; C1-C6 alkyl; phenyl; C1-C6 alkyl-C6H5; Li; Na; K; Cs; Mg; and/or Ca.

Sulfone: —S(O)2R, in which R=H; C1-C6 alkyl; phenyl; C1-C6 alkyl-C6H5 and/or amine (to form sulfonamide) is selected from the group consisting of: —NR'2, in which each R' independently of the other is selected from the group consisting of: H; C1-C6 alkyl; C1-C6 alkyl-C6H5; and/or phenyl, in which if both R's=C1-C6 alkyl the R's may together form an —NC3 to —NC5 heterocyclic ring closure.

Carboxylate derivatives=—C(O)OR, in which R is selected from the group consisting of: H; C1-C6 alkyl; phenyl; C1-C6 alkyl-C6H5; Li; Na; K; Cs; Mg; and/or Ca.

Carbonyl derivatives=—C(O)R, in which R is selected from the group consisting of: H; C1-C6 alkyl; phenyl; C1-C6 alkyl-C6H5 and/or amine (to form amide) is selected from the group consisting of: —NR'2, in which R' independently at each occurrence is selected from the group consisting of: H; C1-C6 alkyl; C1-C6 alkyl-C6H5; and/or phenyl, in which if both R's=C1-C6 alkyl the R's together may form an —NC3 to —NC5 heterocyclic ring closure.

Phosphonate=—P(O)(OR)2, in which each R independently of the other is selected from the group consisting of: H; C1-C6 alkyl; phenyl; C1-C6 alkyl-C6H5; Li; Na; K; Cs; Mg; and/or Ca.

Phosphate=—OP(O)(OR)2, in which each R independently of the other is selected from the group consisting of: H; C1-C6 alkyl; phenyl; C1-C6 alkyl-C6H5; Li; Na; K; Cs; Mg; and/or Ca.

Phosphine=—P(R)2, in which each R independently of the other is selected from the group consisting of: H; C1-C6 alkyl; phenyl; C1-C6 alkyl-C6H5.

Phosphine oxide=—P(O)R2, in which each R independently of the other is selected from the group consisting of: H; C1-C6 alkyl; phenyl; C1-C6 alkyl-C6H5 and/or amine (to form phosphonamidate) is selected from the group consisting of: —NR'2, in which R' independently at each occurrence is selected from the group consisting of: H; C1-C6 alkyl; C1-C6 alkyl-C6H5; and/or phenyl, in which if both R's=C1-C6 alkyl the R's may together form an —NC3 to —NC5 heterocyclic ring closure.

Particular preference, unless specified otherwise, is given to the following:

alkyl=linear and/or branched C1-C6 alkyl;
alkenyl=C3-C6 alkenyl;
cycloalkyl: C6-C8 cycloalkyl;
alkoxy=C1-C4 alkoxy;
alkylene=selected from the group consisting of: methylene; 1,2-ethylene; 1,3-propylene; butan-2-ol-1,4-diyl; 1,4-butylene; cyclohexane-1,1-diyl; cyclohexane-1,2-diyl; cyclohexane-1,4-diyl; cyclopentane-1,1-diyl; and/or cyclopentane-1,2-diyl;
aryl=selected from the group consisting of: phenyl; biphenyl; naphthyl; anthracenyl; and/or phenanthrenyl;
arylene=selected from the group consisting of: 1,2-phenylene; 1,3-phenylene; 1,4-phenylene; 1,2-naphthylene; 1,4-naphthylene; 2,3-naphthylene and/or 1-hydroxy-2,6-phenylene;
heteroaryl=selected from the group consisting of: pyridinyl; pyrimidinyl; quinolinyl; pyrazolyl; triazolyl; isoquinolinyl; imidazolyl; and/or oxazolidinyl, in which the heteroaryl is attached to the compound via a ring atom of the chosen heteroaryl;
heteroarylene=selected from the group consisting of: pyridine-2,3-diyl; pyridine-2,4-diyl; pyridine-2,6-diyl; pyridine-3,5-diyl; quinolin-2,3-diyl; quinolin-2,4-diyl; isoquinolin-1,3-diyl; isoquinolin-1,4-diyl; pyrazole-3,5-diyl; and/or imidazole-2,4-diyl;
heterocycloalkyl=selected from the group consisting of: pyrrolidinyl; morpholinyl; piperidinyl; piperidinyl; 1,4-piperazinyl; tetrahydrofuranyl; 1,4,7-triazacyclononanyl; 1,4,8,11-tetraazacyclotetradecanyl; 1,4,7,10,13-pentaazacyclopentadecanyl; 1,4,7,10-tetra-azacyclododecanyl; and/or piperazinyl; in which the heterocycloalkyl is linked to the compound via a ring atom of the chosen heterocycloalkyl;
heterocycloalkylene=selected from the group consisting of: piperidin-2,6-ylene; piperidin-4,4-ylidene; 1,4-piperazin-1,4-ylene; 1,4-piperazin-2,3-ylene; 1,4-piperazin-2,6-ylene; tetrahydrothiophen-2,5-ylene; tetrahydrothiophen-3,4-ylene; tetrahydrofuran-2,5-ylene; tetrahydrofuran-3,4-ylene; pyrrolidin-2,5-ylene; pyrrolidin-2,2-ylidene; 1,4,7-triazacyclonon-1,4-ylene, 1,4,7-triazacyclonon-2,3-ylene; 1,4,7-triazacyclonon-2,2-ylidene; 1,4,8,11-tetraazacyclotetradec-1,4-ylene; 1,4,8,11-tetraazacyclotetradec-1,8-ylene; 1,4,8,11-tetraazacyclotetradec-2,3-ylene; 1,4,8,11-tetraazacyclotetradec-2,2-ylidene; 1,4,7,10-tetraazacyclododec-1,4-ylene; 1,4,7,10-tetraazacyclododec-1,7-ylene; 1,4,7,10-tetraazacyclododec-2,3-ylene; 1,4,7,10-tetraazacyclododec-2,2-ylidene; 1,4,7,10,13-pentaazacyclopentadec-1,4-ylene; 1,4,7,10,13-pentaazacyclopentadec-1,7-ylene; 1,4-diaza-7-thiacyclonon-1,4-ylene; 1,4-diaza-7-thiacyclonon-2,3-ylene; 1,4-diaza-7-thiacyclonon-2,2-ylidene; 1,4-diaza-7-oxacyclonon-1,4-ylene; 1,4-diaza-7-oxacyclonon-2,3-ylene; 1,4-diaza-7-oxacyclonon-2,2-ylidene; 1,4-dioxan-2,6-ylene; 1,4-dioxan-2,2-ylidene; tetrahydropyran-2,6- ylene; tetrahydropyran-2,5-ylene; and/or tetrahydropyran-2,2-ylidene;

C1-C6 alkyl-heterocycloalkyl, in which the heterocycloalkyl of the —C1-C6 heterocycloalkyl is selected from the group consisting of: piperidinyl; 1,4-piperazinyl; tetrahydrofuranyl; 1,4,7-triazacyclononanyl; 1,4,8,11-tetraazacyclotetradecanyl; 1,4,7,10,13-pentaazacyclopentadecanyl; 1,4,7,10-tetraazacyclododecanyl; and/or pyrrolidinyl, the heterocycloalkyl being linked to the —C1-C6 alkyl via a ring atom of the respective heterocycloalkyl;

amine=—N(R)2, in which each R independently of the other is selected from the group consisting of: H; C1-C6 alkyl; and/or benzyl;

halogen=selected from the group consisting of: F and/or Cl;

sulfonate=—S(O)2OR, in which R is selected from the group consisting of: H; C1-C6 alkyl; Na; K; Mg; and/or Ca;

sulfate=—OS(O)2OR, in which R is selected from the group consisting of: H; C1-C6 alkyl; Na; K; Mg; and/or Ca;

sulfone=—S(O)2R, in which R is selected from the group consisting of: H; C1-C6 alkyl; benzyl and/or amine is selected from the group consisting of: —NR'2, in which each R' independently of the other is selected from the group consisting of: hydrogen; C1-C6 alkyl; and/or benzyl;

carboxylate derivative=—C(O)OR; in which R is selected from the group consisting of: H; Na; K; Mg; Ca; C1-C6 alkyl; and/or benzyl.

carbonyl derivative=C(O)R; in which R is selected from the group consisting of: H; C1-C6 alkyl; benzyl and/or amine is selected from the group consisting of: —NR'2, in which each R' independently of the other is selected from the group consisting of: hydrogen; C1-C6 alkyl; and/or benzyl;

phosphonate=—P(O)(OR)2; in which each R independently of the other is selected from the group consisting of: H; C1-C6 alkyl; benzyl; Na; K; Mg; and/or Ca;

phosphate=—OP(O)(OR)2; in which each R independently of the other is selected from the group consisting of: H; C1-C6 alkyl; benzyl; Na; K; Mg; and/or Ca;

phosphines=—P(R)2; in which each R independently of the other is selected from the group consisting of: H; C1-C6 alkyl; and/or benzyl;

phosphine oxide=—P(O)R2; in which each R independently of the other is selected from the group consisting of: H; C1-C6 alkyl; benzyl and/or amine is selected from the group consisting of: —NR'2, in which each R' independently of the other is selected from the group consisting of: hydrogen; C1-C6 alkyl; and/or benzyl.

Suitable support material in principle comprises shaped articles, such as powders, particles, films, gels and textile fibers.

Supports for the purposes of this invention, to which at least one ligand of at least one bleaching catalyst may be covalently bonded, embrace polymers, preferably selected from the group consisting of polyvinyl chloride, polybutadiene, polychlorobutadiene, polyvinylidene chloride, polyacrylonitrile, polydichloromethyloxaisobutane, polyurethane, polystyrenes, polymethacrylates, polyvinyl alcohols, polyethylenimines, cellulose, chitosan, polysiloxanes, polyamides, polyamines, polyformaldehydes, polyethylene, polypropylene, polytetrafluoroethylene, polyisobutylene, polydimethylphenylene oxide, chloromethylated polystyrene and/or polyisocyanates, with chloromethylated polystyrene being the most preferred.

Suitable as support material in principle are shaped articles made from thermoplastics such as polypropylene (PP), polyethylene (PE), polyamides (PA) and/or polyesters.

The supports which can be used in accordance with the invention have a molecular weight of ≧100, ≧500, ≧1000, preferably ≧10 000, more preferably ≧50 000, more preferably still ≧100 000. It is also possible, however, to use supports having molecular weights of ≧1 000 000 and ≧10 000 000.

One support may have linked to it more than one bleaching catalyst bonded covalently to the support via at least one ligand. Preferably there are more than 2 ligands, more preferably more than 10 and more preferably still more than 20 ligands covalently attached to the support. Depending on the support, however, it is also possible for there to be more than 50, in particular more than 100 or else more than 500 covalently fixed ligands. Also possible are even more than 1000 or even more than 10 000, if the support material has a sufficiently high molecular weight. The ligands bonded to the support may also be free ligands; that is, these ligands do not exhibit any transition metal. In such cases the transition metal originates from other sources, such as the wash liquor, rinsing liquor or the like.

By textile fibers are meant all fibers which can be processed in textile fashion.

Textile fibers can be classified according to origin or material nature into the following groups:

1. Natural fibers: in the case of these fibers a distinction is made between fibers of plant, animal and mineral origin. The plant fibers which come from fiber-bearing plants are subdivided further into a) seed fibers, e.g., cotton, capok, b) bast fibers, e.g., flax, hemp, jute, kenaf, ramie, rosella, sunn, urena, c) hard fibers, e.g., alfa grass or esparto grass, fique, henequen, coir, manila, phormium, sisal. Animal fibers are divided into the following subgroups: a) wool, b) fine animal hairs, e.g., angora, alpaca, guanaco, camel, rabbit, cashmere, lama, mohair, vicuña, yak, c) coarse animal hairs, e.g., cattle hair and horse hair, goat hair, and d) silks, e.g., mulberry silk and tussah silk.

2. Manufactured fibers: these fibers, formerly called synthetic fibers, can be grouped into fibers of natural and synthetic polymers and fibers of inorganic substances.
a) Modified natural substances are generally of plant origin. They include in particular fibers of regenerated cellulose, such as cuprammonium silk, viscose fibers, modal fibers and cellulose acetates, such as acetate, triacetate, fibers of alginates, such as alginate fibers and polyisoprenes, such as rubber. Fibers of regenerated cellulose, and occasionally those of cellulose esters too, are often referred to in this context as artificial silk or rayon.
b) By synthetic fibers are meant fully synthetic manufactured fibers which are produced from simple organic building blocks (monomers) by means of polymerization reactions—that is, addition polymerization, polycondensation or polyaddition. The synthetic fibers include for example the elasto fibers, such as elastane, elastodiene; fluoro fibers; polyacrylic fibers, such as polyacrylonitrile, modacryl; polyamide fibers, such as nylon, aramid; polychloride fibers, such as polyvinyl chloride, polyvinylidene chloride; polyester fibers; polyolefin fibers, such as polyethylene, polypropylene and polyvinyl alcohol fibers. c) Inorganic chemical fibers may be of glass, carbon or metal. To produce fibers, they are brought into a spinable form and in that state, for example in solution or as a melt, are pressed through narrow apertures, nozzles for example, into a solidifying medium, e.g., a precipitation bath in the case of the wet spinning process or a heated spinning shaft in the case of the dry spinning process, and/or are formed into filaments in melt spinning apparatus, optionally drawn, colored, spun to fibers by various methods and united to form yarns.

It is possible in principle to use not only woven but also nonwoven materials, such as nonwoven webs, wovens or knits of the abovementioned materials or other suitable materials or mixtures thereof. As materials or as supports it is also possible to use materials such as foams, especially open-pored foams, microfibers, nanofibers, particles, agglomerates and/or films, among others; the particles, nanoparticles, agglomerates, powders and/or gels may be formed from the same material as the fibers. The supports may be composed in particular of one specific material or of mixtures of materials.

The particles suitable as supports preferably have a particle diameter of 20 μm and 1 mm and preferably between 200 μm ad 0.6 mm.

The organic ligand or ligands of the present invention, bonded covalently to the support material, are suitable for forming a bleaching catalyst complex by complexing a metal, the complex formed being suitable for the catalysis of bleaches, particularly peroxy compounds. The bleaching catalyst complex covalently bonded to a support with at least one ligand preferably comprises a transition metal.

In a further embodiment the ligand covalently bonded to a support by at least one ligand is a free ligand which forms the transition-metal-comprising complex only at the site of use with the transition metal, which originates from another source: for example, from the bleaching composition and/or from the water used. This transition metal complex is preferably formed in situ in the application medium.

The bleaching catalyst complex which can be used in accordance with the invention and is covalently bonded to a support by at least one ligand, preferably an organic ligand, comprises at least one transition metal.

The transition metal or metals are preferably selected from the group consisting of: Mn in oxidation states II-V, Fe I-IV, Cu I-III, Co I-III, Ni I-III, Cr II-VII, Ag I-II, Ti II-IV, W IV-VI, Pd II, Ru II-V, V II-V and/or Mo II-VI.

The support-fixed bleaching catalyst can be regenerated at a pH of between 7-14, preferably 8-10 and more preferably $\geq 9.5$.

In accordance with the invention it is possible with preference to use support-fixed complexes with transition metals, such as manganese, iron, cobalt, ruthenium, molybdenum, titanium, vanadium and/or copper. Ligands which are able to form a covalent bond with a support have the following general formula I,

in which R is a direct bond or an unsubstituted or amino-substituted alkylene group having 1 to 4 carbon atoms, A is a fused or nonfused ring system containing at least one nitrogen atom, and B is hydrogen, an OH group or A.

Complexes of this kind which are support-fixed via such (a) ligand(s) can be used as catalysts, particularly for inorganic peroxygen compounds in oxidizing, washing, cleaning or disinfecting solutions. In the alkylene groups R it is possible for one or more nonadjacent CH₂ units not attached directly to the central nitrogen atom to have been replaced, if desired, by NH units.

Covalent fixing of compounds of the general formula I to polymeric supports poses a particular synthesis challenge, since in contrast to other ligand systems (macrocyclic systems, for example) it is necessary first to introduce appropriate anchor groups.

Compounds of the general formula I can be converted by formal linking modification of their B units into ligands of the general formula II

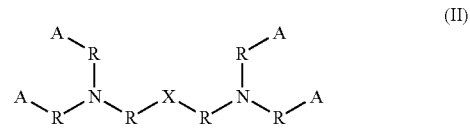

in which A and R are as defined above and X is an optionally hydroxy- and/or $C_{1-4}$ alkyl-substituted phenylene ring or an optionally hydroxy-substituted $C_{1-4}$ alkylene group, and which may be able to effect complex binding of two transition metal atoms in each case. The invention hence further provides for the use of optionally two- or more-centered complexes, which are covalently support-fixed via at least one ligand, of the transition metals manganese, iron, cobalt, ruthenium, molybdenum, titanium, vanadium and/or copper, which comprise one or more of the ligands of the general formula II. Complexes of the invention which are support-fixed in this way can be used as catalysts in particular for inorganic peroxygen compounds in oxidizing, washing, cleaning or disinfecting solutions.

In the R—B moiety of the compounds of formula I R is preferably a direct bond if B is hydrogen and is preferably not a direct bond if B is a hydroxyl group. It is not necessary for all the groups R in one ligand molecule to be identical. The preferred nitrogen-containing ring systems (A in formulae I and II) include the 2-pyridyl group, the 2-imidazolyl group, the 1-methyl-2-imidazolyl group and the 2-benzimidazolyl group. It is not necessary for all of the radicals A in one ligand molecule to be identical. R in the compounds of the formulae I or II is preferably a methylene group. X in the compounds of formula II is preferably selected from among the 1,3-phenylene group, the 2-hydroxy-1,3-phenylene group, the 2-hydroxy-5-methyl-1,3-phenylene group and the hydroxymethylene group.

Ligands of the general formulae I or II can be prepared by methods which are known in principle, as described for example in the review article by K. Wieghardt in Angew. Chem. 101 (1995), pp. 1179-1198 and the original papers cited therein. Normally, raw materials available commercially are reacted by condensation reactions, with elimination of halogenated hydrocarbons, for example, to form the desired ligands. These ligands can be reacted subsequently with salts of corresponding transition metals, normally in common solvents. The complexes for use as bleaching catalysts in accordance with the invention are generally formed even at room temperature and are normally obtained in crystalline form from common solvents.

The stated transition metals in the bleaching catalysts for use in accordance with the invention are preferably in oxidation states +2, +3 or +4. Preference is given to using complexes containing central transition metal atoms in oxidation states +3 or +4. Systems with mixed oxidation numbers are possible. In the case of multi-centered complexes it is not necessary for all of the metal atoms in the complex to be the same. The complexes used with preference include those with iron and/or manganese as central atoms.

Besides the ligands of the general formula I and II, the transition metal complexes for use in accordance with the invention may carry further ligands, generally ligands of simpler construction, especially monovalent or polyvalent anion ligands. Suitable examples include nitrate, acetate, formate, citrate, perchlorate and the halides such as chloride, bromide and iodide, and also complex anions such as hexafluorophosphate. The anion ligands ensure charge compensation between the central transition metal atom and the ligand system. Also possible is the presence of oxo ligands, peroxo ligands and imino ligands. These additional ligands may also have a bridging effect, leading to multi-centered complexes containing at least one ligand of the general formulae I or II.

The ligand or ligands can be support-fixed via reactive groups such as OH, N, H, halogen, multiple bonds, especially double bonds or the like, to at least one reactive group of the support, thereby forming a covalent bond. Single covalent bonds between support and ligand can be achieved, for example, via N atom of the ligand, by means of quaternization. The formation of multiple and/or single bonds between ligand(s) and support embrace substitution reactions and/or condensation reactions. Between the support and the ligand it is possible for an ester bond or else an ether bond to be formed. In principle all single and multiple bonds between support and ligand are possible provided the ligand remains capable of coordination. It is preferred for the support polymer to contain at least one functional group and/or substituent suitable for forming a covalent bond, preferably selected from the group consisting of —H, —OH, —NH$_2$, —NH—R, -halogen, —SH, —Si—OR, —C═C, —C≡C, —OR, —NCO, —COOH, —COOR, —CHO, —CN, —NH—C═O, —O═C—O—C═O and/or epoxide.

The preferred ligands which can be covalently bonded to a support for the purpose of forming bleaching catalysts in accordance with the invention include those comprising the: tris(2-pyridylmethyl)amine ligand,

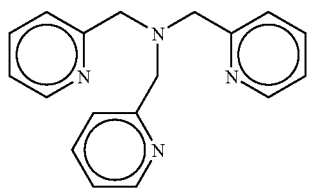

comprising the (bis((1-methylimidazol-2-yl)methyl))(2-pyridylmethyl) amine ligand,

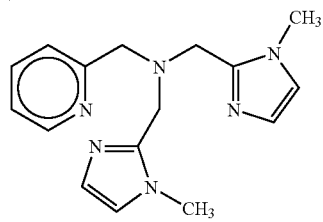

comprising the N-bis(2-benzimodazolylmethyl)aminoethanol ligand,

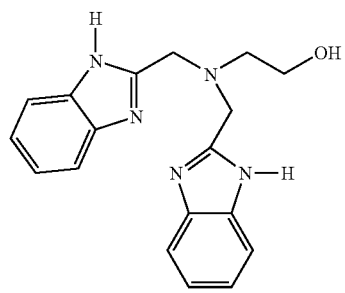

and comprising the N,N'- (bis(1-methylimidazol-2-yl)methyl)ethylenediamine ligand,

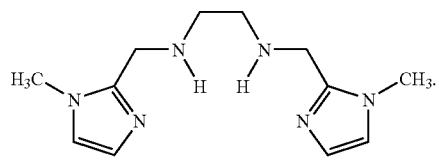

The preferred ligands of general formula II include 2,6-bis(bis(2-benzimidazolylmethyl)aminomethyl)-4-methylphenol,

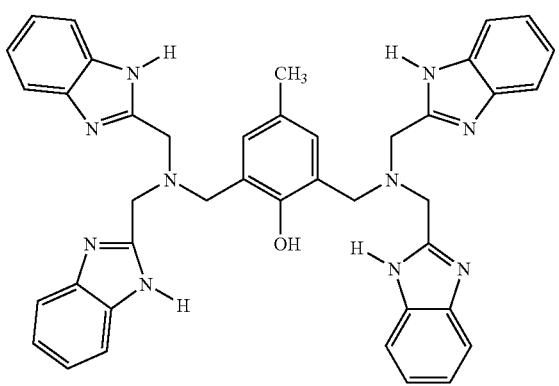

N,N,N',N'-tetrakis-(2-benzimidazolylmethyl)-2-hydroxy-1,3-diaminopropane,

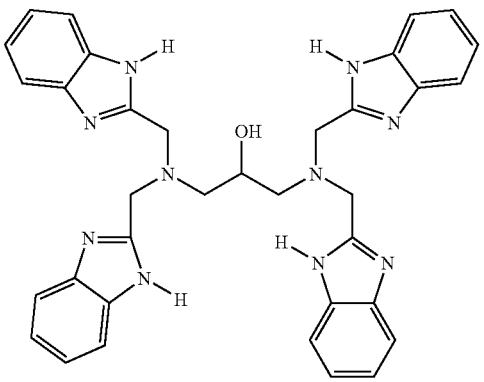

1,3-bis(bis(2-benzimidazolylmethyl)aminomethyl)benzene,

-continued

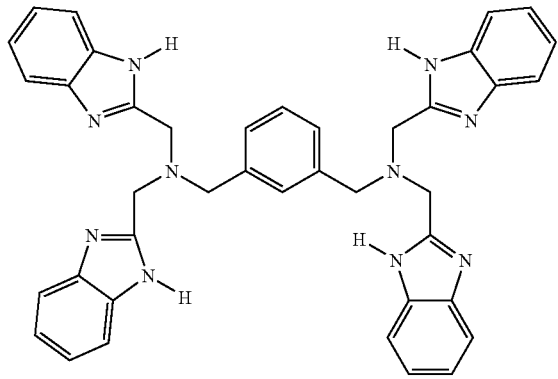

and 2,6-bis(bis(2-pyridylmethyl)aminomethyl)-4-methylphenol,

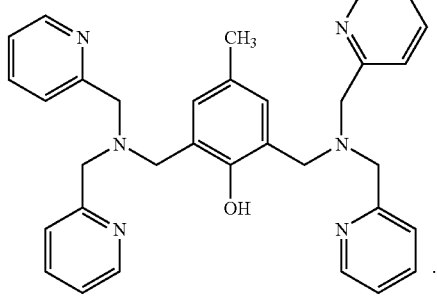

A support-fixed transition metal bleaching catalyst having the ligands of formula I or formula II which can be bonded covalently to a support is used preferably for bleaching colored stains, such as color stains when laundering textiles, particularly in an aqueous liquor containing surfactant. The formulation "bleaching of color stains" is to be understood in its widest sense and embraces not only the bleaching of dirt present on the textile and the bleaching of dirt detached from the textile and present in the wash liquor but also the oxidative destruction of textile colors present in the wash liquor, which detach from textiles under the washing conditions, before they can attach to different-colored textiles.

A further preferred form of application in accordance with the invention is the inventive use of the support-fixed transition metal bleaching catalysts, comprising the ligands of formula I particular for tableware, for bleaching colored stains. In this context as well the concept of bleaching is understood to embrace not only the bleaching of dirt present on the hard surface but also the bleaching of dirt detached from the hard surface and present in the dishwash liquor.

Dipodal ligands which can be used with preference in accordance with the invention and where the covalent bond to the support, a Merrifield resin for example, can be formed via the central secondary amine of the ligand are depicted below:

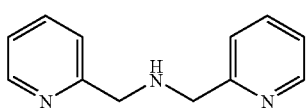

bis(2-pyridylmethyl)amine

-continued

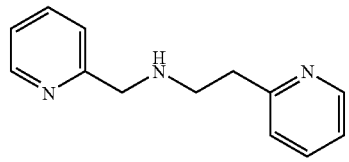

(2-pyridylmethyl)(2-(2-pyridyl)ethyl)amine

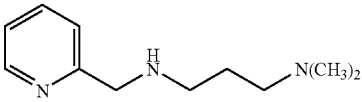

(2-pyridylmethyl)(3-(N,N-dimethylamino)propyl)amine

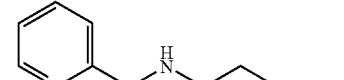

(2-pyridylmethyl)(2-(N,N-dimethylamino)ethyl)amine

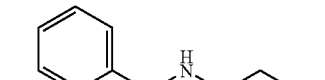

(2-pyridylmethyl)(2-hydroxyethyl)amine

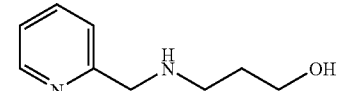

(2-pyridylmethyl)(3-hydroxypropyl)amine

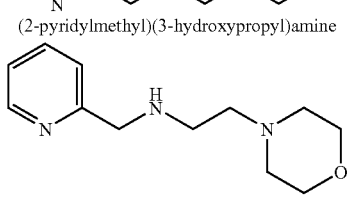

(2-pyridylmethyl)(2-N-morpholinoethyl)amine

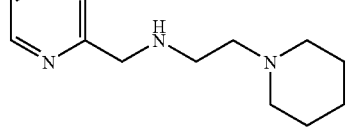

(2-pyridylmethyl)(2-N-piperidinoethyl)amine

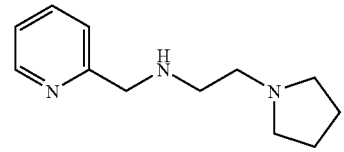

(2-pyridylmethyl)(2-N-pyrrolidinoethyl)amine

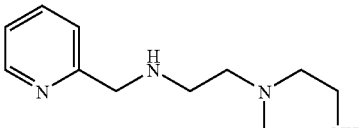

(2-pyridylmethyl)(2-N-piperazinoethyl)amine

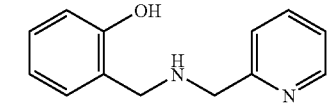

(2-hydroxybenzyl)(2-pyridylmethyl)amine

-continued

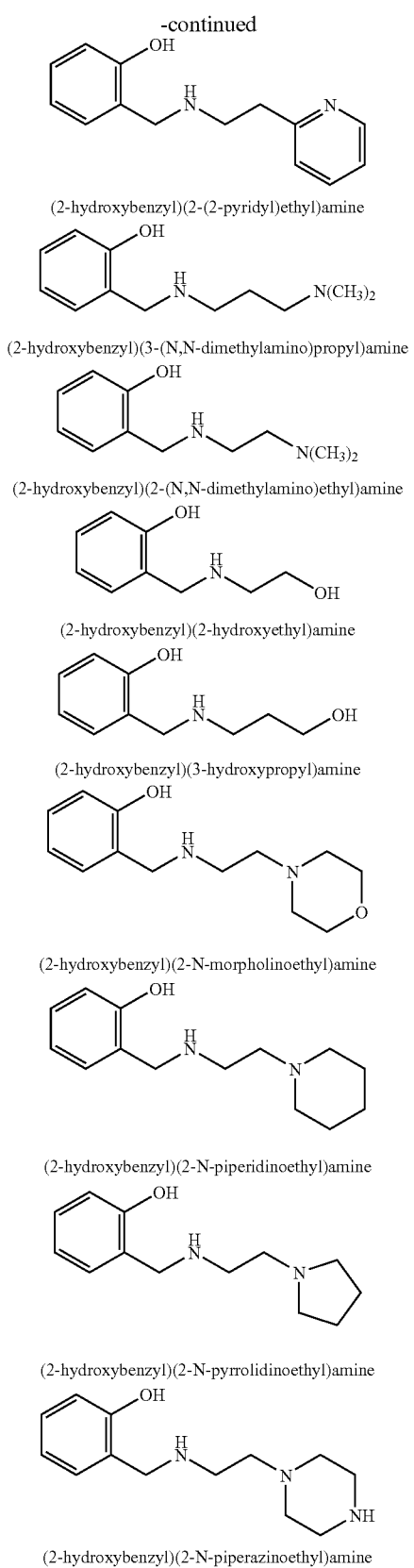

(2-hydroxybenzyl)(2-(2-pyridyl)ethyl)amine (2-hydroxybenzyl)(3-(N,N-dimethylamino)propyl)amine (2-hydroxybenzyl)(2-(N,N-dimethylamino)ethyl)amine (2-hydroxybenzyl)(2-hydroxyethyl)amine (2-hydroxybenzyl)(3-hydroxypropyl)amine (2-hydroxybenzyl)(2-N-morpholinoethyl)amine (2-hydroxybenzyl)(2-N-piperidinoethyl)amine (2-hydroxybenzyl)(2-N-pyrrolidinoethyl)amine (2-hydroxybenzyl)(2-N-piperazinoethyl)amine Listed below are tripodal ligands which can be used with particular preference in accordance with the invention, where the covalent bond between the support, a Merrifield resin for example, and the tripodal ligands below can be formed preferably via the methyl group in position 6 of the tripodal ligand:

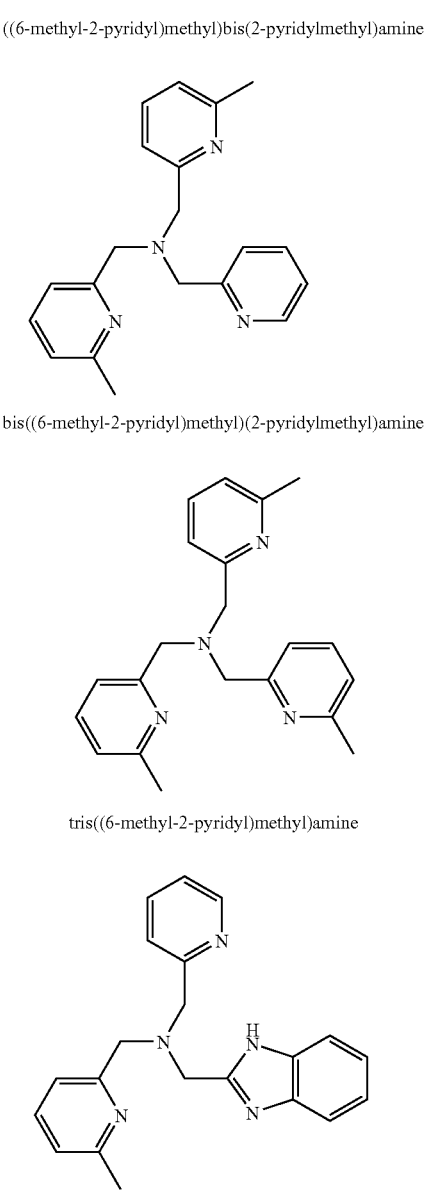

((6-methyl-2-pyridyl)methyl)bis(2-pyridylmethyl)amine bis((6-methyl-2-pyridyl)methyl)(2-pyridylmethyl)amine tris((6-methyl-2-pyridyl)methyl)amine

[(benzimidazol-2-yl)methyl][(6-methyl-2-pyridyl)methyl](2-pyridyl)methyl]amine

-continued

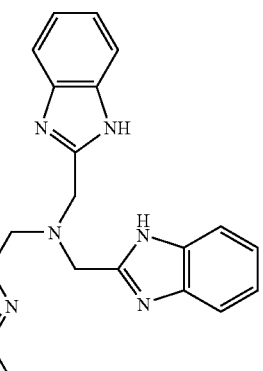

bis[(benzimidazol-2-yl)methyl][(6-methyl-2-pyridyl)methyl)]amine

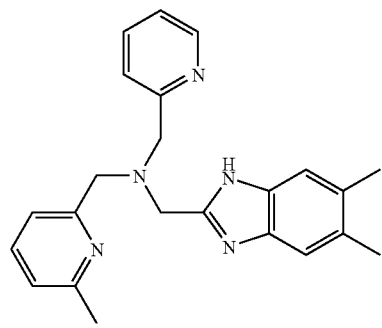

[(5,6-dimethylbenzimidazol-2-yl)methyl][(6-methyl-2-pyridyl)methyl)(2-pyridyl)methyl]amine

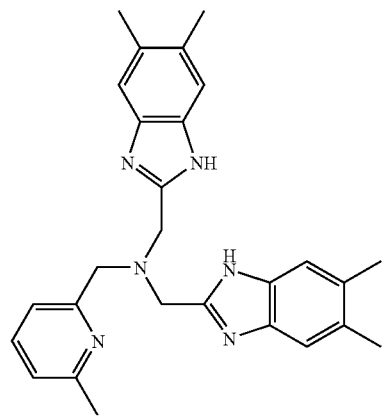

bis[(5,6-dimethylbenzimidazol-2-yl)methyl][(6-methyl-2-pyridyl)methyl)]amine

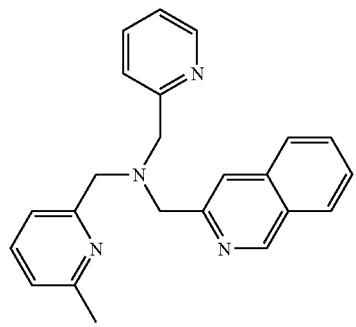

[(2-pyridyl)methyl(6-methyl-2-pyridyl)(2-quinolyl)methyl]amine

-continued

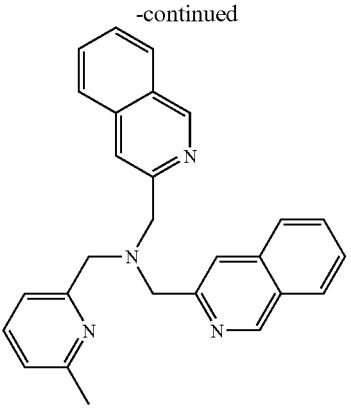

bis[(2-quinolyl)(6-methyl-2-pyridyl)methyl]amine

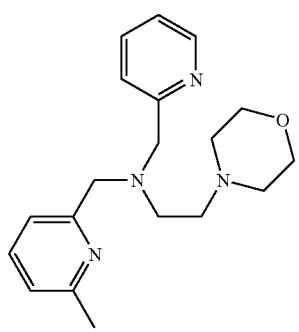

[(2-pyridyl)methyl](2-N-morpholinoethyl)][(6-methyl-2-pyridyl)methyl]amine

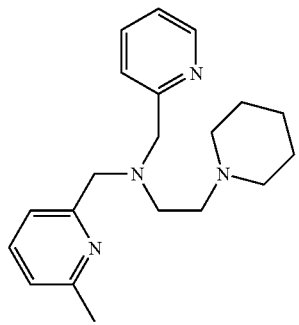

[(2-pyridyl)methyl](2-N-piperidinoethyl)][(6-methyl-2-pyridyl)methyl]amine

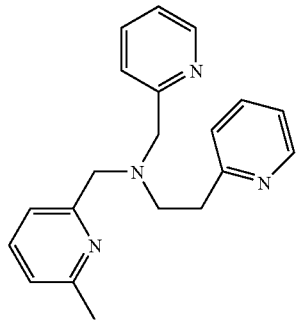

pmap[2-(2-pyridyl)ethyl][2-pyridyl)methyl)][(6-methyl-2-pyridyl)methyl]amine

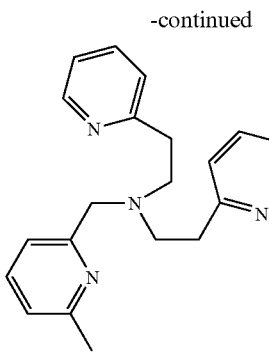

pmea[(2-pyridyl)methyl][2-(2-pyridyl)ethyl)][(6-methyl-2-pyridyl)methyl]amine

Heptadentate ligands which can be used with preference in accordance with the invention and where the covalent bond to the support, a Merrifield resin for example, can be formed via the central OH group of the ligand are depicted below:

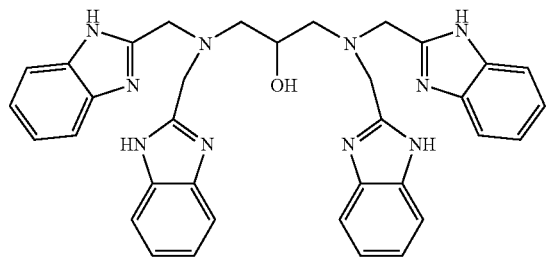

N,N,N',N'-tetrakis[2-benzimidazolylmethyl]-1,3-diamino-2-propanol

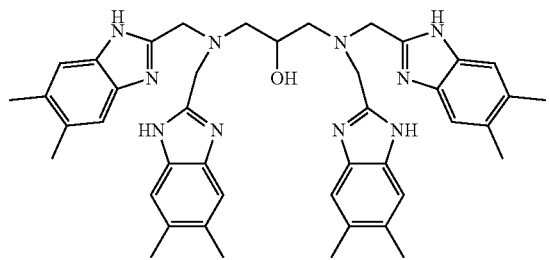

N,N,N',N'-tetrakis[2-(5,6-dimethyl)benzimidazolylmethyl]-1,3-diamino-2-propanol

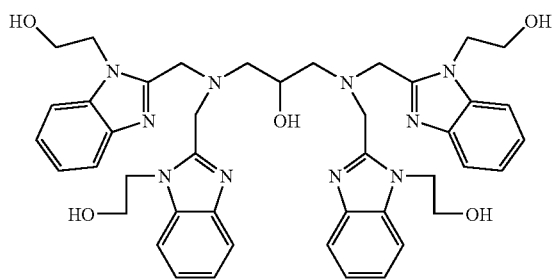

N,N,N',N'-tetrakis[2-(2-hydroxyethyl)benzimidazolylmethyl]-1,3-diamino-2-propanol

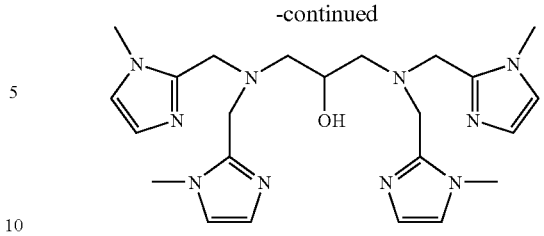

N,N,N',N'-tetrakis[2-(1-methyl)imidazolylmethyl]-1,3-diamino-2-propanol

Further bleaching catalyst complex(es) which can be used with preference in accordance with the invention and can be covalently bonded to a support with at least one organic ligand have the following general formula (A1):

$$[M_aL_kX_n]Y_m$$

in which:

M is a metal selected from the following group: Mn(II)-(III)-(IV)-(V), Cu(I)-(II)-(III), Fe(I)-(II)-(III)-(IV), Co(I)-(II)-(III), Ni(I)-(II)-(III), Cr(II)-(III)-(IV)-(V)-(VI)-(VII), Ti(II)-(III)-(IV), V(II)-(III)-(IV)-(V), Mo(II)-(III)-(IV)-(V)-(VI), W(IV)-(V)-(VI), Pd(II), Ru(II)-(III)-(IV)-(V) and/or Ag(I)-(II); preferably Mn(II)-(III)-(IV)-(V), Cu(I)-(II), Fe(II)-(III)-(IV) and/or Co(I)-(II)-(III);

L is a ligand listed in the description which if desired may have been protonated or deprotonated;

X is a molecule capable of coordination and/or a group comprising mono-, bi- or tri-charged anions and/or any desired neutral molecule suitable for the mono-, bi- or tridentate coordination of a metal, such as $O^{2-}$, $RBO_2^{2-}$, $RCOO^-$, $RCONR^-$, $OH^-$, $NO_3^-$, $NO_2^-$, NO, CO, $S^{2-}$, $RS^-$, $PO_4^{3-}$, $PO_3OR^{3-}$, $H_2O$, $CO_3^{2-}$, $HCO^{3-}$, ROH, NRR'R'', RCN, $Cl^-$, $Br^-$, $OCN^-$, $SCN^-$, $CN^-$, $N3^-$, $F^-$, $I^-$, $RO^-$, $ClO_4^-$, $SO_4^{2-}$, $HSO_4^-$, $SO_3^{2-}$ and/or $RSO_3^-$, and with particular preference $O^{2-}$, $RBO_2^{2-}$, $RCOO^-$, $OH^-$, $NO_3^-$, $NO_2^-$, NO, CO, $CN^-$, $S^{2-}$, $RS^-$, $PO_4^{3-}$, $H_2O$, $CO_3^{2-}$, $HCO^{3-}$, ROH, NRR'R'', RCN, $Cl^-$, $Br^-$, $OCN^-$, $SCN^-$, $N3^-$, $F^-$, $I^-$, $RO^-$, $ClO_4^-$, $SO_4^{2-}$, $HSO_4^-$, $SO_3^{2-}$ and/or $RSO_3^-$, and more preferably still $CF_3SO_3^-$;

Y is a noncoordinating counterion, preferably selected from the group consisting of $ClO_4^-$, $BR_4^-$, $[FeCl_4]^-$, $PF_6^-$, $RCOO^-$, $NO_3^-$, $NO_2^-$, $RO^-$, $N^+RR'R''R'''$, $Cl^-$, $Br^-$, $F^-$, $I^-$, $RSO_3^-$, $S_2O_6^{2-}$, $OCN^-$, $SCN^-$, $Li^+$, $Ba^{2+}$, $Na^+$, $Mg^{2+}$, $K^+$, $Ca^{2+}$, $Cs^+$, $PR_4^+$, $RBO_2^{2-}$, $SO_4^{2-}$, $HSO_4^-$, $SO_3^{2-}$, $SbCl_6^-$, $CuCl_4^{2-}$, $CN$, $PO_4^{3-}$, $HPO_4^{2-}$, $H_2PO_4^-$, $CO_3^{2-}$, $HCO_3^-$ and/or $BF_4^-$ and more preferably still $ClO_4^-$, $BR_4^-$, $[FeCl_4]^-$, $PF_6^-$, $RCOO^-$, $NO_3^-$, $NO_2^-$, $RO^-$, $N^+RR'R''R'''$, $Cl^-$, $Br^-$, $F^-$, $I^-$, $RSO_3^-$, $CF_3SO_3^-$, $S_2O_6^{2-}$, $OCN^-$, $SCN^-$, $Li^+$, $Ba^{2+}$, $Na^+$, $Mg^{2+}$, $K^+$, $Ca^{2+}$, $PR_4^+$, $SO_4^{2-}$, $HSO_4^-$, $SO_3^{2-}$ and/or $BF_4^-$;

R, R', R'' and R''' are independently of one another —H, —OH, —OR (in which R=alkyl, alkenyl cycloalkyl, heterocycloalkyl, aryl, heteroaryl or carbonyl group), —OAr, alkyl, alkenyl cycloalkyl, heterocycloalkyl, aryl, heteroaryl and/or carbonyl group, each R, Ar, alkyl, alkenyl, cycloalkyl, heterocycloalkyl, aryl, heteroaryl and/or carbonyl group can optionally be substituted by at least one group E or R6 together with R7 and/or independently thereof R8 together with R9 are O, in which E stands for functional groups comprising O, S, P, N, Se, halogen and/or any desired electron donor and/or withdrawing groups; and R, R', R" and R'" are preferably H, substituted alkyl or substituted aryl, more preferably H or substituted phenyl, naphthyl or C1-4 alkyl;

a is an integer of between 1 to 10, preferably 1 to 4;
k is an integer of between 1 to 10;
n=0 or is an integer of between 1 to 10, preferably 1 to 4;
m=0 or is an integer of between 1 to 20, preferably 1 to 8.

The organic ligand L which can be bonded covalently to the support preferably has the general formula (BI):

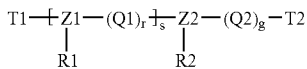

in which:
g=0 or is an integer of between 1 to 6;
r is an integer of between 1 to 6;
s=0 or is an integer of between 1 to 6;
Z1 and Z2 are independently of one another a heteroatom or a heterocyclic or heteroaromatic ring, Z1 and/or Z2 can optionally be substituted by at least one functional group E, as indicated below;
Q1 and Q2 are independently a group of the following formula:

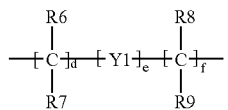

in which:

$10 > d+e+f \geq 1$; $d=0-9$; $e=0-9$; $f=0-9$;

each Y1 is selected independently of the others from the group —O—, —S—, —SO—, —SO$_2$—, -(G$^1$)N—, -(G$^1$)(G$^2$)N— (in which G$^1$ and/or G$^2$ are defined below), —C(O)—, arylene, alkylene, heteroarylene, —P— and/or —P(O)—;
if s>1, each group -[-Z1(R1)-(Q1)r-]- is defined independently of the others;
R1, R2, R6, R7, R8 and R9 are independently of one another —H, —OH, —OR (in which R=alkyl, alkenyl, cycloalkyl, heterocycloalkyl, aryl, heteroaryl or carbonyl group), —OAr, alkyl, alkenyl, cycloalkyl, heterocycloalkyl, aryl, heteroaryl and/or carbonyl group, each R, Ar, alkyl, alkenyl, cycloalkyl, heterocycloalkyl, aryl, heteroaryl and/or carbonyl group can be substituted by at least one functional group E, or R6 together with R7 and/or independently thereof R8 together with R9 can be oxygen;
E stands for functional groups containing O, S, P, N, Se, halogen, and/or any desired electron donor and/or any desired electron-withdrawing group, preferably E is —OH, mono- or polycarboxylate derivatives, aryl, heteroaryl, sulfonate, thiol (—RSH), thioether, (—R—S—R'), disulfides (—RSSR'), dithiolene, mono- or polyphosphonate, mono- of the polyphosphates, electron donor groups and/or electron-withdrawing groups, and/or groups with the formula (G$^1$)(G$^2$)N—, (G$^1$)(G$^2$)(G$^3$)N—, (G$^1$)(G$^2$)N—C(O)—, G$^3$O— and/or G$^3$C(O)—, in which each G$^1$, G$^2$ and/or G$^3$ independently of the others is H, alkyl, electron donor groups and/or electron-withdrawing groups, including those mentioned above;

R1-R9 can be a bridging group, preferably attached to another part of a representative of the same general formula;
T1 and T2 are independently of one another R4 or R5, in which R4 or R5 is defined like R1-R9, or if g=0 and/or s>0, R1 with R4, and/or R2 with R5, can independently of one another be =CH—R10, in which R10 is defined like R1-R9; or
T1 and T2 can be -T2-T1-, optionally they may form a covalent bond, if s>1 and/or g>0;
if Z1 and/or Z2=N or T1 and T2 are a are a single bond and/or R1 and/or R2 are absent, Q1 and/or Q2 are independently of one another a group of the general formula:

in which at least two R1, R2, R6, R7, R8 and/or R9 independently of one another are connected by means of a covalent bond;
if Z1 and/or Z2=oxygen, R1 and/or R2 may be absent;
if Z1 and/or Z2=S, N, P, B or Si then R1 and/or R2 can be absent;
if Z1 and/or Z2=a heteroatom substituted by a functional group E, then R1 and/or R2 and/or R4 and/or R5 can be absent.

The groups Z1 and/or Z2 are a heteroatom such as N, P, O, S, B and/or Si, preferably a substituted heterocyclic ring or if desired a substituted heteroaromatic ring selected from the group consisting of pyridines, pyrimidines, pyrazines, pyrazidines, pyrazoles, pyrroles, imidazoles, benzimidazoles, quinolines, isoquinolines, carbazoles, triazoles, indoles, isoindoles, furans, thiophenes, oxazoles and/or thiazoles.

The group R1-R9 is preferably —H, hydroxyl-C$_0$-C$_{20}$-alkyl, halo-C$_0$-C$_{20}$-alkyl, nitroso, fornyl-C$_0$-C$_{20}$-alkyl, carboxyl-C$_0$-C$_{20}$-alkyl and/or esters and/or salts thereof, carbamoyl-C$_0$-C$_{20}$-alkyl, sulfo-C$_0$-C$_{20}$-alkyl and/or esters and/or salts thereof, sulfamoyl-C$_0$-C$_{20}$-alkyl, amino-C$_0$-C$_{20}$-alkyl, aryl-C$_0$-C$_{20}$-alkyl, heteroaryl-C$_0$-C$_{20}$-alkyl, C$_0$-C$_{20}$-alkyl, alkoxy-C$_0$-C$_8$-alkyl, carbonyl-C$_0$-C$_6$-alkoxy and/or aryl-C$_0$-C$_6$-alkyl and/or C$_0$-C$_{20}$-alkylamides.

At least one R1-R9 can be a bridging group which joins a ligand molecule to a molecule of another ligand, preferably to a ligand of the same formula.

The bridging group preferably has the formula —Cn'(R11)(R12)-(D)p-Cm'(R11)(R12)- and joins the two molecules, in which p is 0 or 1, D is a heteroatom or a group containing a heteroatom, or is part of an aromatic or saturated homonuclear or heteronuclear ring, n' is an integer of between 1 to 4, m' is an integer of between 1 to 4, with the exception that, if $n'+m' \leq 4$, R11 and/or R12 are selected independently from the group consisting of —H, NR13, and/or OR14, alkyl, aryl, optionally substituted, and R13 and/or R14=—H, alkyl, aryl, both optionally substituted. Alternatively or additionally it is possible for at least two of R1-R9 to be atoms connecting bridging groups, preferably heteroatoms, the bridging group containing alkylene, hydroxyalkylene or heteroaryl.

A further modified group which can be used in accordance with the invention is based on the formula (BI) where the groups T1 and/or T2 form a single bond and s>1, in accordance with the general formula (BII):

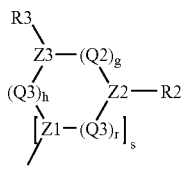

in which Z3 independently of the others is a group defined like Z1 or Z2; R3 independently of the others is a group defined like R1-R9; Q3 independently of the others is a group defined like Q1, Q2; h=0 or 1 to 6; and/or s'=s−1.

With preference it is possible in accordance with the invention to use organic ligands of the general formula (BII) in which s'=1, 2 or 3; r=g=h=1; d=2 or 3; e=f=0; R6=R7=H, preferably such that the ligand(s) has one of the following structures:

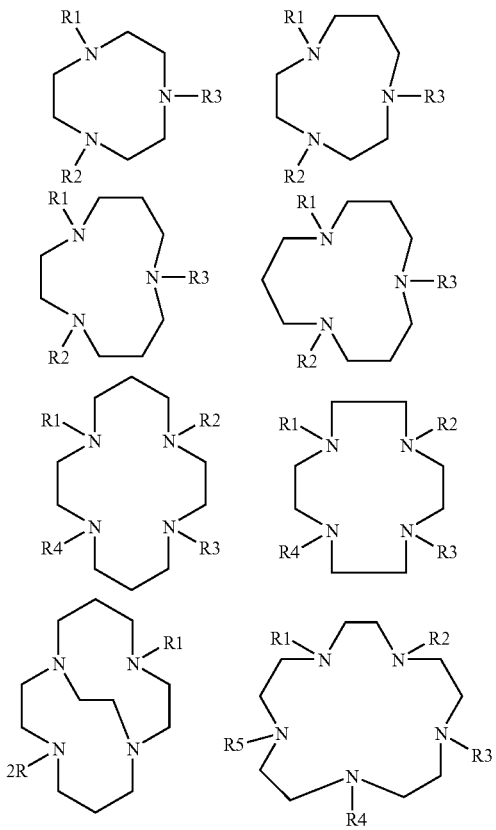

In the case of these preferred examples R1, R2, R3 and/or R4 is selected independently from the group consisting of —H, alkyl, aryl, heteroaryl, and/or at least one of R1-R4 is a bridging group attached to a molecule of the same formula and/or at least two of R1-R4 together form a bridging group joined to N atoms of the same compound; preferably the bridging group is alkylene or hydroxyalkylene or a heteroaryl-containing bridge, preferably heteroarylene. More preferably still, R1, R2, R3 and/or R4 are selected independently of one another from the group consisting of —H, methyl, ethyl, isopropyl, nitrogen-containing heteroaryl, or a group bridging the molecule of the same general formula or a group bridging the molecule of the same general formula via N atoms, said group being preferably alkylene or hydroxyalkylene.

The aforementioned complex $[M_aL_kX_n]Y_m$ preferably comprises:
M=Mn(II)-(IV), Cu(I)-(III), Fe(II)-(III), Co(II)-(III);
X=$CH_3CN$, $OH_2$, $Cl^-$, $Br^-$, $OCN^-$, $N_3^-$, $SCN^-$, $OH^-$, $O_2^-$, $PO_4^{3-}$, $C_6H_5BO_2^{2-}$, $RCOO^-$;
Y=$ClO_4^-$, $BPh_4^-$, $Br^-$, $Cl^-$, $[FeCl_4]^-$, $PF_6^-$, $NO_3^-$
a=1, 2, 3, 4;
n=0, 1, 2, 3, 4, 5, 6, 7, 8, 9;
m=1, 2, 3, 4; and/or
k=1, 2, 4.

In accordance with the general formula (BII) in which s'=2; r=g=h=1; d=f=0; e=1; and/or each Y1 is independently of the others alkylene or heteroarylene. The ligand preferably has the general formula:

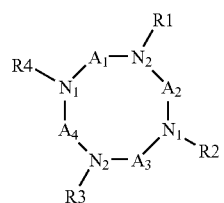

in which:
A1, A2, A3 and A4 are selected independently of one another from the group consisting of C1-9 alkylene or heteroarylene groups; and/or N1 and/or N2 are independently of one another a heteroatom or a heteroarylene group.

Preferably N1 is an aliphatic nitrogen, N2 is a heteroarylene group, R1, R2, R3 and R4 are each independently of one another —H, alkyl, aryl or heteroaryl, and/or A1, A2, A3 and A4 are each —CH2-.

One of the R1-R4 can be a group bridging the molecule of the same general formula and/or at least two of the R1-R4 can be a group bridging the molecule of the same general formula via N atoms; preferably the bridging group is alkylene or hydroxyalkylene or a heteroaryl-containing bridge, preferably heteroarylene. Preferably R1, R2, R3 and/or R4 are selected independently of one another from the group consisting of —H, methyl, ethyl, isopropyl, nitrogen-containing heteroaryl, or a group bridging the molecule of the same general formula or an alkylene or hydroxyalkylene group bridging the molecule of the same general formula via N atoms.

The ligand preferably had the general formula:

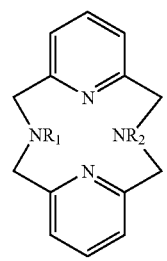

in which R1, R2 independently of one another are —H, alkyl, aryl or heteroaryl.

The complex $[M_aL_kX_n]Y_m$ preferably comprises:
M=Fe(II)-(III), Mn(II)-(IV), Cu(II), Co(II)-(III);
X=$CH_3CN$, $OH_2$, $Cl^-$, $Br^-$, $OCN^-$, $N_3^-$, $SCN^-$, $OH^-$, $O_2^-$, $PO_4^{3-}$, $C_6H_5BO_2^{2-}$, $RCOO^-$;
Y=$ClO_4^-$, $BPh_4^-$, $Br^-$, $Cl^-$, $[FeCl_4]^-$, $PF_6^-$, $NO_3^-$;
a=1, 2, 3, 4;
n=0, 1, 2, 3, 4, 5, 6, 7, 8, 9;
m=1, 2, 3, 4; and/or
k=1, 2, 4.

A further ligand which can be used in accordance with the invention and which can be joined covalently to the support is based on the general formula (BII) with s'=2 and/or r=g=h=1, in accordance with the general formula:

in which:

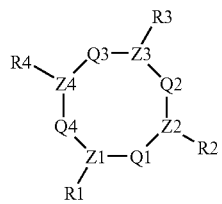

preferably each Z1-Z4 is a heteroaromatic ring; e=f=0; d=1; and/or R7 is absent; preferably R1=R2=R3=R4=2,4,6-trimethyl-3-$SO_3Na$-phenyl, 2,6-diCl-3(or 4)-$SO_3Na$-phenyl.

Alternatively each Z1-Z4 is N; R1-R4 is absent; both Q1 and/or Q3 are =CH—[—Y1-]$_e$—CH=; and/or both Q2 and/or Q4 are —CH2-[—Y1-]$_n$—CH2-.

The ligand which can be used in accordance with the invention and can be bonded covalently to the support preferably has the general formula:

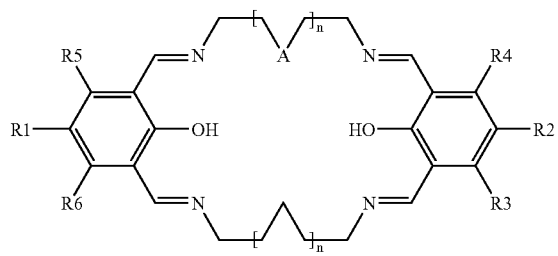

in which:
A is an optionally substituted alkylene, optionally interrupted by a heteroatom; and/or n is zero or an integer of between 1 to 5.
Preferably R1-R6 are hydrogen, n=1 and/or A=CH2-, —CHOH—, —CH2N(R)CH2- or —CH2CH2N(R)CH2CH2-, in which R is hydrogen or alkyl, more preferably A is —CH2-, —CHOH— or —CH2CH2NHCH2CH2-.

Further it is preferred if the corresponding complex $[M_aL_kX_n]Y_m$ comprises:
M=Mn(II)-(IV), Co(II)-(III), Fe(II)-(III);
X=$CH_3CN$, $OH_2$, $Cl^-$, $Br^-$, $OCN^-$, $N_3^-$, $SCN^-$, $OH^-$, $O_2^-$, $PO_4^{3-}$, $C_6H_5BO_2^{2-}$, $RCOO^-$;
Y=$ClO_4^-$, $BPh_4^-$, $Br^-$, $Cl^-$, $[FeCl_4]^-$, $PF_6^-$, $NO_3^-$;
a=1, 2, 3, 4;
n=0, 1, 2, 3, 4, 5, 6, 7, 8, 9;
m=1, 2, 3, 4; and/or
k=1, 2, 4.

In a further modification of (BI), T1 and/or T2 are independently of one another the groups R4, R5, as defined for R1-R9, in accordance with the general formula (BIII):

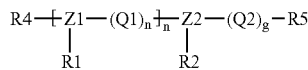

In this general formula (BIII) s=1; r=1; g=0; d=f=1; e=1-4; Y1=—CH2-; and/or R1 together with R4, and/or R2 together with R5, are

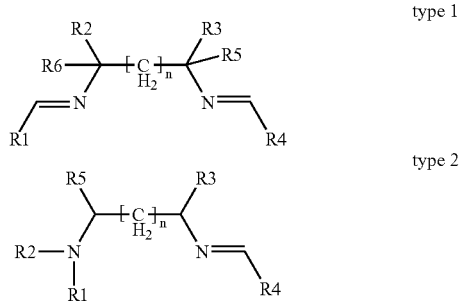

independently of one another =CH—R10, in which R10 is defined like R1-R9. R2 can together with R5 be =CH—R10, and R1 and R4 can be two separate groups. Alternatively both R1 together with R4, and/or R2 together with R5, are independently of one another =CH—R10. A preferred ligand which can be used in accordance with the invention and can be linked covalently to a support has the following formula:

preferably this ligand is selected from the group consisting of:

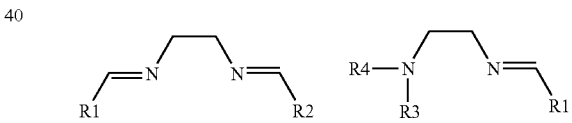

in which:
R1 and/or R2 are selected from the group consisting of phenols, heteroaryl-$C_0$-$C_{20}$-alkyls, optionally substituted; R3 and/or R4 are selected from the group consisting of —H, alkyl, aryl, optionally substituted phenols, heteroaryl-$C_0$-$C_{20}$-alkyls, alkylaryl, aminoalkyl, alkoxy; with further preference R1 and/or R2 are selected from the group consisting of optionally substituted phenols, heteroaryl-$C_0$-$C_2$-alkyls, R3 and/or R4 are selected from the group consisting of —H, alkyl, aryl, optionally substituted phenols and/or nitrogen-heteroaryl-$C_0$-$C_2$-alkyl.

The corresponding complex $[M_aL_kX_n]Y_m$ may preferably comprise:
M=Mn(II)-(IV), Co(II)-(III), Fe(II)-(III);
X=$CH_3CN$, $OH_2$, $Cl^-$, $Br^-$, $OCN^-$, $N_3^-$, $SCN^-$, $OH^-$, $O_2$, $PO_4^{3-}$, $C_6H_5BO_2^{2-}$, $RCOO^-$;
Y=$ClO_4^-$, $BPh_4^-$, $Br^-$, $Cl^-$, $[FeCl_4]^-$, $PF_6^-$, $NO_3^-$;
a=1, 2, 3, 4;
n=0, 1, 2, 3, 4, 5, 6, 7, 8, 9;
m=1, 2, 3, 4; and/or
k=1, 2, 4.

In a further variant in accordance with the general formula (BIII) s=1; r=1; g=0; d=f=1; e=1-4; Y1=—C(R')(R"), in which R' and/or R", defined independently of one another, are like R1-R9.

The ligand which can be used in accordance with the invention preferably has the general formula:

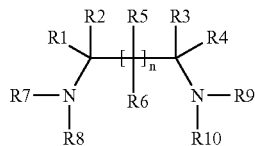

The groups R1, R2, R3, R4, R5 in this formula are preferably —H or $C_0$-$C_{20}$ alkyl, n=0 or 1, R6 is —H, alkyl, —OH or —SH, and/or R7, R8, R9, R10 are preferably each independently of one another selected from the group consisting of —H, $C_0$-$C_{20}$-alkyl, heteroaryl-$C_0$-$C_{20}$-alkyl, alkoxy-$C_0$-$C_8$-alkyl and/or amino-$C_0$-$C_{20}$-alkyl.

The corresponding complex $[M_a L_k X_n]Y_m$ preferably comprises:
M=Mn(II)-(IV), Fe(II)-(III), Cu(II), Co(II)-(III);
X=$CH_3CN$, $OH_2$, $Cl^-$, $Br^-$, $OCN^-$, $N_3^-$, $SCN^-$, $OH^-$, $O_2^-$, $PO_4^{3-}$, $C_6H_5BO_2^{2-}$, $RCOO^-$;
Y=$ClO_4^-$, $BPh_4^-$, $Br^-$, $Cl^-$, $[FeCl_4]^-$, $PF_6^-$, $NO_3^-$;
a=1, 2, 3, 4;
n=0, 1, 2, 3, 4;
m=0, 1, 2, 3, 4, 5, 6, 7, 8; and/or
k=1, 2, 3, 4.

A further ligand suitable in accordance with the invention which bonds covalently to a support possesses the general formula (BIII), s=0; g=1; d=e=0; f=1-4. Preferably this ligand has the general formula:

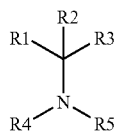

It is even more preferred if the ligand has the following general formula:

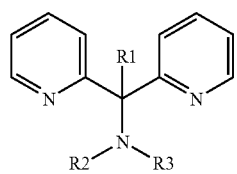

in which:
R1, R2 and R3 are defined like R2, R4 and R5.
The corresponding complex $[M_a L_k X_n]Y_m$ is indicated below:
M=Mn(II)-(IV), Fe(II)-(III), Cu(II), Co(II)-(III);
X=$CH_3CN$, $OH_2$, $Cl^-$, $Br^-$, $OCN^-$, $N_3^-$, $SCN^-$, $OH^-$, $O_2^-$, $PO_4^{3-}$, $C_6H_5BO_2^{2-}$, $RCOO^-$;
Y=$ClO_4^-$, $BPh_4^-$, $Br^-$, $Cl^-$, $[FeCl_4]^-$, $PF_6^-$, $NO_3^-$;
a=1, 2, 3, 4;
n=0, 1, 2, 3, 4;
m=0, 1, 2, 3, 4, 5, 6, 7, 8; and/or
k=1, 2, 3, 4.

Yet another complex which can be used in accordance with the invention and which can be bonded covalently to a support via at least one organic ligand has the general formula (A):

$[LMX_n]^z Y_q$ in which
M is Fe in oxidation state II, III, IV or V, Mn in oxidation state II, III, IV, VI or VII, Cu in oxidation state I, II or III, Co in oxidation state II, III or IV, or Cr in oxidation state II-VI;
X is an atom or molecule capable of coordination;
n is zero or an integer in the range of between 0 to 3;
z is the charge of the complex and is an integer which may be positive, zero or negative;
Y is a counterion, the counterion being dependent on the charge of the complex;
q=z/[charge of Y]; and/or
L is a pentadentate ligand of the general formula (B):

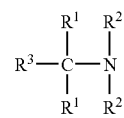

in which:
each $R^1$, $R^2$ independently of the other are —R4-R5,
$R^3$ is hydrogen, optionally substituted alkyl, aryl or arylalkyl, or —$R^4$-$R^5$,
each $R^4$ are independently of one another a single bond or optionally substituted alkylene, alkenylene, oxyalkylene, aminoalkylene, alkylene ether, carboxyl ester of carboxyl amide, and/or
each $R^5$ is independently of the others an optionally N-substituted aminoalkyl group or an optionally substituted heteroaryl group selected from the group consisting of pyridinyl, pyrazinyl, pyrazolyl, pyrrolyl, imidazolyl, benzimidazolyl, pyrimidinyl, triazolyl and/or thiazolyl.

The ligand L has the general formula (B) as indicated above and is a pentadentate ligand. The term 'pentadentate', in the sense of this invention means that five heteroatoms are able to coordinate the metal M ion in the metal complex.

According to the formula (B) one coordinating heteroatom is the nitrogen present in the methylamine chain (peptide chain) and/or one coordinating heteroatom is preferably present in each of the four $R^1$ and/or $R^2$ side groups. Preferably all of the coordinating heteroatoms are nitrogen atoms.

The ligand L of the formula (B) preferably comprises at least two substituted or unsubstituted heteroaryl groups in the four side groups. The heteroaryl group is preferably a pyridin-2-yl group and/or, if substituted, preferably a methyl- or ethyl-substituted pyridin-2-yl group. More preferably still, the heteroaryl group is an unsubstituted pyridin-2-yl group. The heteroaryl group is preferably connected to methylamine, preferably via the N atom thereof, by means of a methylene group. Preferably the ligand L of the formula (B) contains at least one substituted amino-alkyl side group, more preferably two aminoethyl side groups, more preferably still 2-(N-alkyl)aminoethyl or 2-(N,N-dialkyl)aminoethyl.

In formula (B) preferably $R^1$ is pyridin-2-yl or $R^2$ is pyridin-2-ylmethyl. Preferably $R^2$ of $R^1$ are 2-aminoethyl, 2-(N-(m)ethyl)aminoethyl or 2-(N,N-di(m)ethyl)aminoethyl. If substituted, R⁵ is preferably 3-methylpyridin-2-yl. R³ is preferably hydrogen, benzyl or methyl.

Examples of preferred ligands L which can be used in accordance with the invention, of formula (B), in the simplest form thereof are:

(i) pyridin-2-yl containing ligands such as:
N,N-bis(pyridin-2-yl-methyl)bis(pyridin-2-yl)methylamine;
N,N-bis(pyrazol-1-yl-methyl)bis(pyridin-2-yl)methylamine;
N,N-bis(imidazol-2-yl-methyl)bis(pyridin-2-yl)methylamine;
N,N-bis(1,2,4-triazol-1-yl-methyl)bis(pyridin-2-yl)methylamine;
N,N-bis(pyridin-2-yl-methyl)bis(pyrazol-1-yl)methylamine;
N,N-bis(pyridin-2-yl-methyl)bis(imidazol-2-yl)methylamine;
N,N-bis(pyridin-2-yl-methyl)bis(1,2,4-triazol-1-yl)methylamine;
N,N-bis(pyridin-2-yl-methyl)-1,1-bis(pyridin-2-yl)-1-aminoethane;
N,N-bis(pyridin-2-yl-methyl)-1,1-bis(pyridin-2-yl)-2-phenyl-1-aminoethane;
N,N-bis(pyrazol-1-yl-methyl)-1,1-bis(pyridin-2-yl)-1-aminoethane;
N,N-bis(pyrazol-1-yl-methyl)-1,1-bis(pyridin-2-yl)-2-phenyl-1-aminoethane;
N,N-bis(imidazol-2-yl-methyl)-1,1-bis(pyridin-2-yl)-1-aminoethane;
N,N-bis(imidazol-2-yl-methyl)-1,1-bis(pyridin-2-yl)-2-phenyl-1-aminoethane;
N,N-bis(1,2,4-triazol-1-yl-methyl)-1,1-bis(pyridin-2-yl)-1-aminoethane;
N,N-bis(1,2,4-triazol-1-yl-methyl)-1,1-bis(pyridin-2-yl)-2-phenyl-1-aminoethane;
N,N-bis(pyridin-2-yl-methyl)-1,1-bis(pyrazol-1-yl)-1-aminoethane;
N,N-bis(pyridin-2-yl-methyl)-1,1-bis(pyrazol-1-yl)-2-phenyl-1-aminoethane;
N,N-bis(pyridin-2-yl-methyl)-1,1-bis(imidazol-2-yl)-1-aminoethane;
N,N-bis(pyridin-2-yl-methyl)-1,1-bis(imidazol-2-yl)-2-phenyl-1-aminoethane;
N,N-bis(pyridin-2-yl-methyl)-1,1-bis(1,2,4-triazol-1-yl)-1-aminoethane;
N,N-bis(pyridin-2-yl-methyl)-1,1-bis(1,2,4-triazol-1-yl)-1-aminoethane;
N,N-bis(pyridin-2-yl-methyl)-1,1-bis(pyridin-2-yl)-1-aminoethane;
N,N-bis(pyridin-2-yl-methyl)-1,1-bis(pyridin-2-yl)-1-aminohexane;
N,N-bis(pyridin-2-yl-methyl)-1,1-bis(pyridin-2-yl)-2-phenyl-1-aminoethane;
N,N-bis(pyridin-2-yl-methyl)-1,1-bis(pyridin-2-yl)-2-(4-sulfonic acid phenyl)-1-aminoethane;
N,N-bis(pyridin-2-yl-methyl)-1,1-bis(pyridin-2-yl)-2-(pyridin-2-yl)-1-aminoethane;
N,N-bis(pyridin-2-yl-methyl)-1,1-bis(pyridin-2-yl)-2-(pyridin-3-yl)-1-aminoethane;
N,N-bis(pyridin-2-yl-methyl)-1,1-bis(pyridin-2-yl)-2-(pyridin-4-yl)-1-aminoethane;
N,N-bis(pyridin-2-yl-methyl)-1,1-bis(pyridin-2-yl)-2-(1-alkyl-pyridinium-4-yl)-1-aminoethane;
N,N-bis(pyridin-2-yl-methyl)-1,1-bis(pyridin-2-yl)-2-(1-alkyl-pyridinium-3-yl)-1-aminoethane;
N,N-bis(pyridin-2-yl-methyl)-1,1-bis(pyridin-2-yl)-2-(1-alkyl-pyridinium-2-yl)-1-aminoethane;

(ii) 2-aminoethyl containing ligands such as:
N,N-bis(2-(N-alkyl)amino-ethyl)bis(pyridin-2-yl)methylamine;
N,N-bis(2-(N-alkyl)amino-ethyl)bis(pyrazol-1-yl)methylamine;
N,N-bis(2-(N-alkyl)amino-ethyl)bis(imidazol-2-yl)methylamine;
N,N-bis(2-(N-alkyl)amino-ethyl)bis(1,2,4-triazol-1-yl)methylamine;
N,N-bis(2-(N,N-dialkyl)amino-ethyl)bis(pyridin-2-yl)methylamine;
N,N-bis(2-(N,N-dialkyl)amino-ethyl)bis(pyrazol-1-yl)methylamine;
N,N-bis(2-(N,N-dialkyl)amino-ethyl)bis(imidazol-2-yl)methylamine;
N,N-bis(2-(N,N-dialkyl)amino-ethyl)bis(1,2,4-triazol-1-yl)methylamine;
N,N-bis(pyridin-2-yl-methyl)bis(2-amino-ethyl)methylamine;
N,N-bis(pyrazol-1-yl-methyl)bis(2-amino-ethyl)methylamine;
N,N-bis(imidazol-2-yl-methyl)bis(2-amino-ethyl)methylamine;
N,N-bis(1,2,4-triazol-1-yl-methyl)bis(2-amino-ethyl)methylamine.

Particularly preferred ligands:
N,N-bis(pyridin-2-yl-methyl)bis(pyridin-2-yl)methylamine, referred to below as N4Py;
N,N-bis(pyridin-2-yl-methyl)-1,1-bis(pyridin-2-yl)-1-aminoethane, referred to below as MeN4Py;
N,N-bis(pyridin-2-yl-methyl)-1,1-bis(pyridin-2-yl)-2-phenyl-1-aminoethane, referred to below as BzN4Py.

A further ligand complex which can be used in accordance with the invention is based on the general complex formula (A) and ligand (B) as indicated above, but with the exception that R³ is hydrogen.

Alternatively the organic substance forms a complex of the general formula (A) as indicated above, but with the exception that L is a pentadentate or hexadentate ligand of the general formula (C):

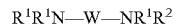

in which:
each R¹ independently of the others is —R³—V, in which R³ is optionally substituted alkylene, alkenylene, oxyalkylene, aminoalkylene or alkylene ether and/or V is an optionally substituted heteroaryl group selected from the group consisting of pyridinyl, pyrazinyl, pyrazolyl, pyrrolyl, imidazolyl, benzimidazolyl, pyrimidinyl, triazolyl and/or thiazolyl;

W is an optionally substituted alkylene bridge group selected from the group consisting of —CH2CH2-, —CH2CH2CH2-, —CH2CH2CH2CH2-, —CH2-C6H4-CH2-, —CH2-C6H10-CH2- and/or —CH2-C10H6-CH2-; and/or R² is a group selected from the group consisting of R¹, and/or alkyl, aryl or arylalkyl groups, optionally substituted by a substituent selected from the group consisting of hydroxyl, alkoxy, phenoxy, carboxylate, carboxamide, carboxyl ester, sulfonate, amine, alkylamine and/or N⁺(R⁴)₃, in which R⁴ is selected from the group consisting of hydrogen, alkanyl, alkenyl, arylalkanyl, arylalkenyl, oxyalkanyl, oxyalkenyl, aminoalkanyl, aminoalkenyl, alkanyl ether and/or alkenyl ether.

The ligand L has the general formula (C) as indicated above and is a pentadentate ligand or, if $R^1=R^2$, it can be a hexadentate ligand. The term 'pentadentate' in the sense of this invention means as indicated above that five heteroatoms can coordinate the metal M ion in the metal complex. The term 'hexadentate' in the sense of this invention means that in principle six heteroatoms can coordinate the metal M ion in the metal complex. In the case of hexadentate ligands, however, generally only a maximum of five of the six ligands coordinate.

In the formula (C) two heteroatoms are joined by a bridging group W and/or at least one coordinating heteroatom is present in each of the three $R^1$ groups. Preferably the coordinating heteroatom is a nitrogen atom.

The ligand L of the formula (C) preferably comprises at least one optionally substituted heteroaryl group in each of the three $R^1$ groups. The heteroaryl group is preferably a pyridin-2-yl group, in particular a methyl- or ethyl-substituted pyridin-2-yl group. The heteroaryl group is attached via an N atom in formula (C), preferably via an alkylene group and more preferably via a methylene group. Most preferably the heteroaryl group is a 3-methylpyridin-2-yl group which is joined to an N atom via methylene.

The group $R^2$ in formula (C) is a substituted or unsubstituted alkyl, aryl or arylalkyl group, or a group $R^1$. Preferably $R^2$ is different from each of the $R^1$ groups in the formula indicated above. Preferably $R^2$ is methyl, ethyl, benzyl, 2-hydroxyethyl or 2-methoxyethyl. More preferably still $R^2$ is methyl or ethyl.

The bridging group W can be a substituted or unsubstituted alkylene group selected from the group consisting of —CH2CH2-, —CH2CH2CH2-, —CH2CH2CH2CH2-, —CH2-C6H4-CH2-, —CH2-C6H10-CH2-, and/or —CH2-C10H6-CH2- (in which —C6H4-, —C6H10-, —C10H6- can be ortho-, para- or meta-C6H4-, —C6H10-, —C10H6-). Preferably the bridging group W is an ethylene or 1,4-butylene group, more preferably still an ethylene group.

Preferably V is substituted pyridin-2-yl, in particular methyl-substituted or ethyl-substituted pyridin-2-yl, and/or more preferably still V is 3-methylpyridin-2-yl.

Examples of preferred ligands of the formula (C) in their most simple form are:
N-methyl-N,N',N'-tris(3-methylpyridin-2-ylmethyl)ethylene-1,2-diamine;
N-ethyl-N,N',N'-tris(3-methylpyridin-2-ylmethyl)ethylene-1,2-diamine;
N-benzyl-N,N',N'-tris(3-methylpyridin-2-ylmethyl)ethylene-1,2-diamine;
N-(2-hydroxyethyl)-N,N',N'-tris(3-methylpyridin-2-ylmethyl)ethylene-1,2-diamine;
N-(2-methoxyethyl)-N,N',N'-tris(3-methylpyridin-2-ylmethyl)ethylene-1,2-diamine;
N-methyl-N,N',N'-tris(5-methylpyridin-2-ylmethyl)ethylene-1,2-diamine;
N-ethyl-N,N',N'-tris(5-methylpyridin-2-ylmethyl)ethylene-1,2-diamine;
N-benzyl-N,N',N'-tris(5-methylpyridin-2-ylmethyl)ethylene-1,2-diamine;
N-(2-hydroxyethyl)-N,N',N'-tris(5-methylpyridin-2-ylmethyl)ethylene-1,2-diamine;
N-(2-methoxyethyl)-N,N',N'-tris(5-methylpyridin-2-ylmethyl)ethylene-1,2-diamine;
N-methyl-N,N',N'-tris(3-ethylpyridin-2-ylmethyl)ethylene-1,2-diamine;
N-ethyl-N,N',N'-tris(3-ethylpyridin-2-ylmethyl)ethylene-1,2-diamine;
N-benzyl-N,N',N'-tris(3-ethylpyridin-2-ylmethyl)ethylene-1,2-diamine;
N-(2-hydroxyethyl)-N,N',N'-tris(3-ethylpyridin-2-ylmethyl)ethylene-1,2-diamine;
N-(2-methoxyethyl)-N,N',N'-tris(3-ethylpyridin-2-ylmethyl)ethylene-1,2-diamine;
N-methyl-N,N',N'-tris(5-ethylpyridin-2-ylmethyl)ethylene-1,2-diamine;
N-ethyl-N,N',N'-tris(5-ethylpyridin-2-ylmethyl)ethylene-1,2-diamine;
N-benzyl-N,N',N'-tris(5-ethylpyridin-2-ylmethyl)ethylene-1,2-diamine; and/or
N-(2-methoxyethyl)-N,N',N'-tris(5-ethylpyridin-2-ylmethyl)ethylene-1,2-diamine.

Particularly preferred ligands which can be used in accordance with the invention and can be bonded covalently to a support are:
N-methyl-N,N',N'-tris(3-methylpyridin-2-ylmethyl)ethylene-1,2-diamine;
N-ethyl-N,N',N'-tris(3-methylpyridin-2-ylmethyl)ethylene-1,2-diamine;
N-benzyl-N,N',N'-tris(3-methylpyridin-2-ylmethyl)ethylene-1,2-diamine;
N-(2-hydroxyethyl)-N,N',N'-tris(3-methylpyridin-2-ylmethyl)ethylene-1,2-diamine; and/or
N-(2-methoxyethyl)-N,N',N'-tris(3-methylpyridin-2-ylmethyl)ethylene-1,2-diamine.

Most-preferred ligands which can be used in accordance with the invention and can be bonded covalently to a support are:
N-methyl-N,N',N'-tris(3-methylpyridin-2-ylmethyl)ethylene-1,2-diamine; and/or
N-ethyl-N,N',N'-tris(3-methylpyridin-2-ylmethyl)ethylene-1,2-diamine.

The metal M in formula (A) is preferably Fe or Mn, more preferably still Fe.

Preferably coordinating atoms/molecules X in formula (A) may be selected from the group consisting of $R^6OH$, $NR^6_3$, $R^6CN$, $R^6OO-$, $R^6S-$, $R^6O-$, $R^6COO-$, $OCN^-$, $SCN^-$, $N_3^-$, $CN^-$, $F^-$, $Cl^-$, $Br^-$, $I^-$, $O_2^-$, $NO_3^-$, $NO_2^-$, $SO_4^{2-}$, $SO_3^{2-}$, $PO_4^{3-}$ and/or aromatic N donors selected from the group consisting of pyridines, pyrazines, pyrazoles, pyrroles, imidazoles, benzimidazoles, pyrimidines, triazoles and/or thiazoles, in which $R^6$ is preferably selected from the group consisting of hydrogen, optionally substituted alkyl and/or optionally substituted aryl. X may also be LMO— or LMOO—, in which M is a transition metal and L is ligand, as indicated above. The X capable of coordination is preferably selected from the group consisting of $CH_3CN$, $H_2O$, $F^-$, $Cl^-$, $Br^-$, $OOH^6$, $R^6COO^-$, $R^6O^-$, $LMO^-$, and/or $LMOO^-$ in which $R^6$ is hydrogen or optionally substituted phenyl, naphthyl, or C1-C4 alkyl.

The counterion Y in formula (A) compensates the charge z of the complex formed by the ligand L, of the metal M and/or of the coordinating X. If the charge z is positive, Y can be anion, for example $R^7COO^-$, $BPh_4^-$, $ClO_4^-$, $BF_4^-$, $PF_6^-$, $R^7SO_3^-$, $R^7SO_4^-$, $SO_4^{2-}$, $NO_3^-$, $F^-$, $Cl^-$, $Br^-$, or $I^-$, with $R^7$=hydrogen, optionally substituted alkyl or optionally substituted aryl. If z is negative Y is a customary cation, for example an alkali metal, alkaline earth metal or an (alkyl) ammonium cation.

Suitable counterions Y are also ions which bring about the formation of storage-stable solids. Preferred counterions of preferred metal complexes are selected from the group consisting of $R^7COO^-$, $ClO_4^-$, $BF_4^-$, $PF_6^-$, $R^7SO_3^-$ (especially $CF_3SO_3^-$), $R^7SO_4^-$, $SO_4^{2-}$, $NO_3^-$, $F^-$, $Cl^-$, $Br^-$, and/or $I^-$, in which $R^7$ is hydrogen or optionally substituted phenyl, naphthyl or C1-C4 alkyl.

A further suitable ligand complex which can be used in accordance with the invention and can be bonded covalently to a support via at least one ligand has the following general formula (D):

$$[\{M'_aL\}_bX_c]^zY_q$$

in which:

M' is hydrogen or a metal selected from the group consisting of Ti, V, Co, Zn, Mg, Ca, Sr, Ba, Na, K and/or Li;

X is a coordinating atom/molecule;

a is an integer in the range of between 1 to 5;

b is an integer in the range of between 1 to 4;

c is zero or an integer in the range of between 0 to 5;

z is the charge of the compound and is an integer which may be positive, zero or negative;

Y is a counterion which is selected in dependence on the charge of the compound;

q=z/[charge of Y]; and/or

L is a pentadentate ligand of the general formula (B) or (C) as indicated above.

A suitable organic substance comprises a macrocyclic ligand of the formula (E):

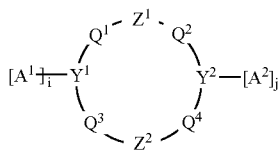

in which:

$Z^1$ and/or $Z^2$ independently of one another are selected from the group consisting of monocyclic or polycyclic aromatic ring structures optionally containing at least one heteroatom, it being possible for each aromatic ring structure to be substituted by at least one substituent;

$Y^1$ and/or $Y^2$ are independently of one another selected from the group consisting of C, N, O, Si, P and/or S atoms;

$A^1$ and/or $A^2$ are selected independently of one another from the group consisting of hydrogen, alkyl, alkenyl and/or cycloalkyl, it being possible for each alkyl, alkenyl and/or cycloalkyl to be optionally substituted by at least one group selected from the group consisting of hydroxyl, aryl, heteroaryl, sulfonates, phosphates, electron donor groups and/or electron-withdrawing groups, and/or groups of the formula $(G^1)(G^2N-$, $G^3OC(O)-$, $G^3O-$ and/or $G^3C(O)-$, in which each $G^1$, $G^2$ and/or $G^3$ is selected independently of the others from the group consisting of hydrogen and/or alkyl, and/or electron donor group and/or electron-withdrawing groups (additionally to those mentioned above);

and/or j are selected from the group consisting of 0, 1 and/or 2, corresponding to the valence of $Y^1$ and/or $Y^2$;

each $Q^1$-$Q^4$ is selected independently of the others from the group of the following formula:

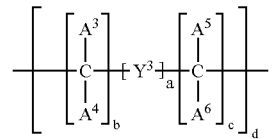

in which:

$10 > a+b+c > 2$ and/or $d \geq 1$;

each $Y^3$ is selected independently of the others from the group consisting of $-O-$, $-S-$, $-SO-$, $-SO_2-$, $-(G^1)N-$ (in which $G^1$ is as defined above), $-C(O)-$, arylene, heteroarylene, $-P-$ and/or $-P(O)-$;

each $A^3$-$A^6$ is selected independently of the others from the group consisting of the above-indicated groups $A^1$ and/or $A^2$; and in which at least two of $A^1$-$A^6$ form a bridging group, with the proviso that $A^1$ and/or $A^2$ are attached without at the same time being attached to $A^3$-$A^6$;

the bridging group joining $A^1$ and/or $A^2$ may contain at least one carbonyl group.

The ligand of the formula (E), unless indicated otherwise, embraces all alkyl, hydroxyalkyl alkoxy, and/or alkenyl groups, preferably having 1 to 6, more preferably having 1 to 4 carbon atoms.

Preferred electron donor groups include alkyl (e.g., methyl), alkoxy (e.g., methoxy), phenoxy, and/or unsubstituted, monosubstituted and/or disubstituted amine groups. Preferred electron-withdrawing groups include nitro, carboxyl, sulfonyl and/or halogen.

The ligand of the formula (E) can be present in the form of a ligand complex with transition metal atom or without transition metal atom. In the non-transition-metal-complexed form, the transition metal may originate from the ready-to-use composition, i.e., the medium, or may originate, for example, from a fluid medium, such as water, which is used together with the medium at the site of use. Mains water normally contains sufficient traces of transition metals.

A further ligand which can be used in accordance with the invention and can be bonded covalently to a support has the following formula (E) with a counterion of the formula (F):

$$[H_xL]^zY_q$$

in which:

H is a hydrogen atom;

Y is a counterion, the counterion being dependent on the charge of the complex;

x is an integer so that at least one nitrogen atom of L is protonated;

z is the charge of the complex and/or is an integer which is positive or zero;

q=z/[charge of Y]; and/or

L is a ligand of the formula (E) as indicated above.

In one embodiment which can be used further in accordance with the invention the organic substance forms a metal complex of the formula (G) based on the ion pair formation of the formula (F):

$$[M_xL]^zY_q$$

in which:

L, Y, x, z and/or q are as defined above in formula (F) and/or M is a metal selected from the group consisting of Mn in oxidation states II-V, Fe II-V, Cu I-III, Co I-III, Ni I-III, Cr II-VI, W IV-VI, Pd V, Ru II-IV, V III-IV and/or Mo IV-VI.

Preference is given to a complex of the formula (G) in which M is Mn, Co, Fe or Cu.

Preference is further given to an organic substance which forms a complex of the formula (H):

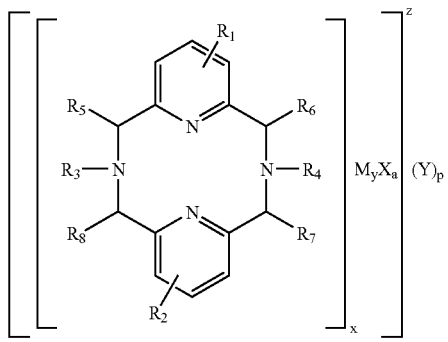

in which:

M is an Fe atom with the oxidation state II or III, Mn atom with the oxidation state II, III, IV or V, Cu atom with the oxidation state I, II or III, or Co atom with the oxidation state II, III or IV;

X is a bridging group or a nonbridging group between M, preferably Fe atom(s), Y is a counterion, x and/or y are $\geq 1$, $0 = <n = <3$ and z is the charge of the metal complex, and p="z/charge" of Y; R1 and/or R2 are independently of one another at least one ring substituent selected from the group consisting of hydrogen and/or electron donor and/or electron-withdrawing groups, R3 to R8 are independently of one another hydrogen, alkyl, hydroxyalkyl, alkenyl or derivatives thereof, if they are substituted by at least one electron donor and/or electron-withdrawing groups.

In the complex of the formula (H) M is preferably an Fe atom in oxidation state II or III or an Mn atom in oxidation state II, III, IV, or V. The oxidation state of M is preferably=III.

If M=Fe, the complex of the formula (H) is preferably in the form of an Fe salt, such as (in the oxidized state) dihalo-2,11-diazo[3.3](2,6)pyridinophane, dihalo-4-methoxy-2,11-diazo[3.3](2,6)pyridinophane and/or mixtures thereof, in particular in the form of a chloride salt.

If M is=Mn the complex of the formula (H) is preferably in the form of an Mn salt (in the oxidized state), such as N,N'-dimethyl-2,11-diazo[3.3](2,6)pyridinophane, in particular in the form of a monohexafluorophosphate salt.

Preferably X is selected from the group consisting of $H_2O$, $OH^-$, $O_2^-$, $SH^-$, $S^{2-}$, $SO_4^{2-}$, $NR_9R_{10}^-$, $RCOO^-$, $NR_9R_{10}R_{11}$, $Cl^-$, $Br^-$, $F^-$, $N_3^-$ and/or combinations thereof, in which $R_9$, $R_{10}$ and/or $R_{11}$ are selected independently of one another from the group consisting of —H, C1-4 alkyl and/or aryl, optionally with at least one electron-withdrawing and/or electron donor group. More preferably still X is a halogen, in particular a fluoride ion.

In the formulae (F), (G) and/or (H) the anionic counterion Y is preferably selected from the group consisting of $Cl^-$, $Br^-$, $I^-$, $NO_3^-$, $ClO_4^-$, $SCN^-$, $PF_6^-$, $RSO_3^-$, $RSO_4^-$, $CF_3SO_3^-$, $BPh_4^-$ and/or $OAc^-$. A cationic counterion is preferably not present.

In formula (H), R1 and/or R2 are preferably both hydrogen; R3 and/or R4 are preferably C1-4 alkyl, particularly methyl; R5-R8 are preferably in each case hydrogen.

The Fe or Mn containing catalyst of the formula (H) may be present in the form of a monomer, dimer or oligomer.

A further ligand which can be used in accordance with the invention may form the complex of the general formula (A1) in which L is a ligand of the general formula, or is a protonated or deprotonated analog thereof:

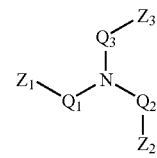

in which:

Z1, Z2 and/or Z3 independently of one another are a coordination group selected from the group consisting of carboxylate, amido, —NH—C(NH)NH2, hydroxyphenyl, optionally substituted heterocyclic ring or optionally substituted heteroaromatic ring selected from the group consisting of pyridine, pyrimidine, pyrazine, pyrazole, imidazole, benzimidazole, quinoline, quinoxaline, triazole, isoquinoline, carbazole, indole, isoindole, oxazole and/or thiazole; Q1, Q2 and/or Q3 are independently of one another a group having the formula:

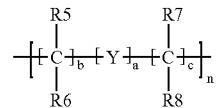

in which:

$5 \geq a+b+c \geq 1$; a=0-5; b=0-5; c=0-5; n=1 or 2. Preferably Q1, Q2 and/or Q3 is defined such that a=b=0, c=1 or 2, and/or n=1. Preferably Q1, Q2 and/or Q3 are independently of one another a group selected from the group consisting of —CH2— and/or —CH2CH2—. Y is independently at each occurrence a group selected from the group consisting of —O—, —S—, —SO—, —SO2-, —C(O)—, arylene, alkylene, heteroarylene, heterocycloalkylene, -(G)P—, —P(O)— and/or -(G)N—, in which G is selected from the group consisting of hydrogen, alkyl, aryl, arylalkyl, cycloalkyl, each, with the exception of hydrogen, can be functionalized by at least one groups E; R5, R6, R7, R8 are independently of one another a group selected from the group consisting of hydrogen, hydroxyl, halogen, —R and/or —OR, in which R is alkyl, alkenyl, cycloalkyl, heterocycloalkyl, aryl, heteroaryl or a carbonyl derivative group, R can be functionalized by at least one groups E, or R5 together with R6, or R7 together with R8, or both, is oxygen, or R5 together with R7 and/or independently R6 together with R8, or R5 together with R8 and/or independently R6 together with R7 is C1-6 alkylene, optionally substituted by C1-4 alkyl, —F, —Cl, —Br or —I; and/or E is independently at each occurrence a functional group selected from the group consisting of —F, —Cl, —Br, —I, —OH, —OR', $NH_2$, —NHR', —N(R')$_2$, —N(R')$_3^+$, —C(O)R', —OC(O)R', —COOH, —COO—(Na$^+$, K$^+$), —COOR', —C(O)NH$_2$, —C(O)NHR', —C(O)N(R')$_2$, heteroaryl, —R', —SR', —SH, —P(R')$_2$, —P(O)(R')$_2$—P(O)(OH)$_2$, —P(O)(OR')$_2$, —NO$_2$, —SO$_3$H, —SO$_3$—(Na$^+$, K$^+$)—S(O)$_2$R', —NHC(O)R', and/or —N(R')C(O)R' in which R' is cycloalkyl, aryl, arylalkyl, or alkyl optionally substituted by —F, —Cl, —Br, —I, —NH$_3^+$, —SO$_3$H, —SO$_3$—(Na$^+$, K$^+$), —COOH, —COO—(Na$^+$,K$^+$), —P(O)(OH)$_2$ or —P(O)(O—(Na$^+$,K$^+$))$_2$.

Preference is given to ligands as indicated above with Z1, Z2 and/or Z, which independently of one another are coordinating group, selected from the group consisting of optionally substituted pyridin-2-yl, optionally substituted imidazol-2-yl, optionally substituted imidazol-4-yl, optionally substituted pyrazol-1-yl, and/or optionally substituted quinolin-2-yl. Greater preference is given to ligands as indicated above with Z1, Z1 and/or Z3 containing optionally substituted pyridin-2-yl groups. Most preferred are the following ligands L comprising tris(pyridin-2-ylmethyl)amine, tris(3-methylpyridin-2-ylmethyl)amine, tris(5-methyl-pyridin-2-ylmethyl)amine, and/or tris(6-methylpyridin-2-ylmethyl)amine.

The correspondingly suitable complex is indicated below:

preferably:

M is a metal selected from the group consisting of Mn(II)-(III)-(IV)-(V), Cu(I)-(II)-(III), Fe(II)-(III)-(IV)-(V), Co(I)-(II)-(III), Ti(II)-(III)-(IV), V(II)-(III)-(IV)-(V), Mo(II)-(III)-(IV)-(V)-(VI) and/or W(IV)-(V)-(VI);

X is a coordinating atom/molecule selected from the group consisting of any mono, bi or tri-chargeontheanion and/or any neutral molecule that is suitable for the mono, bi or tridentate coordination of metal;

Y is any noncoordinating counterion;

a is an integer of between 1 to 10;

k is an integer of between 1 to 10;

n is an integer of between 1 to 10;

m is zero or an integer of between 1 to 20.

With maximum preference the bleach complex which can be used in accordance with the invention and is bonded covalently to a support via at least one ligand is selected from the group consisting of dimanganese tris-μ-oxobis(1,4,7-trimethyl-1,4,7-triazacyclononane)bis(hexafluorophosphate), dimanganese bis-μ-oxo-μ-acetato-1,2-bis(4,7-dimethyl-1,4,7-triaza-1-cyclononyl)ethane bis (hexafluorophosphates), iron N,N'-bis(pyridin-2-ylmethylene)-1,1,-bis(pyridin-2-yl)aminoethane bischloride, cobalt pentamine-μ-acetate dichloride, iron (N-methyl-N,N',N'-tris(3-methylpyridin-2-ylmethyl)ethylenediamine)chloride hexafluorophosphate and/or mixtures thereof.

Bleach complexes with macrocyclic structure which can be used suitably and can be bonded covalently to a support via at least one ligand are additionally described in EP-A-408 131, EP-A-384503, EP-A-458 398, U.S. Pat. No. 5,194,416, WO 96/06157 and/or WO 98/39405, hereby incorporated in full by reference. Further bleach complexes which can be used suitably and can be bonded covalently to a support via at least one ligand, having a linear structure, are described in EP-A-392592, WO 97/48710, U.S. Pat. No. 5,580,485 and/or EP-909 809. U.S. Pat. No. 5,705, hereby incorporated in their entirety by reference.

The invention further provides compositions, particularly detergents, cleaning products and disinfectants, which comprise an abovementioned transition metal bleaching catalyst with an aforedescribed ligand and provides a process for the activation of peroxygen compounds using such a bleaching catalyst support-fixed via such a ligand. The compositions may also be in portion form, i.e., already separately preportioned for the customary use quantity.

In the context of the process of the invention and of a use in accordance with the invention it is possible for the support-fixed bleaching catalyst to be used in the sense of a catalyst wherever the critical factor is a bleaching action which is gentle to the material; for example, in the bleaching of textiles or hair, in the oxidation of organic or inorganic intermediates, and in disinfection.

The use in accordance with the invention consists essentially in creating conditions under which the peroxygen compound and the support-fixed bleaching catalyst can react with one another with the objective of obtaining following-on products which have a more strongly oxidizing action. Such conditions are present in particular when the two reactants meet one another in aqueous solution. This can occur as a result of separate addition of the peroxygen compound and of the support-fixed bleaching catalyst to a solution containing, if desired, detergent or cleaning product. With particular advantage, however, the process of the invention is carried out using a detergent, cleaning product or disinfectant of the invention that comprises the support-fixed bleaching catalyst and, if desired, a peroxide-type oxidizing agent. The peroxygen compound can also be added separately to the solution, as the plain substance or as a preferably aqueous solution or suspension, if a peroxygen-free composition is used.

The conditions can vary widely according to the intended use. For instance, not only purely aqueous solutions but also mixtures of water and suitable organic solvents constitute a suitable reaction medium. The amounts of peroxygen compounds used are generally chosen so that in the solutions there are between 10 ppm and 10% of active oxygen, preferably between 50 and 5000 ppm of active oxygen. The amount of support-fixed bleaching catalyst, based on the bleaching catalyst without support, is also dependent on the intended use. Depending on the desired degree of activation use is made of from 0.00001 mol to 0.025 mol, preferably from 0.0001 mol to 0.002 mol, of catalyst per mole of peroxygen compound, although it is also possible to go below or beyond these limits in particular cases.

A detergent, cleaning product or disinfectant of the invention comprises—the % by weight being based on the bleaching catalyst without support—preferably from 0.0025% by weight to 0.25% by weight, in particular from 0.01% by weight to 0.1% by weight, of the bleaching catalyst. Preferably such detergents, cleaning products or disinfectants of the invention comprise bleaching catalyst(s) with ligand(s) of formula I or II in addition to customary ingredients compatible with the bleaching catalyst.

The support-fixed bleaching catalyst can be embedded in coating substances and/or adsorbed on carrier materials in a manner which is known in principle.

The detergents, cleaning products and disinfectants of the invention, which may be present in the form in particular of pulverulent solids, in aftercompacted particle form, as homogeneous solutions or suspensions, may in addition to the support-fixed bleaching catalyst, used in accordance with the invention, in principle comprise any ingredients which are known and are customary in such compositions. The compositions of the invention may comprise anionic surfactants, cationic surfactants, amphoteric surfactants, builder substances, bleaches, bleach activators, bleach stabilizers, further bleaching catalysts, enzymes, polymers, cobuilders, alkalizing agents, acidifying agents, antiredeposition agents, silver protectants, colorants, optical brighteners, UV stabilizers, fabric softeners, fragrances, soil repellents, anticrease substances, antibacterial substances, color protectants, discoloration inhibitors, vitamins, phyllosilicates, odor-complexing substances, rinse aid, foam inhibitors, foaming agents, preservatives and/or auxiliaries.

Preferably the compositions of the invention comprise, in particular, builder substances, surface-active surfactants, organic and/or inorganic peroxygen compounds, water-miscible organic solvents, enzymes, sequestrants, electrolytes, pH regulators and further auxiliaries, such as optical brighteners, graying inhibitors, dye transfer inhibitors, foam regulators, additional peroxygen activators, dyes and fragrances.

In order to strengthen the disinfection effect toward specific germs, a disinfectant of the invention may comprise customary active antimicrobial substances in addition to the ingredients mentioned so far. Antimicrobial additives of this kind are preferably present in the disinfectants of the invention at not more than 10% by weight, with particular preference from 0.1% by weight to 5% by weight.

In addition to the transition metal bleaching catalysts with the aforedescribed ligands, in particular in combination with inorganic peroxygen compounds, it is possible in the compositions to use conventional bleach activators, in other words compounds which under perhydrolysis conditions give rise to unsubstituted or substituted perbenzoic acid and/or aliphatic peroxycarboxylic acids having 1 to 10 carbon atoms, especially 2 to 4 carbon atoms.

Surfactant(s) which can be used in the composition(s) of the invention comprise anionic, nonionic, cationic and/or amphoteric surfactants. Preference is given from a performance standpoint in the case of laundry detergents to mixtures of anionic and nonionic surfactants, in which case the fraction of the anionic surfactants ought to be greater than the fraction of nonionic surfactants. The total surfactant content of the composition, in the case for example of a washing, care or cleaning product composition, is preferably below 30% by weight, based on the overall composition.

Nonionic surfactants used are preferably alkoxylated, advantageously ethoxylated, in particular primary alcohols having preferably 8 to 18 carbon atoms and on average 1 to 12 mol of ethylene oxide (EO) per mole of alcohol, in which the alcohol radical may be linear or preferably methyl-branched in the 2 position, or may contain linear and methyl-branched radicals in the mixture, as are usually present in oxo alcohol radicals. In particular, however, preference is given to alcohol ethoxylates with linear radicals of alcohols of natural origin having 12 to 18 carbon atoms, e.g. from coconut alcohol, palm alcohol, tallow fatty alcohol or oleyl alcohol, and on average 2 to 8 EO per mole of alcohol. Preferred ethoxylated alcohols include, for example, $C_{12-14}$-alcohols with 3 EO, 4 EO or 7 EO, $C_{9-11}$-alcohol with 7 EO, $C_{13-15}$-alcohols with 3 EO, 5 EO, 7 EO or 8 EO, $C_{12-18}$-alcohols with 3 EO, 5 EO or 7 EO and mixtures of these, such as mixtures of $C_{12-14}$-alcohol with 3 EO and $C_{12-18}$-alcohol with 7 EO. The stated degrees of ethoxylation represent statistical average values which, for a specific product, may be an integer or a fraction. Preferred alcohol ethoxylates have a narrowed homolog distribution (narrow range ethoxylates, NRE). In addition to these nonionic surfactants, it is also possible to use fatty alcohols with more than 12 EO. Examples thereof are tallow fatty alcohol with 14 EO, 25 EO, 30 EO or 40 EO. Nonionic surfactants which contain EO and PO groups together in the molecule can also be used according to the invention. In this connection, it is possible to use block copolymers with EO-PO block units or PO-EO block units, but also EO-PO-EO copolymers and PO-EO-PO copolymers. It is of course also possible to use mixed alkoxylated nonionic surfactants in which EO and PO units are distributed not blockwise, but randomly. Such products are obtainable by simultaneous action of ethylene oxide and propylene oxide on fatty alcohols.

Furthermore, further nonionic surfactants which may be used are also alkyl glycosides of the general formula $RO(G)_x$, in which R is a primary straight-chain or methyl-branched, in particular methyl-branched in the 2 position, aliphatic radical having 8 to 22, preferably 12 to 18, carbon atoms, and G is the symbol which stands for a glycose unit having 5 or 6 carbon atoms, preferably glucose. The degree of oligomerization x, which indicates the distribution of monoglycosides and oligoglycosides, is any desired number between 1 and 10; preferably x is 1.2 to 1.4.

A further class of preferably used nonionic surfactants, which are used either as the sole nonionic surfactant or in combination with other nonionic surfactants, are alkoxylated, preferably ethoxylated or ethoxylated and propoxylated fatty acid alkyl esters, preferably having 1 to 4 carbon atoms in the alkyl chain, in particular fatty acid methyl esters.

Nonionic surfactants of the amine oxide type, for example N-cocoalkyl-N,N-dimethylamine oxide and N-tallow-alkyl-N,N-dihydroxyethylamine oxide, and of the fatty acid alkanolamide type, may also be suitable. The amount of these nonionic surfactants is preferably not more than that of the ethoxylated fatty alcohols, in particular not more than half thereof.

Further suitable surfactants are polyhydroxy fatty acid amides of the formula (TI),

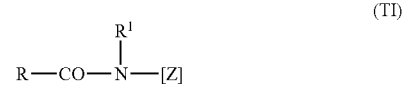

(TI)

in which RCO is an aliphatic acyl radical having 6 to 22 carbon atoms, $R^1$ is hydrogen, an alkyl or hydroxyalkyl radical having 1 to 4 carbon atoms and [Z] is a linear or branched polyhydroxyalkyl radical having 3 to 10 carbon atoms and 3 to 10 hydroxyl groups. The polyhydroxy fatty acid amides are known substances which are customarily obtained by reductive amination of a reducing sugar with ammonia, an alkylamine or an alkanolamine, and subsequent acylation with a fatty acid, a fatty acid alkyl ester or a fatty acid chloride.

The group of the polyhydroxy fatty acid amides also includes compounds of the formula (TII),

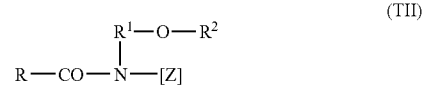

(TII)

in which R is a linear or branched alkyl or alkenyl radical having 7 to 12 carbon atoms, $R^1$ is a linear, branched or cyclic alkyl radical or an aryl radical having 2 to 8 carbon atoms, and $R^2$ is a linear, branched or cyclic alkyl radical or an aryl radical or an oxy-alkyl radical having 1 to 8 carbon atoms, where $C_{1-4}$-alkyl or phenyl radicals are preferred and [Z] is a linear polyhydroxyalkyl radical whose alkyl chain is substituted by at least two hydroxyl groups, or alkoxylated, preferably ethoxylated or propoxylated derivatives of this radical.

[Z] is preferably obtained by reductive amination of a sugar, for example glucose, fructose, maltose, lactose, galactose, mannose or xylose. The N-alkoxy- or N-aryloxy-substituted compounds may then be converted into the desired polyhydroxy fatty acid amides by reaction with fatty acid methyl esters in the presence of an alkoxide as catalyst.

The content of nonionic surfactants in preferred washing, rinsing or cleaning product compositions in portions according to the invention suitable for textile washing is 5 to 20% by weight, preferably 7 to 15% by weight and in particular 9 to 14% by weight, in each case based on the total product.

In machine dishwashing products, preference is given to using low-foaming nonionic surfactants. Machine dishwashing products according to the invention advantageously comprise a nonionic surfactant which has a melting point above room temperature. Accordingly, preferred products are characterized in that they comprise nonionic surfactant(s) with a melting point above 20° C., preferably above 25° C., particularly preferably between 25 and 60° C. and in particular between 26.6 and 43.3° C.

Suitable nonionic surfactants which have melting points or softening points within the stated temperature range are, for example, low-foaming nonionic surfactants which may be solid or highly viscous at room temperature. If nonionic surfactants which are highly viscous at room temperature are used, then it is preferred that they have a viscosity above 20 Pas, preferably above 35 Pas and in particular above 40 Pas. Nonionic surfactants which have a wax-like consistency at room temperature are also preferred.

Preferred nonionic surfactants that are solid at room temperature originate from the groups of alkoxylated nonionic surfactants, in particular ethoxylated primary alcohols and mixtures of these surfactants with surfactants of more complex structure, such as polyoxypropylene/polyoxyethylene/polyoxypropylene (PO/EO/PO) surfactants. Such (PO/EO/PO) nonionic surfactants are characterized, moreover, by good foam control.

In a preferred embodiment of the present invention, the nonionic surfactant with a melting point above room temperature is an ethoxylated nonionic surfactant originating from the reaction of monohydroxyalkanol or alkylphenol having 6 to 20 carbon atoms with preferably at least 12 mol, particularly preferably at least 15 mol, in particular at least 20 mol, of ethylene oxide per mole of alcohol or alkylphenol.

A particularly preferred nonionic surfactant that is solid at room temperature is obtained from a straight-chain fatty alcohol having 16 to 20 carbon atoms ($C_{16-20}$-alcohol), preferably a $C_{18}$-alcohol and at least 12 mol, preferably at least 15 mol and in particular at least 20 mol, of ethylene oxide. Of these, the so-called "narrow range ethoxylates" (see above) are particularly preferred.

Accordingly, particularly preferred products according to the invention comprise ethoxylated nonionic surfactant(s) which has/have been obtained from $C_{6-20}$-monohydroxyalkanols or $C_{6-20}$-alkylphenols or $C_{16-20}$-fatty alcohols and more than 12 mol, preferably more than 15 mol and in particular more than 20 mol, of ethylene oxide per mole of alcohol.

The nonionic surfactant preferably additionally has propylene oxide units in the molecule. Preferably, such PO units account for up to 25% by weight, particularly preferably up to 20% by weight and in particular up to 15% by weight, of the overall molar mass of the nonionic surfactant. Particularly preferred nonionic surfactants are ethoxylated monohydroxyalkanols or alkylphenols which additionally have polyoxyethylene-polyoxypropylene block copolymer units. The alcohol or alkylphenol moiety of such nonionic surfactant molecules constitutes preferably more than 30% by weight, particularly preferably more than 50% by weight and in particular more than 70% by weight, of the total molar mass of such nonionic surfactants. Preferred rinse aids are characterized in that they comprise ethoxylated and propoxylated nonionic surfactants in which the propylene oxide units in the molecule constitute up to 25% by weight, preferably up to 20% by weight and in particular up to 15% by weight, of the total molar mass of the nonionic surfactant.

Further particularly preferred nonionic surfactants with melting points above room temperature comprise 40 to 70% of a polyoxypropylene/polyoxyethylene/polyoxypropylene block polymer blend which 75% by weight of an inverted block copolymer of polyoxyethylene and polyoxypropylene with 17 mol of ethylene oxide and 44 mol of propylene oxide and 25% by weight of a block copolymer of polyoxyethylene and polyoxypropylene, initiated with trimethylolpropane and comprising 24 mol of ethylene oxide and 99 mol of propylene oxide per mole of trimethylolpropane.

Nonionic surfactants which may be used with particular preference are available, for example, under the name Poly Tergent® SLF-18 from Olin Chemicals.

A further preferred washing, rinsing or cleaning product in portions according to the invention comprises nonionic surfactants of the formula $$R^1O[CH_2CH(CH_3)O]_x[CH_2CH_2O]_y[CH_2CH(OH)R^2],$$

in which $R^1$ is a linear or branched aliphatic hydrocarbon radical having 4 to 18 carbon atoms or mixtures thereof, $R^2$ is a linear or branched hydrocarbon radical having 2 to 26 carbon atoms or mixtures thereof, and x is values between 0.5 and 1.5, and y is a value of at least 15.

Further preferred nonionic surfactants are the terminally capped poly(oxyalkylated) nonionic surfactants of the formula $$R^1O[CH_2CH(R^3)O]_x[CH_2]_kCH(OH)[CHO_2]_jOR^2$$

in which $R^1$ and $R^2$ are linear or branched, saturated or unsaturated, aliphatic or aromatic hydrocarbon radicals having 1 to 30 carbon atoms, $R^3$ is H or a methyl, ethyl, n-propyl, isopropyl, n-butyl, 2-butyl or 2-methyl-2-butyl radical, x is values between 1 and 30, k and j represent values between 1 and 12, preferably between 1 and 5. If the value x is $\geq 2$, each $R^3$ in the above formula may be different. $R^1$ and $R^2$ are preferably linear or branched, saturated or unsaturated, aliphatic or aromatic hydrocarbon radicals having 6 to 22 carbon atoms, radicals having 8 to 18 carbon atoms being particularly preferred. For the radical $R^3$, H, —$CH_3$ or —$CH_2CH_3$ are particularly preferred. Particularly preferred values for x are in the range from 1 to 20, in particular from 6 to 15.

As described above, each $R^3$ in the above formula may be different if x is $\geq 2$. By this means it is possible to vary the alkylene oxide unit in the square brackets. If x, for example, is 3, the radical $R^3$ may be chosen in order to form ethylene oxide ($R^3$=H) or propylene oxide ($R^3$=$CH_3$) units, which may be added onto one another in any sequence, for example (EO)(PO)(EO), (EO)(EO)(PO), (EO)(EO)(EO), (PO)(EO)(PO), (PO)(PO)(EO) and (PO)(PO)(PO). The value 3 for x has been chosen here by way of example and it is entirely possible for it to be larger, the scope of variation increasing with increasing values of x and embracing, for example, a large number of (EO) groups, combined with a small number of (PO) groups, or vice versa.

Particularly preferred terminally capped poly(oxyalkylated) alcohols of the above formula have values of k=1 and j=1, thereby simplifying the above formula to $$R^1O[CH_2CH(R^3)O]_xCH_2CH(OH)CH_2OR^2$$

In the last-mentioned formula, $R^1$, $R^2$ and $R^3$ are as defined above and x stands for numbers from 1 to 30, preferably from 1 to 20 and in particular from 6 to 18. Particular preference is given to surfactants in which the radicals $R^1$ and $R^2$ have 9 to 14 carbon atoms, $R^3$ is H, and x assumes values from 6 to 15.

Summarizing the statements given last, preference is given to washing, rinsing or cleaning products according to the invention which contain terminally capped poly(oxyalkylated) nonionic surfactants of the formula $$R^1O[CH_2CH(R^3)O]_x[CH_2]_kCH(OH)[CH_2]_jOR^2$$

in which $R^1$ and $R^2$ are linear or branched, saturated or unsaturated, aliphatic or aromatic hydrocarbon radicals having 1 to 30 carbon atoms, $R^3$ is H or a methyl, ethyl, n-propyl, isopropyl, n-butyl, 2-butyl or 2-methyl-2-butyl radical, x is values between 1 and 30, k and j are values between 1 and 12, preferably between 1 and 5, where surfactants of the type $$R^1O[CH_2CH(R^3)O]_xCH_2CH(OH)CH_2OR^2$$

in which x represents numbers from 1 to 30, preferably from 1 to 20 and in particular from 6 to 18, are particularly preferred.

Anionic, cationic and/or amphoteric surfactants can also be used in conjunction with said surfactants; due to their foaming behavior in machine dishwashing products, they are only of minor importance and are mostly used only in amounts below 10% by weight, in most cases even below 5% by weight, for example from 0.01 to 2.5% by weight, in each case based on the product. The compositions according to the invention can thus also comprise anionic, cationic and/or amphoteric surfactants as surfactant component.

As cationic active substances, the compositions according to the invention can, for example, comprise cationic compounds of the formulae (TIII), (TIV) or (TV):

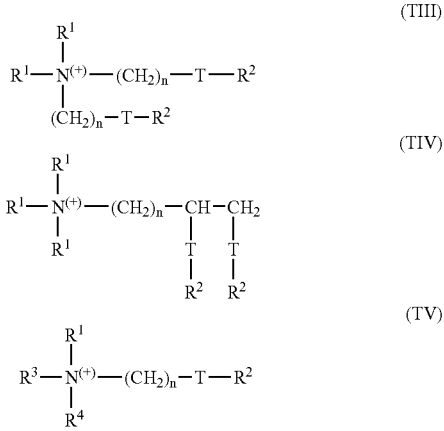

in which each group $R^1$, independently of the others, is chosen from $C_{1-6}$-alkyl, -alkenyl or -hydroxyalkyl groups; each group $R^2$, independently of the others, is chosen from $C_{8-28}$-alkyl or -alkenyl groups; $R^3=R^1$ or $(CH_2)_n$-T-$R^2$; $R^4=R^1$ or $R^2$ or $(CH_2)_n$-T-$R^2$; T=—$CH_2$—, —O—CO— or —CO—O— and n is an integer from 0 to 5.

Anionic surfactants used are, for example, those of the sulfonate and sulfate type. Suitable surfactants of the sulfonate type are preferably $C_{9-13}$-alkylbenzenesulfonates, olefinsulfonates, i.e. mixtures of alkene- and hydroxyalkanesulfonates, and disulfonates, as are obtained, for example, from $C_{12-18}$ monoolefins with terminal or internal double bond by sulfonation with gaseous sulfur trioxide and subsequent alkaline or acidic hydrolysis of the sulfonation products. Also suitable are alkanesulfonates which are obtained from $C_{12-18}$ alkanes, for example by sulfochlorination or sulfoxidation with subsequent hydrolysis or neutralization, respectively. The esters of α-sulfo fatty acids (ester sulfonates), e.g., the α-sulfonated methyl esters of hydrogenated coconut, palm kernel or tallow fatty acids, are also likewise suitable.

Further suitable anionic surfactants are sulfated fatty acid glycerol esters. Fatty acid glycerol esters are understood as meaning the mono-, di- and triesters, and mixtures thereof, as are obtained in the preparation by esterification of a monoglycerol with 1 to 3 mol of fatty acid or in the transesterification of triglycerides with 0.3 to 2 mol of glycerol. Preferred sulfated fatty acid glyceryl esters here are the sulfation products of saturated fatty acids having 6 to 22 carbon atoms, for example of caproic acid, caprylic acid, capric acid, myristic acid, lauric acid, palmitic acid, stearic acid or behenic acid.

Preferred alk(en)yl sulfates are the alkali metal, and in particular the sodium, salts of the sulfuric mono-esters of $C_{12}$-$C_{18}$ fatty alcohols, for example from coconut fatty alcohol, tallow fatty alcohol, lauryl alcohol, myristyl alcohol, cetyl alcohol or stearyl alcohol or of $C_{10}$-$C_{20}$ oxo alcohols and those mono-esters of secondary alcohols with this chain length. In addition, preference is given to alk(en)yl sulfates of stated chain length which contain a synthetic straight-chain alkyl radical prepared on a petrochemical basis and which have analogous degradation behavior to the equivalent compounds based on fatty chemical raw materials. From the point of view of washing, preference is given to the $C_{12}$-$C_{16}$-alkyl sulfates and $C_{12}$-$C_{15}$-alkyl sulfates, and to $C_{14}$-$C_{15}$-alkyl sulfates. 2,3-Alkyl sulfates, which are prepared, for example, in accordance with U.S. Pat. Nos. 3,234,258 or 5,075,041 and can be obtained as commercial products from Shell Oil Company under the name DAN®, are also suitable anionic surfactants.

The sulfuric monoesters of straight-chain or branched $C_7$-$C_{21}$ alcohols ethoxylated with 1 to 6 mol of ethylene oxide, such as 2-methyl-branched $C_9$-$C_{11}$ alcohols having on average 3.5 mol of ethylene oxide (EO) or $C_{12}$-$C_{18}$ fatty alcohols having 1 to 4 EO, are also suitable. Due to their high foaming behavior, they are used in cleaning products only in relatively small amounts, for example in amounts of from 1 to 5% by weight.

Further suitable anionic surfactants are also the salts of alkylsulfosuccinic acid, which are also referred to as sulfosuccinates or as sulfosuccinic esters, and which represent monoesters and/or diesters of sulfosuccinic acid with alcohols, preferably fatty alcohols and in particular ethoxylated fatty alcohols. Preferred sulfosuccinates contain $C_{8-18}$ fatty alcohol radicals or mixtures of these. Particularly preferred sulfosuccinates contain a fatty alcohol radical derived from ethoxylated fatty alcohols which, viewed per se, represent nonionic surfactants (description see below). In this connection, particular preference is in turn given to sulfosuccinates whose fatty alcohol radicals are derived from ethoxylated fatty alcohols with a narrowed homolog distribution. It is likewise also possible to use alk(en)ylsuccinic acid having preferably 8 to 18 carbon atoms in the alk(en)yl chain or salts thereof.

Suitable further anionic surfactants are, in particular, soaps. Saturated and unsaturated fatty acid soaps, such as the salts of lauric acid, myristic acid, palmitic acid, stearic acid, (hydrogenated) erucic acid and behenic acid, and in particular soap mixtures derived from natural fatty acids, e.g. coconut, palm kernel, olive oil or tallow fatty acids, are suitable.

The anionic surfactants including the soaps can be present in the form of their sodium, potassium or ammonium salts, and also in the form of soluble salts of organic bases, such as mono-, di- or triethanolamine. The anionic surfactants are preferably present in the form of their sodium or potassium salts, in particular in the form of the sodium salts.

The content of anionic surfactants in preferred textile washing products according to the invention is 5 to 25% by weight, preferably 7 to 22% by weight and in particular 10 to 20% by weight, in each case based on the total product.

For the purposes of the present invention, preferred products additionally comprise one or more substances from the group of builders, bleaches, bleach activators, enzymes, electrolytes, nonaqueous solvents, pH extenders, fragrances, perfume carriers, fluorescent agents, dyes, hydrotopes, foam inhibitors, silicone oils, anti-redeposition agents, optical brighteners, graying inhibitors, shrink preventatives, anticrease agents, dye-transfer inhibitors, antimicrobial active ingredients, germicides, fungicides, antioxidants, corrosion inhibitors, antistats, easy-iron agents, repellant and impregnation agents, swelling and nonslip agents, and UV absorbers.

Builders which may be present in the products according to the invention are, in particular phosphates, silicates, aluminum silicates (in particular zeolites), carbonates, salts of organic di- and polycarboxylic acids, and mixtures of these substances.

The use of the generally known phosphates as builder substances is possible according to the invention provided such a use is not to be avoided for ecological reasons. Among the numerous commercially available phosphates, the alkali metal phosphates, particularly preferably pentasodium and pentapotassium triphosphate (sodium or potassium tripolyphosphate), are of greatest importance in the washing and cleaning products industry.

Alkali metal phosphates is the collective term for the alkali metal (especially sodium and potassium) salts of the various phosphoric acids, among which metaphosphoric acids $(HPO_3)_n$ and orthophosphoric acid $H_3PO_4$, in addition to higher molecular weight representatives, may be distinguished. The phosphates combine a number of advantages: they act as alkali carriers, prevent limescale films on machine components, and lime encrustations in fabrics, and additionally contribute to the cleaning performance.

Sodium dihydrogenphosphate, $NaH_2PO_4$, exists as the dihydrate (density 1.91 $gcm^{-3}$, melting point 60°) and as the monohydrate (density 2.04 $gcm^{-3}$). Both salts are white powders of very ready solubility in water which lose the water of crystallization upon heating and undergo transition at 200° C. to the weakly acidic diphosphate (disodium hydrogendiphosphate, $Na_2H_2P_2O_7$), and at the higher temperature to sodium trimetaphosphate $(Na_3P_3O_9)$ and Maddrell's salt (see below). $NaH_2PO_4$ reacts acidically; it is formed if phosphoric acid is adjusted to a pH of 4.5 using sodium hydroxide solution and the slurry is sprayed. Potassium dihydrogenphosphate (primary or monobasic potassium phosphate, potassium biphosphate, KDP), $KH_2PO_4$, is a white salt with a density of 2.33 $gcm^{-3}$, has a melting point of 253° [decomposition with formation of potassium polyphosphate $(KPO_3)_x$] and is readily soluble in water.

Disodium hydrogenphosphate (secondary sodium phosphate), $Na_2HPO_4$, is a colorless crystalline salt which is very readily soluble in water. It exists in anhydrous form and with 2 mol (density 2.066 $gcm^{-3}$, water loss at 95°), 7 mol (density 1.68 $gcm^{-3}$, melting point 48° with loss of 5 $H_2O$) and 12 mol of water (density 1.52 $gcm^{-3}$, melting point 35° with loss of 5 $H_2O$), becomes anhydrous at 100° and, if heated more severely, undergoes transition to the diphosphate $Na_4P_2O_7$. Disodium hydrogenphosphate is prepared by neutralizing phosphoric acid with sodium carbonate solution using phenolphthalein as indicator. Dipotassium hydrogenphosphate (secondary or dibasic potassium phosphate), $K_2HPO_4$, is an amorphous white salt which is readily soluble in water.

Trisodium phosphate, tertiary sodium phosphate, $Na_3PO_4$, are colorless crystals which, in the form of the dodecahydrate, have a density of 1.62 $gcm^{-3}$ and a melting point of 73-76° C. (decomposition), in the form of the decahydrate (corresponding to 19-20% $P_2O_5$) have a melting point of 100° C., and in anhydrous form (corresponding to 39-40% $P_2O_5$) have a density of 2.536 $gcm^{-3}$. Trisodium phosphate is readily soluble in water, with an alkaline reaction, and is prepared by evaporative concentration of a solution of precisely 1 mol of disodium phosphate and 1 mol of NaOH. Tripotassium phosphate (tertiary or tribasic potassium phosphate), $K_3PO_4$, is a white, deliquescent, granular powder of density 2.56 $gcm^{-3}$, has a melting point of 1340° and is readily soluble in water with an alkaline reaction. It is produced, for example, when Thomas slag is heated with charcoal and potassium sulfate. Despite the relatively high price, the more readily soluble and therefore highly active potassium phosphates are frequently preferred in the cleaning products industry over the corresponding sodium compounds.

Tetrasodium diphosphate (sodium pyrophosphate), $Na_4P_2O_7$, exists in anhydrous form (density 2.534 $gcm^{-3}$, melting point 988°, 880° also reported) and in the form of the decahydrate (density 1.815-1.836 $gcm^{-3}$, melting point 94° with loss of water). In the case of substances are colorless crystals which dissolve in water with an alkaline reaction. $Na_4P_2O_7$ is formed when disodium phosphate is heated to >200° or by reacting phosphoric acid with sodium carbonate in stoichiometric ratio and removing the water from the solution by spraying. The decahydrate complexes heavy metal salts and hardness formers and therefore reduces the hardness of water. Potassium diphosphate (potassium pyrophosphate), $K_4P_2O_7$, exists in the form of the trihydrate and is a colorless, hygroscopic powder of density 2.33 $gcm^{-3}$, which is soluble in water, the pH of the 1% strength solution at 25° being 10.4.

Condensation of $NaH_2PO_4$ or of $KH_2PO_4$ gives rise to higher molecular weight sodium and potassium phosphates, among which it is possible to distinguish cyclic representatives, the sodium and potassium metaphosphates, and catenated types, the sodium and potassium polyphosphates. For the latter in particular a large number of names are in use: fused or calcined phosphates, Graham's salt, Kurrol's and Maddrell's salt. All higher sodium and potassium phosphates are referred to collectively as condensed phosphates.

The industrially important pentasodium triphosphate, $Na_5P_3O_{10}$ (sodium tripolyphosphate), is a nonhygroscopic, white, water-soluble salt which is anhydrous or crystallizes with 6 $H_2O$ and has the general formula NaO—[P(O)

(ONa)—O]$_n$—Na where n=3. About 17 g of the salt which is free from water of crystallization dissolve in 100 g of water at room temperature, at 60° about 20 g, at 100° around 32 g; after heating the solution at 100° for two hours, about 8% orthophosphate and 15% diphospate are produced by hydrolysis. For the preparation of pentasodium triphosphate, phosphoric acid is reacted with sodium carbonate solution or sodium hydroxide solution in stoichiometric ratio and water is removed from the solution by spraying. In a similar way to Graham's salt and sodium diphosphate, pentasodium triphosphate dissolves numerous insoluble metal compounds (including lime soaps etc.). Penta-potassium triphosphate, $K_5P_3O_{10}$ (potassium tripolyphosphate), is available commercially, for example, in the form of a 50% strength by weight solution (>23% $P_2O_5$, 25% $K_2O$). The potassium polyphosphates are used widely in the washing and cleaning products industry. There are also sodium potassium tripolyphosphates which can likewise be used for the purposes of the present invention. These are formed, for example, when sodium trimetaphosphate is hydrolyzed with KOH:

$$(NaPO_3)_3 + 2KOH \rightarrow Na_3K_2P_3O_{10} + H_2O$$

These can be used in accordance with the invention in precisely the same way as sodium tripolyphosphate, potassium tripolyphosphate or mixtures thereof; mixtures of sodium tripolyphosphate and sodium potassium tripolyphosphate or mixtures of potassium tripolyphosphate and sodium potassium tripolyphosphate or mixtures of sodium tripolyphosphate and potassium tripolyphosphate and sodium potassium tripolyphosphate can also be used according to the invention.

Suitable crystalline, layered sodium silicates have the general formula $NaMSi_xO_{2x+1} \cdot H_2O$, where M is sodium or hydrogen, x is a number from 1.9 to 4, y is a number from 0 to 20, and preferred values for x are 2, 3 or 4. Preferred crystalline sheet silicates of the given formula are those in which M is sodium and x assumes the values 2 or 3. In particular, both β- and also δ-sodium disilicates $Na_2Si_2O_5 \cdot yH_2O$ are preferred.

It is also possible to use amorphous sodium silicates having an $Na_2O:SiO_2$ modulus of from 1:2 to 1:3.3, preferably from 1:2 to 1:2.8 and in particular from 1:2 to 1:2.6, which are dissolution-delayed and have secondary washing properties. The dissolution delay relative to conventional amorphous sodium silicates may have been brought about in a variety of ways, for example by surface treatment, compounding, compacting or by overdrying. For the purposes of this invention the term "amorphous" is understood as including "X-ray-amorphous". This means that, in X-ray diffraction experiments, the silicates do not yield the sharp X-ray reflections typical of crystalline substances but instead yield at best one or more maxima of the scattered X-radiation, having a width of several degree units of the diffraction angle. However, even particularly good builder properties may result if the silicate particles in electron diffraction experiments yield vague or even sharp diffraction maxima. This is to be interpreted such that the products have microcrystalline regions with a size of from 10 to several hundred nm, values up to a maximum of 50 nm and in particular up to a maximum of 20 nm being preferred. Such so-called X-ray amorphous silicates likewise have delayed dissolution compared with conventional waterglasses. Particular preference is given to compacted amorphous silicates, compounded amorphous silicates and overdried X-ray amorphous silicates.

The finely crystalline synthetic zeolite used, containing bound water, is preferably zeolite A and/or P. Zeolite P is particularly preferably Zeolite MAP® (commercial product from Crosfield). Also suitable, however, are zeolite X, and mixtures of A, X and/or P. A co-crystallizate of zeolite X and zeolite A (about 80% by weight of zeolite X), which is sold by CONDEA Augusta S.p.A. under the trade name VEGOBOND AX® and can be described by the formula $$nNa_2O \cdot (1-n)K_2O \cdot Al_2O_3 \cdot (2-2.5)SiO_2 \cdot (3.5-5.5)H_2O$$

is, for example, also commercially available and preferred for the purposes of the present invention. The zeolite can be used as a spray-dried powder or else as an undried stabilized suspension still moist from its preparation. If the zeolite is used as suspension, this suspension may comprise small additions of nonionic surfactants as stabilizers, for example 1 to 3% by weight, based on zeolite, of ethoxylated $C_{12}$-$C_{18}$-fatty alcohols having 2 to 5 ethylene oxide groups, $C_{12}$-$C_{14}$-fatty alcohols having 4 to 5 ethylene oxide groups or ethoxylated isotridecanols. Suitable zeolites have an average particle size of less than 10 µm (volume distribution; measurement method: Coulter Counter) and preferably contain 18 to 22% by weight, in particular 20 to 22% by weight, of bound water.

Further important builders are, in particular, the carbonates, citrates and silicates. Preference is given to using trisodium citrate and/or pentasodium tripolyphosphate and/or sodium carbonate and/or sodium bicarbonate and/or gluconates and/or silicatic builders from the class of disilicates and/or metasilicates.

Further constituents which may be present are alkali metal carriers. Suitable alkali metal carriers are alkali metal hydroxides, alkali metal carbonates, alkali metal hydrogencarbonates, alkali metal sesquicarbonates, alkali metal silicates, alkali metal metasilicates, and mixtures of said substances, preference being given for the purposes of this invention to the alkali metal carbonates, in particular sodium carbonate, sodium hydrogencarbonate or sodium sesquicarbonate.

Particular preference is given to a builder system comprising a mixture of tripolyphosphate and sodium carbonate.

A builder system comprising a mixture of tripolyphosphate and sodium carbonate and sodium disilicate is likewise particularly preferred.

In addition, further ingredients may be present, preference being given to washing, rinsing or cleaning products according to the invention which additionally comprise one or more substances from the group of acidifying agents, chelate complexing agents or of film-inhibiting polymers.

Possible acidifiers are either inorganic acids or organic acids provided these are compatible with the other ingredients. For reasons of consumer protection and handling safety, the solid mono-, oligo- and polycarboxylic acids in particular can be used. From this group, preference is in turn given to citric acid, tartaric acid, succinic acid, malonic acid, adipic acid, maleic acid, fumaric acid, oxalic acid, and polyacrylic acid. The anhydrides of these acids can also be used as acidifiers, maleic anhydride and succinic anhydride in particular being commercially available. Organic sulfonic acids, such as amidosulfonic acid can likewise be used. A composition which is commercially available and which can likewise preferably be used as acidifier for the purposes of the present invention is Sokalan® DCS (trademark of BASF), a mixture of succinic acid (max. 31% by weight), glutaric acid (max. 50% by weight) and adipic acid (max. 33% by weight).

A further possible group of ingredients are the chelate complexing agents. Chelate complexing agents are substances which form cyclic compounds with metal ions, where a single ligand occupies more than one coordination site on a central atom, i.e. is at least "bidentate". In this case, stretched compounds are thus normally closed by complex formation via an ion to give rings. The number of bonded ligands depends on the coordination number of the central ion.

Chelate complexing agents which are customary and preferred for the purposes of the present invention are, for example, polyoxycarboxylic acids, polyamines, ethylenediaminetetraacetic acid (EDTA) and nitrilotriacetic acid (NTA). Complex-forming polymers, i.e. polymers which carry functional groups either in the main chain itself or laterally relative to it, which can act as ligands and react with suitable metal atoms usually to form chelate complexes, can also be used according to the invention. The polymer-bonded ligands of the resulting metal complexes can originate from just one macromolecule or else belong to different polymer chains. The latter leads to crosslinking of the material, provided the complex-forming polymers have not already been crosslinked beforehand via covalent bonds.

Complexing groups (ligands) of customary complex-forming polymers are iminodiacetic acid, hydroxyquinoline, thiourea, guanidine, dithiocarbamate, hydroxamic acid, amidoxime, aminophosphoric acid, (cycl.) polyamino, mercapto, 1,3-dicarbonyl and crown ether radicals, some of which have very specific activities toward ions of different metals. Basis polymers of many complex-forming polymers, which are also commercially important, are polystyrene, polyacrylates, polyacrylonitriles, polyvinyl alcohols, polyvinylpyridines and polyethylenimines. Natural polymers, such as cellulose, starch or chitin are also complex-forming polymers. Moreover, these may be provided with further ligand functionalities as a result of polymer-analogous modifications.

For the purposes of the present invention, particular preference is given to washing, rinsing or cleaning products which comprise one or more chelate complexing agents from the groups of (i) polycarboxylic acids in which the sum of the carboxyl and optionally hydroxyl groups is at least 5,
(ii) nitrogen-containing mono- or polycarboxylic acids,
(iii) geminal diphosphonic acids,
(iv) aminophosphonic acids,
(v) phosphonopolycarboxylic acids,
(vi) cyclodextrins in amounts above 0.1% by weight, preferably above 0.5% by weight, particularly preferably above 1% by weight and in particular above 2.5% by weight, in each case based on the weight of the dishwasher composition.

For the purposes of the present invention, it is possible to use all complexing agents of the prior art. These may belong to different chemical groups. Preference is given to using the following, individually or in a mixture with one another:

a) polycarboxylic acids in which the sum of the carboxyl and optionally hydroxyl groups is at least 5, such as gluconic acid,
b) nitrogen-containing mono- or polycarboxylic acids, such as ethylenediaminetetraacetic acid (EDTA), N-hydroxyethylethylenediaminetriacetic acid, diethylenetriaminepentaacetic acid, hydroxyethyliminodiacetic acid, nitrilodiacetic acid-3-propionic acid, isoserinediacetic acid, N,N-di(β-hydroxyethyl)glycine, N-(1,2-dicarboxy-2-hydroxyethyl)glycine, N-(1,2-dicarboxy-2-hydroxyethyl) aspartic acid or nitrilotriacetic acid (NTA),
c) geminal diphosphonic acids, such as 1-hydroxyethane-1,1-diphosphonic acid (HEDP), higher homologs thereof having up to 8 carbon atoms, and hydroxy or amino group-containing derivatives thereof and 1-aminoethane-1,1-diphosphonic acid, higher homologs thereof having up to 8 carbon atoms, and hydroxy or amino group-containing derivatives thereof,
d) aminophosphonic acids, such as ethylenediaminetetra (methylenephosphonic acid), diethylenetriaminepenta(methylenephosphonic acid) or nitrilotri(methylenephosphonic acid),
e) phosphonopolycarboxylic acids, such as 2-phosphonobutane-1,2,4-tricarboxylic acid, and
f) cyclodextrins.

For the purposes of this patent application, polycarboxylic acids a) are understood as meaning carboxylic acids—including monocarboxylic acids—in which the sum of carboxyl and the hydroxyl groups present in the molecule is at least 5. Complexing agents from the group of nitrogen-containing polycarboxylic acids, in particular EDTA, are preferred. At the alkaline pH values of the treatment solutions required according to the invention, these complexing agents are at least partially in the form of anions. It is unimportant whether they are introduced in the form of acids or in the form of salts. In the case of using salts, alkali metal, ammonium or alkylammonium salts, in particular sodium salts, are preferred.

Film-inhibiting polymers may likewise be present in the compositions according to the invention. These substances, which may have chemically different structures, originate, for example, from the groups of low molecular weight polyacrylates with molar masses between 1000 and 20 000 daltons, preference being given to polymers with molar masses below 15 000 daltons.

Film-inhibiting polymers may also have cobuilder properties. Organic cobuilders which may be used in the dishwasher detergents according to the invention are, in particular, polycarboxylates/polycarboxylic acids, polymeric polycarboxylates, aspartic acid, polyacetals, dextrins, further organic cobuilders (see below) and phosphonates. These classes of substance are described below.

Organic builder substances which can be used are, for example, the polycarboxylic acids usable in the form of their sodium salts, the term polycarboxylic acids meaning carboxylic acids which carry more than one acid function. Examples of these are citric acid, adipic acid, succinic acid, glutaric acid, malic acid, tartaric acid, maleic acid, fumaric acid, sugar acids, aminocarboxylic acids, nitrilotriacetic acid (NTA), provided such a use is not objectionable on ecological grounds, and mixtures thereof. Preferred salts are the salts of the polycarboxylic acids such as citric acid, adipic acid, succinic acid, glutaric acid, tartaric acid, sugar acids and mixtures thereof.

The acids per se may also be used. In addition to their builder action, the acids typically also have the property of an acidifying component and thus also serve to establish a lower and milder pH of detergents or cleaners. In this connection, particular mention is made of citric acid, succinic acid, glutaric acid, adipic acid, gluconic acid and any mixtures thereof.

Also suitable as builders or film inhibitors are polymeric polycarboxylates; these are, for example, the alkali metal salts of polyacrylic acid or of polymethacrylic acid, for example those having a relative molecular mass of from 500 to 70 000 g/mol.

The molar masses given for polymeric polycarboxylates are, for the purposes of this specification, weight-average molar masses $M_w$ of the respective acid form, determined fundamentally by means of gel permeation chromatography (GPC) using a UV detector. The measurement was made against an external polyacrylic acid standard which, owing to its structural similarity to the polymers under investigation, provides realistic molecular weight values. These figures differ considerably from the molecular weight values obtained using polystyrenesulfonic acids as the standard. The molar masses measured against polystyrenesulfonic acids are usually considerably higher than the molar masses given in this specification.

Suitable polymers are in particular polyacrylates which preferably have a molecular mass of from 500 to 20 000 g/mol. Owing to their superior solubility, preference in this group may be given in turn to the short-chain polyacrylates which have molar masses of from 1000 to 10 000 g/mol and particularly preferably from 1000 to 4000 g/mol.

In the products according to the invention, particular preference is given to using both polyacrylates and also copolymers of unsaturated carboxylic acids, monomers containing sulfonic acid groups, and optionally further ionic or nonionogenic monomers. The copolymers containing sulfonic acid groups are described in detail below.

Also suitable are copolymeric polycarboxylates, in particular those of acrylic acid with methacrylic acid and of acrylic acid or methacrylic acid with maleic acid. Copolymers which have proven to be particularly suitable are those of acrylic acid with maleic acid which contain from 50 to 90% by weight of acrylic acid and 50 to 10% by weight of maleic acid. Their relative molecular mass, based on free acids, is generally 2000 to 70 000 g/mol, preferably 20 000 to 50 000 g/mol and in particular 30 000 to 40 000 g/mol.

The (co)polymeric polycarboxylates can either be used as powder or as aqueous solution. The (co)polymeric polycarboxylate content of the compositions is preferably 0.5 to 20% by weight, in particular 3 to 10% by weight.

Particular preference is also given to biodegradable polymers of more than two different monomer units, for example those which contain, as monomers, salts of acrylic acid or of maleic acid, and vinyl alcohol or vinyl alcohol derivatives, or those which contain, as monomers, salts of acrylic acid and of 2-alkylallylsulfonic acid, and sugar derivatives. Further preferred copolymers are those which preferably have, as monomers, acrolein and acrylic acid/acrylic acid salts or acrolein and vinyl acetate.

Further preferred builder substances which are likewise to be mentioned are polymeric aminodicarboxylic acids, salts thereof or precursor substances thereof. Particular preference is given to polyaspartic acids or salts and derivatives thereof, which also have a bleach-stabilizing effect as well as cobuilder properties.

Further suitable builder substances are polyacetals which can be obtained by reacting dialdehydes with polyolcarboxylic acids which have 5 to 7 carbon atoms and at least 3 hydroxyl groups. Preferred polyacetals are obtained from dialdehydes, such as glyoxal, glutaraldehyde, terephthalaldehyde, and mixtures thereof and from polyolcarboxylic acids, such as gluconic acid and/or glucoheptonic acid.

Further suitable organic builder substances are dextrins, for example oligomers or polymers of carbohydrates, which can be obtained by partial hydrolysis of starches. The hydrolysis can be carried out in accordance with customary processes, for example acid-catalyzed or enzyme-catalyzed processes. The hydrolysis products preferably have average molar masses in the range from 400 to 500 000 g/mol. Preference is given here to a polysaccharide with a dextrose equivalent (DE) in the range from 0.5 to 40, in particular from 2 to 30, where DE is a common measure of the reducing effect of a polysaccharide compared with dextrose, which has a DE of 100. It is also possible to use maltodextrins with a DE between 3 and 20 and dried glucose syrups with a DE between 20 and 37, and also so-called yellow dextrins and white dextrins with relatively high molar masses in the range from 2000 to 30 000 g/mol.

The oxidized derivatives of such dextrins are their reaction products with oxidizing agents which are able to oxidize at least one alcohol function of the saccharide ring to the carboxylic acid function. A product oxidized on the $C_6$ of the saccharide ring may be particularly advantageous.

Oxydisuccinates and other derivatives of disuccinates, preferably ethylenediaminedisuccinate, are also further suitable cobuilders. Here, ethylenediamine N,N'-disuccinate (EDDS) is preferably used in the form of its sodium or magnesium salts. In this connection, preference is also given to glycerol disuccinates and glycerol trisuccinates. Suitable use amounts in zeolite-containing and/or silicate-containing formulations are 3 to 15% by weight.

Further organic cobuilders which can be used are, for example, acetylated hydroxycarboxylic acids or salts thereof, which may optionally also be present in lactone form and which contain at least 4 carbon atoms and at least one hydroxyl group and at most two acid groups.

A further class of substances with cobuilder properties is the phosphonates. These are, in particular, hydroxyalkane- and aminoalkanephosphonates. Among the hydroxyalkanephosphonates, 1-hydroxyethane-1,1-diphosphonate (HEDP) is of particular importance as cobuilder. It is preferably used as the sodium salt, the disodium salt giving a neutral reaction and the tetrasodium salt giving an alkaline reaction (pH 9). Suitable aminoalkanephosphonates are preferably ethylenediaminetetramethylenephosphonate (EDTMP), diethylenetriaminepentamethylenephosphonate (DTPMP) and higher homologs thereof. They are preferably used in the form of the neutrally reacting sodium salts, e.g. as the hexasodium salt of EDTMP or as the hepta- and octasodium salt of DTPMP. Here, preference is given to using HEDP as builder from the class of phosphonates.

In addition, the aminoalkanephosphonates have a marked heavy metal-binding capacity. Accordingly, particularly if the compositions also comprise bleaches, it may be preferable to use aminoalkanephosphonates, in particular DTPMP, or mixtures of said phosphonates.

In addition to the substances from said classes of substances, the products according to the invention can comprise further customary ingredients of washing, rinsing or cleaning products, where bleaches, bleach activators, enzymes, silver protectants, dyes and fragrances are of particular importance. These substances are described below.

Among the compounds which serve as bleaches and liberate $H_2O_2$ in water, sodium perborate tetrahydrate and sodium perborate monohydrate are of particular importance. Examples of further bleaches which may be used are sodium percarbonate, peroxypyrophosphates, citrate perhydrates and $H_2O_2$-supplying peracidic salts or peracids, such as perbenzoates, peroxophthalates, diperazelaic acid, phthaloimino peracid or diperdodecanedioic acid.

In order to achieve an improved bleaching effect during washing at temperatures of 60° C. and below, bleach activators can be incorporated into the washing and cleaning product moldings. Bleach activators which can be used are compounds which, under perhydrolysis conditions, produce aliphatic peroxocarboxylic acids having preferably 1 to 10 carbon atoms, in particular 2 to 4 carbon atoms, and/or optionally substituted perbenzoic acid. Substances which carry O-acyl and/or N-acyl groups of said number of carbon atoms and/or optionally substituted benzoyl groups are suitable. Preference is given to polyacylated alkylenediamines, in particular tetraacetylethylenediamine (TAED), acylated triazine derivatives, in particular 1,5-diacetyl-2,4-dioxohexahydro-1,3,5-triazine (DADHT), acylated glycolurils, in particular tetraacetyl-glycoluril (TAGU), N-acylimides, in particular N-nonanoylsuccinimide (NOSI), acylated phenolsulfonates, in particular n-nonanoyl- or isononanoyloxybenzenesulfonate (n- or iso-NOBS), carboxylic anhydrides, in particular phthalic anhydride, acylated polyhydric alcohols, in particular triacetin, ethylene glycol diacetate and 2,5-diacetoxy-2,5-dihydrofuran.

In addition to the conventional bleach activators, or instead of them, so-called bleaching catalysts may also be used. These substances are bleach-boosting transition metal salts or transition metal complexes, such as, for example, Mn-, Fe-, Co-, Ru- or Mo-salen complexes or -carbonyl complexes. Mn, Fe, Co, Ru, Mo, Ti, V and Cu complexes with N-containing tripod ligands, and Co-, Fe-, Cu- and Ru-ammine complexes can also be used as bleaching catalysts.

Suitable enzymes are, in particular, those from the classes of hydrolases, such as the proteases, esterases, lipases or lipolytic enzymes, amylases, cellulases or other glycosylhydrolases and mixtures of said enzymes. In the washing, all of these hydrolases contribute to the removal of protein-containing, grease-containing or starch-containing stains and graying. Cellulases and other glycosylhydrolases may, furthermore, contribute, by removing pilling and microfibrils, to color retention and to an increase in the softness of the textile. For bleaching and/or for inhibiting color transfer it is also possible to use oxyreductases. Especially suitable enzymatic active ingredients are those obtained from bacterial strains or fungi such as *Bacillus subtilis, Bacillus licheniformis, Streptomyceus griseus* and *Humicola insolens*. Preference is given to using proteases of the subtilisin type, and especially to proteases obtained from *Bacillus lentus*. Of particular interest in this connection are enzyme mixtures, for example of protease and amylase or protease and lipase or lipolytic enzymes or protease and cellulase or of cellulase and lipase or lipolytic enzymes or of protease, amylase and lipase or lipolytic enzymes or protease, lipase or lipolytic enzymes and cellulase, but in particular protease and/or lipase-containing mixtures or mixtures containing lipolytic enzymes. Examples of such lipolytic enzymes are the known cutinases. Peroxidases or oxidases have also proven suitable in some cases. The suitable amylases include, in particular, α-amylases, isoamylases, pullulanases, and pectinases. The cellulases used are preferably cellobiohydrolases, endoglucanases and β-glucosidases, which are also called cellobiases, or mixtures thereof. Because different types of cellulase differ in their CMCase and avicelase activities, specific mixtures of the cellulases may be used to establish the desired activities.

The enzymes can be adsorbed on carrier substances or be embedded in coating substances in order to protect them against premature decomposition. The content of enzymes, enzyme mixtures or enzyme granulates may, for example, be from about 0.1 to 5% by weight, preferably 0.12 to about 2% by weight.

In accordance with the prior art, enzymes are added primarily to a cleaning product formulation, especially to a dishcare composition which is intended for the main wash cycle. A disadvantage in this case was that the activity optimum of enzymes used restricted the choice of temperature and also that problems occurred in connection with the stability of the enzymes in the strongly alkaline medium. With the washing, dishwashing or cleaning product portions of the invention it is possible to introduce enzymes into a separate compartment and then to use enzymes in the prewash cycle as well and so to utilize the prewash cycle, in addition to the main wash cycle, for the enzymes to act on ware soiling.

In accordance with the invention it is particularly preferred to add enzymes to the detersive formulation or subportion—intended for the prewash cycle—of a cleaning product and/or care composition portion and then—with further preference—to enclose such a formulation with a material of a flexible, preferably elastic, hollow body which dissolves in water even at low temperature, in order, for example, to protect the enzyme-containing formulation against a loss of activity caused by immediate-environment conditions. With further preference, the enzymes are optimized for use under the conditions of the prewash cycle, i.e., in cold water, for example.

The cleaning products of the invention may be advantageous when the enzyme formulations are in liquid form, such as are available commercially in some cases, since in that case it is possible to expect a rapid action which takes place as early as in the prewash cycle (which is relatively short and is carried out in cold water). Even when—as is usual—the enzymes are used in solid form and are provided with a hollow body enclosure of a water-soluble material which is soluble even in cold water, the enzymes may develop their activity even before the main wash cycle or main cleaning operation. An advantage of using an enclosure comprising water-soluble material, especially comprising cold-water-soluble material, is that the enzyme(s) acts (act) rapidly in cold water following dissolution of the enclosure. By this means it is possible to extend their activity time, to the benefit of the wash outcome.

The cleaning products according to the invention for machine dishwashing may comprise corrosion inhibitors in order to protect the ware or the machine, particular importance in the field of machine dishwashing being attached to silver protectants. The known substances of the prior art may be used. In general, silver protectants may be chosen particularly from the group of triazoles, benzotriazoles, bisbenzotriazoles, aminotriazoles, alkylaminotriazoles and the transition metal salts or complexes. Particular preference is given to the use of benzotriazole and/or alkylaminotriazole. Frequently encountered in cleaning formulations, moreover, are agents containing active chlorine, which can significantly reduce the corrosion of the silver surface. In chlorine-free cleaners, use is made in particular of oxygen-containing and nitrogen-containing organic redox-active compounds, such as divalent and trivalent phenols, e.g. hydroquinone, pyrocatechol, hydroxyhydroquinone, gallic acid, phloroglucinol, pyrogallol and derivatives of these classes of compounds. Salt-like and complex inorganic compounds, such as salts of the metals Mn, Ti, Zr, Hf, V, Co and Ce also find frequent application. Preference is given here to the transition metal salts chosen from the group of manganese and/or cobalt salts and/or complexes, particularly preferably cobalt (ammine) complexes, cobalt(acetato) complexes, cobalt(carbonyl) complexes, the chlorides of cobalt or of manganese and manganese sulfate. Zinc compounds can likewise be used to prevent corrosion of the ware.

A broad number of highly diverse salts can be used as electrolytes from the group of inorganic salts. Preferred cations are the alkali metal and alkaline earth metals, preferred anions being the halides and sulfates. From a preparation point of view, the use of NaCl or MgCl$_2$ in the products according to the invention is preferred. The content of electrolytes in the products according to the invention is usually 0.5 to 5% by weight.

Nonaqueous solvents which can be used in the products according to the invention originate, for example, from the group of mono- or polyhydric alcohols, alkanolamines or glycol ethers, provided they are miscible with water in the stated concentration range. The solvents are preferably chosen from ethanol, n- or isopropanol, butanols, glycol, propanediol or butanediol, glycerol, diglycol, propyl or butyl diglycol, hexylene glycol, ethylene glycol methyl ether, ethylene glycol ethyl ether, ethylene glycol propyl ether, ethylene glycol mono-n-butyl ether, diethylene glycol methyl ether, diethylene glycol ethyl ether, propylene glycol methyl, ethyl or propyl ether, dipropylene glycol monomethyl or -ethyl ether, diisopropylene glycol monomethyl or monoethyl ether, methoxy, ethoxy or butoxy triglycol, 1-butoxyethoxy-2-propanol, 3-methyl-3-methoxybutanol, propylene-glycol-t-butyl ether, and mixtures of these solvents. Nonaqueous solvents can be used in the liquid detergents according to the invention in amounts between 0.5 and 10% by weight, but preferably less than 5% by weight and in particular less than 3% by weight.

In order to bring the pH of the products according to the invention into the desired range, it is possible to use pH regulators. Use can be made here of any known acids or alkalis, provided their use is not precluded for application or ecological reasons or for reasons of consumer protection. The amount of these regulators does not usually exceed 5% by weight of the total formulation.

In order to improve the esthetic impression of the products according to the invention, they can be colored with suitable dyes. Preferred dyes, the choice of which does not present any problems at all to the person skilled in the art, have high storage stability and high insensitivity toward the other ingredients of the products and toward light, and do not have marked substantivity toward textile fibers so as not to color these.

Suitable foam inhibitors which can be used in the products according to the invention are, for example, soaps, paraffins or silicone oils, which may optionally be applied to carrier materials. Suitable anti-redeposition agents, which are also referred to as soil repellants, are, for example, nonionic cellulose ethers, such as methylcellulose and methylhydroxypropylcellulose with a content of methoxy groups of from 15 to 30% by weight and of hydroxypropyl groups of from 1 to 15% by weight, in each case based on the nonionic cellulose ether, and the polymers, known from the prior art, of phthalic acid and/or terephthalic acid or derivatives thereof, in particular polymers of ethylene terephthalates and/or polyethylene glycol terephthalates or anionically and/or nonionically modified derivatives of these. Of these, particular preference is given to the sulfonated derivatives of phthalic acid and terephthalic acid polymers.

Optical brighteners (so-called "whitening agents") can be added to the products according to the invention in order to eliminate graying and yellowing of the treated textiles. These substances attach to the fibers and bring about a brightening and simulated bleaching action by converting invisible ultraviolet radiation into visible longer-wave length light, the ultraviolet light absorbed from sunlight being irradiated as a pale bluish fluorescence and, together with the yellow shade of the grayed or yellowed laundry, producing pure white. Suitable compounds originate, for example, from the classes of substance of 4,4'-diamino-2,2'-stilbenedisulfonic acids (flavonic acids), 4,4'-distyrylbiphenyls, methylumbelliferones, coumarins, dihydroquinolinones, 1,3-diarylpyrazolines, naphthalimides, benzoxazol, benzisoxazol and benzimidazol systems, and pyrene derivatives substituted by heterocycles. The optical brighteners are usually used in amounts between 0.05 and 0.3% by weight, based on the finished product.

Graying inhibitors have the task of holding the soiling detached from the fiber in suspended form in the liquor, thus preventing the soiling from reattaching. Suitable for this purpose are water-soluble colloids, mostly of an organic nature, for example glue, gelatin, salts of ether sulfonic acids of starch or of cellulose or salts of acidic sulfuric esters of cellulose or of starch. Water-soluble polyamides which contain acidic groups are also suitable for this purpose. In addition, it is possible to use soluble starch preparations, and starch products other than those mentioned above, e.g. degraded starch, aldehyde starches etc. It is also possible to use polyvinylpyrrolidone. Preference is, however, given to using cellulose ethers, such as carboxymethylcellulose (Na salt), methylcellulose, hydroxyalkylcellulose and mixed ethers, such as methylhydroxyethylcellulose, methylhydroxypropylcellulose, methylcarboxymethylcellulose and mixtures thereof in amounts of from 0.1 to 5% by weight, based on the compositions.

If the compositions according to the invention are formulated as products for machine dishwashing, then further ingredients may be used. Dishes which have been washed by machine are nowadays often subject to higher requirements than dishes washed manually. For example, even dishes which have been completely cleaned of food residue will not be evaluated as being perfect if, after machine dishwashing, they still have whitish marks based on water hardness or other mineral salts which, owing to a lack of wetting agents, originate from dried-on water drops. In order to obtain sparkling and stain-free dishes, rinse aids are therefore used nowadays with success. The addition of rinse aid at the end of the wash program ensures that the water runs off from the ware as completely as possible, so that the various surfaces at the end of the wash program are residue-free and flawlessly sparkling. Machine dishwashing in domestic dishwashers usually involves a prewash cycle, a main wash cycle and a clear-rinse cycle, which are interrupted by intermediate rinse cycles. With most machines, the prewash cycle for heavily soiled dishes can be selected, but is only chosen by the consumer in exceptional cases, meaning that in most machines a main wash cycle, an intermediate rinse cycle with clean water and a clear-rinse cycle are carried out. The temperature of the main wash cycle varies between 40 and 65° C. depending on the machine model and program selected. In the clear-rinse cycle, rinse aids, which usually comprise nonionic surfactants as the main constituent, are added from a dosing chamber in the machine. Such rinse aids are in liquid form and are described widely in the prior art. Their task consists primarily in preventing lime marks and films on the dishes.

The compositions according to the invention can be formulated as "normal" cleaners, which are used together with standard commercial supplementing agents (rinse aids, regenerating salt). However, using the compositions according to the invention, it is a particular advantage that the additional dosing of rinse aids can be dispensed with. These so-called "2-in-1" products lead to easier handling and take away from the consumer the burden of additionally dosing two different products (detergent and rinse aid).

Even when using "2-in-1" products, two dosing operations are required at intervals for operating a domestic dishwasher, since the regenerating salt has to be topped up in the water softening system of the machine after a certain number of wash cycles. These water-softening systems consist of ion exchanger polymers which soften the hard water entering the machine and, after the wash program, are regenerated by rinsing with salt water.

However, it is also possible to provide products according to the invention which, being so-called "3 in 1" products, combine the conventional detergent, rinse aid and a salt replacement function.

For the purposes of the present invention, unsaturated carboxylic acids of the formula TVI as monomer can also be added to the composition of the invention,

$$R^1(R^2)C=C(R^3)COOH \qquad (TVI),$$

in which $R^1$ to $R^3$, independently of one another, are —H, —CH$_3$, a straight-chain or branched saturated alkyl radical having 2 to 12 carbon atoms, a straight-chain or branched, mono- or polyunsaturated alkenyl radical having 2 to 12 carbon atoms, alkyl or alkenyl radicals as defined above and substituted by —NH$_2$, —OH or —COOH, or —COOH or —COOR$^4$, where R$^4$ is a saturated or unsaturated, straight-chain or branched hydrocarbon radical having 1 to 12 carbon atoms. Among the unsaturated carboxylic acids which can be described by the formula (TVI), particular preference is given to acrylic acid ($R^1=R^2=R^3=H$), methacrylic acid ($R^1=R^2=H$; $R^3=CH_3$) and/or maleic acid ($R^1=COOH$; $R^2=R^3=H$).

In the case of the monomers containing sulfonic acid groups, preference is given to those of the formula (TVII),

$$R^5(R^6)C=C(R^7)-X-SO_3H \qquad (TVII),$$

in which $R^5$ to $R^7$, independently of one another, are —H, —CH$_3$, a straight-chain or branched saturated alkyl radical having 2 to 12 carbon atoms, a straight-chain or branched, mono- or polyunsaturated alkenyl radical having 2 to 12 carbon atoms, alkyl or alkenyl radicals as defined above and substituted by —NH$_2$, —OH or —COOH, or —COOH or —COOR$^4$, where R$^4$ is a saturated or unsaturated, straight-chain or branched hydrocarbon radical having 1 to 12 carbon atoms, and X is an optionally present spacer group which is chosen from —(CH$_2$)$_n$—, where n=0 to 4, —COO—(CH$_2$)$_k$— where k=1 to 6, —C(O)—NH—C(CH$_3$)$_2$— and —C(O)—NH—CH(CH$_2$CH$_3$)—.

Among these monomers, preference is given to those of the formulae (TVIIa), (TVIIb) and/or (TVIIc),

$$H_2C=CH-X-SO_3H \qquad (TVIIa),$$

$$H_2C=C(CH_3)-X-SO_3H \qquad (TVIIb),$$

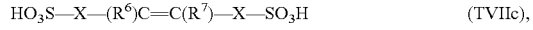
$$HO_3S-X-(R^6)C=C(R^7)-X-SO_3H \qquad (TVIIc),$$

in which $R^6$ and $R^7$, independently of one another, are chosen from —H, —CH$_3$, —CH$_2$CH$_3$, —CH$_2$CH$_2$CH$_3$, —CH(CH$_3$)$_2$ and X is an optionally present spacer group which is chosen from —(CH$_2$)$_n$—, where n=0 to 4, —COO—(CH$_2$)$_k$— where k=1 to 6, —C(O)—NH—C(CH$_3$)$_2$— and —C(O)—NH—(CH$_2$CH$_3$)—.

Particularly preferred monomers containing sulfonic acid groups here are 1-acrylamido-1-propanesulfonic acid (X=—C(O)NH—CH(CH$_2$CH$_3$) in formula (TVIIa), 2-acrylamido-2-propanesulfonic acid (X=—C(O)NH—C(CH$_3$)$_2$ in formula (TVIIa), 2-acrylamido-2-methyl-1-propanesulfonic acid (X=—C(O)NH—C(CH$_3$)$_2$CH$_2$— in formula (TVIIa), 2-methacrylamido-2-methyl-1-propanesulfonic acid (X=—C(O)NH—C(CH$_3$)$_2$CH$_2$— in formula (TVIIb), 3-methacrylamido-2-hydroxypropanesulfonic acid (X=—C(O)NH—CH$_2$CH(OH)CH$_2$— in formula VIIb), allylsulfonic acid (X=CH$_2$ in formula (TVIIa), methallylsulfonic acid (X=CH$_2$ in formula (TVIIb), allyloxybenzenesulfonic acid (X=—CH$_2$—O—C$_6$H$_4$— in formula (TXVIIa), methallyloxybenzenesulfonic acid (X=—CH$_2$—O—C$_6$H$_4$— in formula VIIb), 2-hydroxy-3-(2-propenyloxy)propanesulfonic acid, 2-methyl-2-propene-1-sulfonic acid (X=CH$_2$ in formula (TVIIb), styrenesulfonic acid (X=C$_6$H$_4$ in formula (TVIIa)), vinylsulfonic acid (X not present in formula (TVIIa)), 3-sulfopropyl acrylate (X=—C(O)NH—CH$_2$CH$_2$CH$_2$— in formula (TVIIa), 3-sulfopropyl methacrylate (X=—C(O)NH—CH$_2$CH$_2$CH$_2$— in formula (TVIIb)), sulfomethacrylamide (X=—C(O)NH— in formula (TVIIb)), sulfomethyl methacrylamide (X=—C(O)NH—CH$_2$— in formula (TVIIb)) and water-soluble salts of said acids.

Suitable further ionic or nonionogenic monomers are, in particular, ethylenically unsaturated compounds. Preferably the content of the monomers of group iii) in the polymers used according to the invention is less than 20% by weight, based on the polymer. Polymers to be used with particular preference consist merely of monomers of groups i) and ii).

In summary, copolymers of i) unsaturated carboxylic acids of the formula (TVI)

$$R^1(R^2)C=C(R^3)COOH \qquad (TVI),$$

in which $R^1$ to $R^3$, independently of one another, are —H, —CH$_3$, a straight-chain or branched saturated alkyl radical having 2 to 12 carbon atoms, a straight-chain or branched, mono- or polyunsaturated alkenyl radical having 2 to 12 carbon atoms, alkyl or alkenyl radicals as defined above and substituted by —NH$^2$, —OH or —COOH, or —COOH or —COOR$^4$, where R$^4$ is a saturated or unsaturated, straight-chain or branched hydrocarbon radical having 1 to 12 carbon atoms, ii) monomers of the formula (TVII) containing sulfonic acid groups

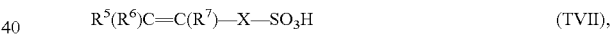
$$R^5(R^6)C=C(R^7)-X-SO_3H \qquad (TVII),$$

in which $R^5$ to $R^7$, independently of one another, are —H, —CH$_3$, a straight-chain or branched saturated alkyl radical having 2 to 12 carbon atoms, a straight-chain or branched, mono- or polyunsaturated alkenyl radical having 2 to 12 carbon atoms, alkyl or alkenyl radicals as defined above and substituted by —NH$_2$, —OH or —COOH, or —COOH or —COOR$^4$, where R$^4$ is a saturated or unsaturated, straight-chain or branched hydrocarbon radical having 1 to 12 carbon atoms, and X is an optionally present spacer group which is chosen from —(CH$_2$)$_n$—, where n=0 to 4, —COO—(CH$_2$)$_k$— where k=1 to 6, —C(O)—NH—C(CH$_3$)$_2$— and —C(O)—NH—CH(CH$_2$CH$_3$)— iii) optionally further ionic or nonionogenic monomers are particularly preferred.

Particularly preferred copolymers consist of i) one or more unsaturated carboxylic acids from the group consisting of acrylic acid, methacrylic acid and/or maleic acid ii) one or more monomers containing sulfonic acid groups and of the formulae (TVIIa), (TVIIb) and/or (TVIIc):

$$H_2C=CH-X-SO_3H \qquad (TVIIa),$$

$$H_2C=C(CH_3)-X-SO_3H \qquad (TVIIb),$$

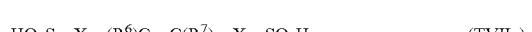
$$HO_3S-X-(R^6)C=C(R^7)-X-SO_3H \qquad (TVIIc),$$

in which $R^6$ and $R^7$, independently of one another, are chosen from —H, —CH$_3$, —CH$_2$CH$_3$, —CH$_2$CH$_2$CH$_3$, —CH(CH$_3$)$_2$ and X is an optionally present spacer group which is chosen from —(CH$_2$)$_n$—, where n=0 to 4, —COO—(CH$_2$)$_k$—, where k=1 to 6, —C(O)—NH—C(CH$_3$)$_2$— and —C(O)—NH—CH(CH$_2$CH$_3$)— iii) optionally further ionic or nonionogenic monomers.

The copolymers present according to the invention in the compositions can comprise the monomers from groups i) and ii), and optionally iii) in varying amounts, where all of the representatives from group i) can be combined with all of the representatives from group ii) and all of the representatives from group iii). Particularly preferred polymers have certain structural units which are described below.

Thus, for example, preference is given to compositions according to the invention which are characterized in that they comprise one or more copolymers which contain structural units of the formula (TVIII)

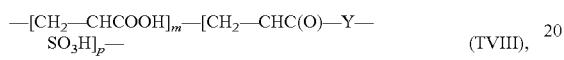  (TVIII), in which m and p are in each case a whole natural number between 1 and 2000, and Y is a spacer group selected from substituted or unsubstituted aliphatic, aromatic or araliphatic hydrocarbon radicals having 1 to 24 carbon atoms, where spacer groups in which Y is —O—(CH$_2$)$_n$—, where n=0 to 4, is —O—(C$_6$H$_4$)—, is —NH—C(CH$_3$)$_2$— or —NH—CH(CH$_2$CH$_3$)— are preferred.

These polymers are prepared by copolymerization of acrylic acid with an acrylic acid derivative containing sulfonic acid groups. Copolymerizing the acrylic acid derivative containing sulfonic acid groups with methacrylic acid leads to another polymer which is likewise used with preference in the compositions according to the invention and is characterized in that the compositions comprise one or more copolymers which contain structural units of the formula (TIX)

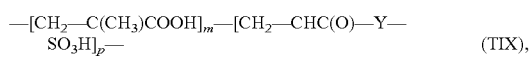  (TIX), in which in and p are in each case a whole natural number between 1 and 2000, and Y is a spacer group which is chosen from substituted or unsubstituted aliphatic, aromatic or araliphatic hydrocarbon radicals having 1 to 24 carbon atoms, where spacer groups in which Y is —O—(CH$_2$)$_n$—, where n=0 to 4, is —O—(C$_6$H$_4$)—, is —NH—C(CH$_3$)$_2$— or —NH—CH(CH$_2$CH$_3$)— are preferred.

Entirely analogously, acrylic acid and/or methacrylic acid can also be copolymerized with methacrylic acid derivatives containing sulfonic acid groups, as a result of which the structural units in the molecule are changed. For example, compositions according to the invention which comprise one or more copolymers which contain structural units of the formula (TX)

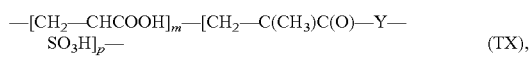  (TX), in which m and p are in each case a whole natural number between 1 and 2000, and Y is a spacer group which is selected from substituted or unsubstituted aliphatic, aromatic or araliphatic hydrocarbon radicals having 1 to 24 carbon atoms, where spacer groups in which Y is —O—(CH$_2$)$_n$—, where n=0 to 4, is —O—(C$_6$H$_4$)—, is —NH—C(CH$_3$)$_2$— or —NH—CH(CH$_2$CH$_3$)— are preferred, are likewise a preferred embodiment of the present invention, just as preference is also given to compositions which are characterized in that they comprise one or more copolymers which contain structural units of the formula (TXI)

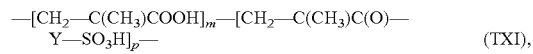  (TXI), in which m and p are in each case a whole natural number between 1 and 2000, and Y is a spacer group which is selected from substituted or unsubstituted aliphatic, aromatic or araliphatic hydrocarbon radicals having 1 to 24 carbon atoms, where spacer groups in which Y is —O—(CH$_2$)$_n$—, where n=0 to 4, is —O—(C$_6$H$_4$)—, is —NH—C(CH$_3$)$_2$— or —NH—CH(CH$_2$CH$_3$)— are preferred.

In lieu of acrylic acid and/or methacrylic acid, or in addition thereto, it is also possible to use maleic acid as particularly preferred monomer from group i). This gives compositions preferred according to the invention which are characterized in that they comprise one or more copolymers which contain structural units of the formula (TXI)

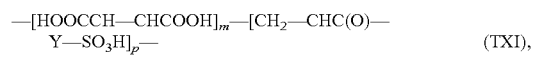  (TXI), in which m and p are in each case a whole natural number between 1 and 2000, and Y is a spacer group which is chosen from substituted or unsubstituted aliphatic, aromatic or araliphatic hydrocarbon radicals having 1 to 24 carbon atoms, where spacer groups in which Y is —O— (CH$_2$)$_n$—, where n=0 to 4, is —O—(C$_6$H$_4$)—, is —NH—C(CH$_3$)$_2$— or —NH—CH(CH$_2$CH$_3$)— are preferred, and gives compositions which are characterized in that they comprise one or more copolymers which contain structural units of the formula (XII)

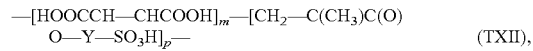  (TXII), in which m and p are in each case a whole natural number between 1 and 2000, and Y is a spacer group which is selected from substituted or unsubstituted aliphatic, aromatic or araliphatic hydrocarbon radicals having 1 to 24 carbon atoms, where spacer groups in which Y is —O—(CH$_2$)$_n$—, where n=0 to 4, is —O—(C$_6$H$_4$)—, is —NH—C(CH$_3$)$_2$— or —NH—CH(CH$_2$CH$_3$)— are preferred.

In summary, dishwasher detergents according to the invention are preferred which comprise, as ingredient b), one or more copolymers which contain structural units of the formulae (TVII) and/or (TVIII) and/or (TIX) and/or (TX) and/or (TXI) and/or (TXII)

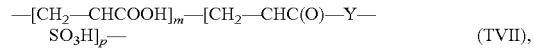  (TVII),

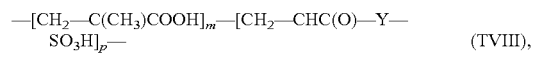  (TVIII),

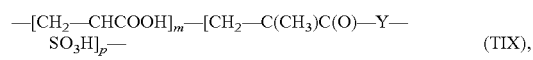  (TIX),

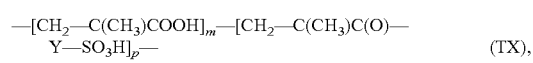  (TX),

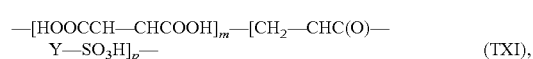  (TXI),

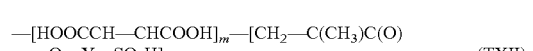  (TXII), in which m and p are in each case a whole natural number between 1 and 2000, and Y is a spacer group which is selected from substituted or unsubstituted aliphatic, aromatic or araliphatic hydrocarbon radicals having 1 to 24 carbon atoms, where spacer groups in which Y is —O—(CH$_2$)$_n$—, where n=0 to 4, is —O—(C$_6$H$_4$)—, is —NH—C(CH$_3$)$_2$— or ——NH—CH(CH$_2$CH$_3$)— are preferred.

In the polymers, all or some of the sulfonic acid groups can be present in neutralized form, i.e. the acidic hydrogen atom of the sulfonic acid group in some or all sulfonic acid groups can be replaced with metal ions, preferably alkali metal ions and in particular with sodium ions. Corresponding compositions which are characterized in that the sulfonic acid groups in the copolymer are in partially or completely neutralized form are preferred in accordance with the invention.

The monomer distribution of the copolymers used in the compositions according to the invention is, in the case of copolymers which comprise only monomers from groups i) and ii), preferably in each case 5 to 95% by weight of i) or ii), particularly preferably 50 to 90% by weight of monomer from group i) and 10 to 50% by weight of monomer from group ii), in each case based on the polymer.

In the case of terpolymers, particular preference is given to those which comprise 20 to 85% by weight of monomer from group i), 10 to 60% by weight of monomer from group ii), and 5 to 30% by weight of monomer from group iii).

The molar mass of the polymers used in the compositions according to the invention can be varied in order to match the properties of the polymers to the desired intended use. Preferred dishwasher detergents are characterized in that the copolymers have molar masses of from 2000 to 200 000 gmol$^{-1}$, preferably from 4000 to 25 000 gmol$^{-1}$ and in particular from 5000 to 15 000 gmol$^{-1}$.

The amount of one or more copolymers in the compositions according to the invention can vary depending on the intended use and desired product performance, preferred dishwasher detergents according to the invention being characterized in that the copolymer or copolymers is/are present in amounts of from 0.25 to 50% by weight, preferably from 0.5 to 35% by weight, particularly preferably from 0.75 to 20% by weight and in particular from 1 to 15% by weight.

As already mentioned above, in the compositions according to the invention particular preference is given both to using polyacrylates and also the above-described copolymers of unsaturated carboxylic acids, monomers containing sulfonic acid groups, and optionally further ionic or nonionogenic monomers. The polyacrylates have been described in detail above. Particular preference is given to combinations of the above-described copolymers containing sulfonic acid groups with polyacrylates of low molar mass, for example in the range between 1000 and 4000 daltons. Such polyacrylates are commercially available under the trade name Sokalan® PA15 and Sokalan® PA25 (BASF).

The compositions according to the invention can also be formulated as fabric softeners or laundry adjuvants. Depending on the desired intended use, further ingredients may be used. Softener compositions for rinse-cycle softening are described widely in the prior art. These compositions usually comprise, as active substance, a cationic quaternary ammonium compound which is dispersed in water. Depending on the content of active substance in the finished softener composition, the terms used are either dilute, ready-to-use products (active substance contents below 7% by weight) or so-called concentrates (active substance content above 7% by weight). Because of the smaller volume and the simultaneously reduced packaging and transportation costs, the textile softener concentrates have advantages from an ecological point of view and have penetrated the market to an increasing extent. Because of the incorporation of cationic compounds which have only low solubility in water, customary softener compositions are in the form of dispersions, have a milky-cloudy appearance and are not transparent. For reasons of product esthetics, it can, however, also be desirable to provide the consumer with transparent, clear softeners which are visually superior to the known products.

As textile-softening active substance, fabric softeners according to the invention preferably comprise cationic surfactants, which have already been described above in detail (formulae TXII, TXIII and TXIV). These compositions according to the invention particularly preferably comprise what are called ester quats. While there is a large number of possible compounds from this class of substance, according to the invention particular preference is given to using ester quats which can be prepared by reacting trialkanolamines with a mixture of fatty acids and dicarboxylic acids, optional subsequent alkoxylation of the reaction product and quaternization in a manner known per se, as is described in DE 195 39 846.

The ester quats prepared in this way are suitable in an excellent manner for producing portions according to the invention which can be used as fabric softeners. Since, depending on the choice of trialkanolamine, fatty acids and dicarboxylic acids, and the quaternizing agent, a large number of suitable products can be prepared and used in the compositions according to the invention, a description of the ester quats to be used preferably according to the invention via their preparation route is more precise than giving a general formula.

Said components which react with one another to give the ester quats to be used with preference can be used in varying quantitative ratios relative to one another. For the purposes of the present invention, preference is given to fabric softeners in which a reaction product of trialkanolamines with a mixture of fatty acids and dicarboxylic acids in the molar ratio 1:10 to 10:1, preferably 1:5 to 5:1, which has optionally been alkoxylated and then quaternized in a manner known per se, is present in amounts of from 2 to 60% by weight, preferably 3 to 35% by weight and in particular 5 to 30% by weight. Particular preference here is given to the use of triethanolamine, such that further preferred fabric softeners of the present invention comprise a reaction product of triethanolamine with a mixture of fatty acids and dicarboxylic acids in the molar ratio 1:10 to 10:1, preferably 1:5 to 5:1, which has optionally been alkoxylated and then quaternized in a manner known per se, in amounts of from 2 to 60% by weight, preferably 3 to 35% by weight and in particular 5 to 30% by weight.

Fatty acids which can be used in the reaction mixture for preparing the ester quats are all acids obtained from vegetable or animal oils and fats. Here, it is entirely possible that the fatty acid used in the reaction mixture is a fatty acid which is not solid at room temperature, i.e. is pasty to liquid.

The fatty acids may, irrespective of their state of aggregation, be saturated or mono- to polyunsaturated. It is of course possible to use not only "pure" fatty acids, but also the technical-grade fatty acid mixtures obtained during the cleavage of fats and oils, these mixtures in turn being clearly preferred from an economic point of view.

For example, in the reaction mixtures for the preparation of the ester quats for the clear aqueous fabric softeners according to the invention, it is possible, for example, to use individual species or mixtures of the following acids: caprylic acid, pelargonic acid, capric acid, lauric acid, myristic acid, palmitic acid, stearic acid, octadecan-12-ol acid, arachidic acid, behenic acid, lignoceric acid, cerotic acid, melissic acid, 10-undecanoic acid, petroselic acid, petroselaidic acid, oleic acid, elaidic acid, ricinoleic acid, linolaidic acid, α- and β-eleosteric acid, gadoleic acid, erucic acid, brassidic acid. It is of course also possible to use the fatty acids with an odd number of carbon atoms, for example undecanoic acid, tridecanoic acid, pentadecanoic acid, heptadecanoic acid, nonadecanoic acid, heneicosanoic acid, tricosanoic acid, pentacosanoic acid, heptacosanoic acid.

For the purposes of the present invention, the use of fatty acids of the formula XIII in the reaction mixture for the preparation of the ester quats is preferred, so that preferred fabric softeners comprise a reaction product of trialkanolamines with a mixture of fatty acids of the formula TXIII,

$$R^1—CO—OH \quad (TXIII)$$

in which R1-CO— is an aliphatic, linear or branched acyl radical having 6 to 22 carbon atoms and 0 and/or 1, 2 or 3 double bonds, and dicarboxylic acids in the molar ratio 1:10 to 10:1, preferably 1:5 to 5:1, which has optionally been alkoxylated and then quaternized in a manner known per se, in amounts of from 2 to 60% by weight, preferably 3 to 35% by weight and in particular 5 to 30% by weight in the compositions.

Suitable dicarboxylic acids which are suitable for the preparation of the ester quats to be used in the compositions according to the invention are primarily saturated or mono- or polyunsaturated α,ω-dicarboxylic acids. By way of example, mention may be made here of the saturated species oxalic acid, malonic acid, succinic acid, glutaric acid, adipic acid, pimelic acid, suberic acid, azelaic acid, sebacic acid, undecanoic and dodecanoic acid, brassylic acid, tetra- and pentadecanoic acid, thapsic acid, and hepta-, octa- and nonadecanoic acid, eicosanoic and heneicosanoic acid, and phellogenic acid. In the reaction mixture, preference is given to using dicarboxylic acids which follow the general formula XIII, so that compositions according to the invention are preferred which comprise a reaction product of trialkanolamines with a mixture of fatty acids and dicarboxylic acids of the formula TXIV,

$$HO—OC—[X]—CO—OH \quad (TXIV)$$

in which X is an optionally hydroxy-substituted alkylene group having 1 to 10 carbon atoms, in the molar ratio 1:10 to 10:1, preferably 1:5 to 5:1, which has optionally been alkoxylated and then quaternized in a manner known per se, in amounts of from 2 to 60% by weight, preferably 3 to 35% by weight and in particular 5 to 30% by weight, in the compositions.

Among the large number of ester quats which can be prepared and used according to the invention, those in which the alkanolamine is triethanolamine and the dicarboxylic acid is adipic acid have in turn proven particularly useful. Thus, for the purposes of the present invention, particular preference is given to compositions which comprise a reaction product of triethanolamine with a mixture of fatty acids and adipic acid in the molar ratio 1:5 to 5:1, preferably 1:3 to 3:1, which has then been quaternized in a manner known per se, in amounts of from 2 to 60% by weight, preferably 3 to 35% by weight and in particular 5 to 30% by weight, in the compositions.

The compositions according to the invention can—irrespective of whether they are formulated as textile detergents, washing auxiliaries or fabric softeners—also be equipped with further additional utilities. In this respect, it is possible, for example, to formulate dye-transfer-inhibiting compositions, products with "anti-gray formula", products which impart easier iron properties, products with a particular fragrance release, products with improved soil dissolution and prevention of resoiling, antibacterial products, UV protectants, color-freshening products etc. A few examples are described below:

Since fabrics, in particular those made of rayon, viscose, cotton and mixtures thereof, can tend to crease because the individual fibers are sensitive to bending, kinking, pressing, and squashing transversely to the direction of the fibers, the compositions according to the invention can comprise synthetic anticrease agents. These include, for example, synthetic products based on fatty acids, fatty acid esters, fatty acid amides, fatty acid alkylol esters, fatty acid alkylolamides or fatty alcohols, which are mostly reacted with ethylene oxide, or products based on lecithin or modified phosphoric esters.

To control microorganisms, the compositions according to the invention can comprise antimicrobial active ingredients. A distinction is drawn here, depending on the antimicrobial spectrum and activity mechanism, between bacteriostats and bactericides, fungistats and fungicides etc. Important substances from these groups are, for example, benzalkonium chlorides, alkylarylsulfonates, halophenols and phenol mercuriacetate, it also being possible to dispense entirely with these compounds in the case of the compositions according to the invention.

In order to prevent undesired changes to the compositions and/or the treated textiles caused by the effect of oxygen and other oxidative processes, the compositions can comprise antioxidants. This class of compound includes, for example, substituted phenols, hydroquinones, pyrocatechols and aromatic amines, and also organic sulfides, polysulfides, dithiocarbamates, phosphites and phosphonates.

Increased wear comfort can result from the additional use of antistats which are additionally added to the compositions according to the invention. Antistats increase the surface conductivity and thus permit an improved dissipation of the charges formed. External antistats are usually substances with at least one hydrophilic molecular ligand and produce a more or less hygroscopic film on the surfaces. These mostly surface-active antistats can be subdivided into nitrogen-containing antistats (amines, amides, quaternary ammonium compounds), phosphorus-containing antistats (phosphoric esters) and sulfur-containing antistats (alkylsulfonates, alkyl sulfates). Lauryl- (or stearyl-)dimethylbenzylammonium chlorides are suitable as antistats for textiles or as additives for detergents, in which case a softening effect is additionally achieved.

To improve the water-absorption capacity, the rewettability of the treated textiles and to make ironing of the treated textiles easier, silicone derivatives, for example, can be used in the compositions according to the invention. These additionally improve the rinse-out behavior of the compositions according to the invention by virtue of their foam-inhibiting properties. Preferred silicone derivatives are, for example, polydialkyl- or alkylarylsiloxanes in which the alkyl groups have one to five carbon atoms and are completely or partially fluorinated. Preferred silicones are polydimethylsiloxanes which can optionally be derivatized and then are amino-functional or quaternized, or have Si—OH, Si—H and/or Si—Cl bonds. The viscosities of the preferred silicones are, at 25° C., in the range between 100 and 100 000 centistokes, it being possible to use the silicones in amounts between 0.2 and 5% by weight, based on the total composition.

Finally, the compositions according to the invention can also comprise UV absorbers, which attach to the treated textiles and improve the photostability of the fibers. Compounds which have these desired properties are, for example, the compounds and derivatives of benzophenone having substituents in the 2- and/or 4-position which are effective as a result of nonradiative deactivation. Furthermore, substituted benzotriazoles, acrylates phenyl-substituted in the 3-position (cinnamic acid derivatives), optionally with cyano groups in the 2-position, salicylates, organic Ni complexes, and natural substances such as umbelliferone and endogenous urocanic acid are also suitable.

Further additives which can be conceived and which are preferred in specific embodiments are surfactants, which may influence in particular the solubility of the water-soluble walls of the flexible, preferably elastic, hollow body or of the compartmentalization apparatus, but may also control the wettability thereof and the formation of foam during dissolution, and also foam inhibitors, and also bitter substances, which may prevent unintended swallowing of such hollow bodies or parts of such hollow bodies by children.

Fragrances are added to the detergents, cleaning products and/or care products of the invention in order to enhance the overall esthetic appeal of the products and to provide the user not only with the technical performance (fabric softening result) but also with a product which is sensorially typical and unmistakable. As perfume oils or fragrances it is possible to use individual odorant compounds, examples being the synthetic products of the ester, ether, aldehyde, ketone, alcohol and hydrocarbon types. Odorant compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethyl methylphenylglycinate, allyl cyclohexylpropionate, styrallyl propionate and benzyl salicylate. The ethers include, for example, benzyl ethyl ether. The aldehydes include, for example, linear alkanals having 8 to 18 carbon atoms, citral, citronellal, citronellyloxyacetaldehyde, cyclamen aldehyde, hydroxycitronellal, lileal and bourgeonal.

The ketones include the ionones, α-isomethylionone and methyl cedryl ketone. The alcohols include anethole, citronellol, eugenol, geraniol, linalool, phenylethyl alcohol and terpineol. The hydrocarbons include primarily terpenes such as limonene and pinene. Preference is giving to using mixtures of different odorants, which are matched to one another so that together they produce an appealing fragrance note. Such perfume oils may also contain natural odorant mixtures, such as are obtainable from plant sources. Examples are pine oil, citrus oil, jasmine oil, patchouli oil, rose oil or ylang-ylang oil. Likewise suitable are nutmeg oil, sage oil, camomile oil, clove oil, balm oil, mint oil, cinnamon leaf oil, lime blossom oil, juniperberry oil, vetiver oil, olibanum oil, galbanum oil and labdanum oil and also orange blossom oil, neroliol, orange peel oil and sandalwood oil.

The amount of fragrances is usually in the range up to 2% by weight of the overall detergent, cleaning product or care product portion.

The fragrances can be incorporated directly into the detersive, cleaning or care formulation(s); it may, however, also be advantageous to apply the fragrances to carriers which enhance the adhesion of the perfume to the laundry and, as a result of a slower fragrance release, ensure long-lasting fragrance of textiles. Cyclodextrins, for example, have been found suitable as such carrier materials. The cyclodextrin-perfume complexes may in that case additionally be coated with further auxiliaries.

The support-fixed bleaching catalysts can be used in accordance with the invention for bleaching colors, particularly hair colors and/or color stains on hard and/or soft surfaces, preferably for the bleaching of colored stains in connection with the laundering of textiles.

The support-fixed bleaching catalysts can be used in liquid, solid and/or gel-form compositions, particularly cleaning products, preferably for the bleaching of hard surfaces, such as tableware, and/or for the bleaching of colored stains on or in surfaces.

The support-fixed bleaching catalyst of the invention, particularly the compositions of the invention comprising the support-fixed bleaching catalyst, can be introduced into a metering compartment, preferably the rinse aid compartment or washing machine rinse drawer. The compositions comprising support-fixed bleaching catalyst(s) can be present in liquid, solid and/or gel form, which may also be in portion form, i.e., already separately preportioned for the customary use amount.

It can be particularly preferable to configure the form of the support-fixed bleaching catalysts in such a way that they can easily be re-used.

In that case particularly suitable supports are shaped articles, fabrics and/or particles on which the bleaching catalysts have been fixed. Preferably the particles can also be used in shaped articles or fabrics which a delivery of the Suitable, for example, are cloths on which the bleaching catalysts have been fixed, or suitable devices which comprising bleaching catalysts fixed to supports, in particular to particles. Such devices, e.g., pouches containing bleaching catalysts fixed to particles in the form, for example, of granules, can be added to the wash liquor, easily removed after the washing operation and so added again in the next operation. A prerequisite is that the devices are in a suitable form for the corresponding uses in accordance with the invention and the contact with liquids, particularly water (e.g., the wash liquor) and other solvents, develop their possibility of action, i.e., to enable the activation of peroxygen compounds.

The compositions of the invention can be used as detergents, cleaning products, care products and/or hair treatment compositions (in particular for coloring, preferably hair bleaching), building materials, cosmetics (for bleaching marks and/or discolorations, for example, particularly on teeth or the skin), adhesives, antibacterial compositions and/or disinfectants.

Depending on the intended use the compositions of the invention may comprise anionic surfactants, cationic surfactants, amphoteric surfactants, builder substances, bleaches, bleach activators, bleach stabilizers, further bleaching catalysts, enzymes, polymers, cobuilders, alkalizing agents, acidifying agents, antiredeposition agents, silver protectants, colorants, optical brighteners, UV stabilizers, fabric softeners, fragrances, soil repellents, anticrease substances, antibacterial substances, color protectants, discoloration inhibitors, vitamins, phyllosilicates, odor-complexing substances, rinse aids, foam inhibitors, foaming agents, preservatives and/or auxiliaries. In particular the ingredients already described earlier on above can be employed for these purposes.

EXAMPLES

Methods of Measuring the Stability of the Support-fixed Bleaching Catalysts which can be used in Accordance with the Invention 500 mg of support-fixed bleaching catalyst having a transition metal content of >200 mg/l were introduced into 1 L of water or 1 L of wash liquor (laundry detergent wash liquor Megaperls, Henkel company usual recommended user dose) with a water temperature of 40° C. for 1 hour; following removal of the support-fixed bleaching catalysts, the residual water content had transition metal residues of <0.02 mg/l, preferably of <0.01 mg/l and more preferably of <0.001 mg/l. (Detection limit <10 micrograms/L)

Examples 1 to 2 indicate processes for preparing ligands which can be used in accordance with the invention. Examples 3 to 4 indicate processes for preparing the bleaching catalyst(s) of the invention bound to supports via ligand(s).

Example 1

Preparation of ((6-methyl-2-pyridyl)methyl)bis(2-pyridylmethyl)amine(me$_1$tpa)

Process for Preparing bis(2-pyridylmethyl)amine 10.80 g (0.1 mol) of 2-methylpyridylamine were dissolved in 50 ml of methanol and 10.82 g (0.101 mol) of 2-pyridylcarboxaldehyde were added to the solution and the mixture was stirred at room temperature for two hours. Thereafter 1.9 g (0.050 mol) of sodium borohydride were added over the course of 15 minutes at 0° C. in an ice bath and following the end of gas evolution the solution was stirred at room temperature overnight. Half-concentrated HCl was added to the solution in order to destroy unreacted hydride and then the solution was extracted with five times 20 ml of chloroform. The combined organic phases were discarded and the aqueous phase was brought to a pH of 8 using dilute NaOH and extracted with five times 20 ml of chloroform. The combined organic phases were dried over MgSO$_4$, the solvent was separated off on a rotary evaporator and the residue was subjected to fractional distillation at 2.5 torr/165° C.

Process for Preparing ((6-methyl-2-pyridyl)methyl)bis(2-pyridylmethyl)amine (me$_1$tpa)

In a 250 ml three-necked flask 4.98 g (0.025 mol) of bis(2-pyridylmethyl)amine were dissolved in 100 ml of methanol and this solution was admixed with 3.33 g (0.0275 mol) of 6-methyl-2-pyridylaldehyde and 4.2 g (0.07 mol) of acetic acid. After cooling to 0° C. the solution was admixed with 1.38 g (0.022 mol) of sodium cyanoborohydride in suspension in 50 ml of methanol. The hydrogen cyanide formed was oxidized using alkaline KMnO$_4$ solution. After three days of stirring at room temperature, the solution was admixed with conc. HCl to destroy unreacted hydride. The methanol was separated off on a rotary evaporator and the residue was taken up in water and rendered alkaline using NaOH, the brown oil which separates off being extracted with five times 20 ml of chloroform. The combined organic phases were dried over MgSO$_4$ and the solvent was separated off on a rotary evaporator. The product was recrystallized from ligroin (b.p.: 80-110° C.).

Example 2

Preparation of ((6-chloromethyl-2-pyridyl)methyl)bis(2-pyridylmethyl)amine (Cl-me$_1$tpa)

In a 250 ml three-necked flask 1 equivalent of bis(2-pyridylmethyl)amine was dissolved in 100 ml of THF and the solution was admixed with 1 equivalent of 2,6-bis(chloromethyl)pyridine and 4 equivalents of N,N-diisopropylethylamide. The solution was stirred at room temperature for 7 days. The solution was filtered and the filtrate was purified by column chromatography.

Example 3

Fixing on Chloromethylated Polystyrene (Merrifield Resin (Chloromethylated Polystyrene))

Fixing of Dipodal Ligands (bis(2-pyridylmethyl)amine)

In a 250 ml three-necked flask 4 g (0.02 mol) of bis(2-pyridylmethyl)amine (bpa) were dissolved in 100 ml of acetonitrile and 10 g (approximately 0.01 mol Cl) of Merrifield resin (chloromethylated polystyrene) were suspended in said solution. The suspension was admixed with 100 mg (0.7 mol) of sodium iodide and heated under reflux for 48 hours. The Merrifield resin (chloromethylated polystyrene) was filtered off and washed with 25 ml of acetonitrile, 25 ml of a 10% strength aqueous 1:1 mixture of methanol and potassium carbonate, an aqueous 1:1 mixture of methanol and water, and 25 ml of methanol and ethanol. The resulting solid was dried under reduced pressure.

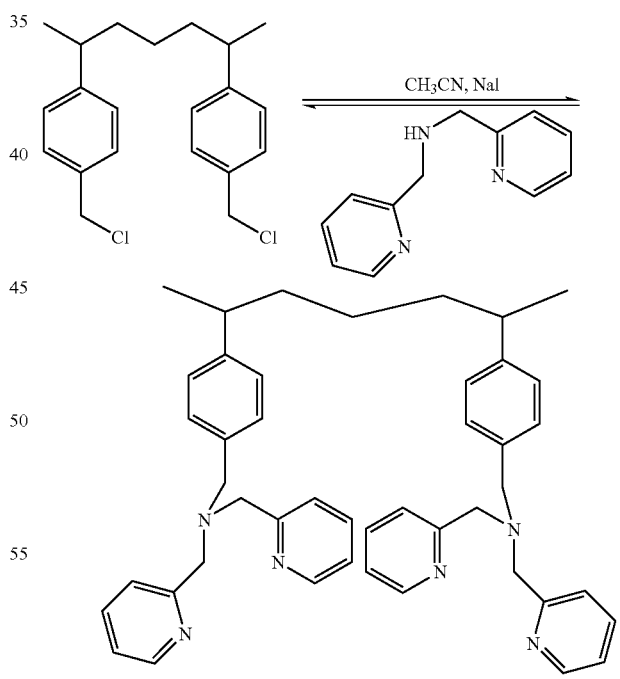

Example 4

Fixing of Tripodal Ligands

In a 250 ml three-necked flask 1 equivalent of ((6-chloromethyl-2-pyridyl)methyl)bis(2-pyridylmethyl)amine (Cl-me₁tpa) were dissolved in 100 ml of tetrahydrofuran under nitrogen and this solution was added to a suspension of 1 equivalent each of n-butyllithium (in solution in heptane) and Merrifield resin (chloromethylated polystyrene) and the mixture was stirred at room temperature overnight. The Merrifield resin (chloromethylated polystyrene) was filtered off and washed with 25 ml of acetonitrile, 25 ml of a 10% strength aqueous 1:1 mixture of methanol and potassium carbonate, an aqueous 1:1 mixture of methanol and water, and 25 ml of methanol and ethanol. The resulting solid was dried under reduced pressure.

to a suspension of 1 equivalent of Merrifield resin (chloromethylated polystyrene, Fluka) and the mixture was stirred at room temperature overnight. The Merrifield resin (chloromethylated polystyrene) was filtered off and washed with 25 ml of acetonitrile, 25 ml of a 10% strength aqueous 1:1 mixture of methanol and potassium carbonate, an aqueous 1:1 mixture of methanol and water, and 25 ml of methanol and ethanol. The resulting solid was dried under reduced pressure.

Example 6

Fixing of Macrocyclic Ligands

In a 50 ml flask 1 g (0.008 mol) of triazacyclononane (Fluka) and 1 g (0.008 mol) of N,N-dimethylformamide dimethylacetal (Fluka) are dissolved in tetrahydrofuran and the solution is stirred under reflux at 85° C. for 3 h. 1 g of Merrifield resin (chloromethylated polystyrene) is added to the solution and the suspension is stirred at room temperature for 1 h. The Merrifield resin (chloromethylated polystyrene) is filtered off and washed with 25 ml of acetonitrile, 25 ml of a 10% strength aqueous 1:1 mixture of methanol and potassium carbonate, an aqueous 1:1 mixture of methanol and water, and 25 ml of methanol and ethanol. The resulting solid is dried under reduced pressure.

Subsequently 25 equivalents of NaOH in ethanol are added to the resin and the mixture is stirred under reflux for 24 h. Finally the Merrifield resin (chloromethylated polystyrene) is filtered off and washed with 25 ml of acetonitrile, 25 ml of a 10% strength aqueous 1:1 mixture of methanol and potassium carbonate, an aqueous 1:1 mixture of methanol and water, and 25 ml of methanol and ethanol. The resulting solid is dried under reduced pressure.

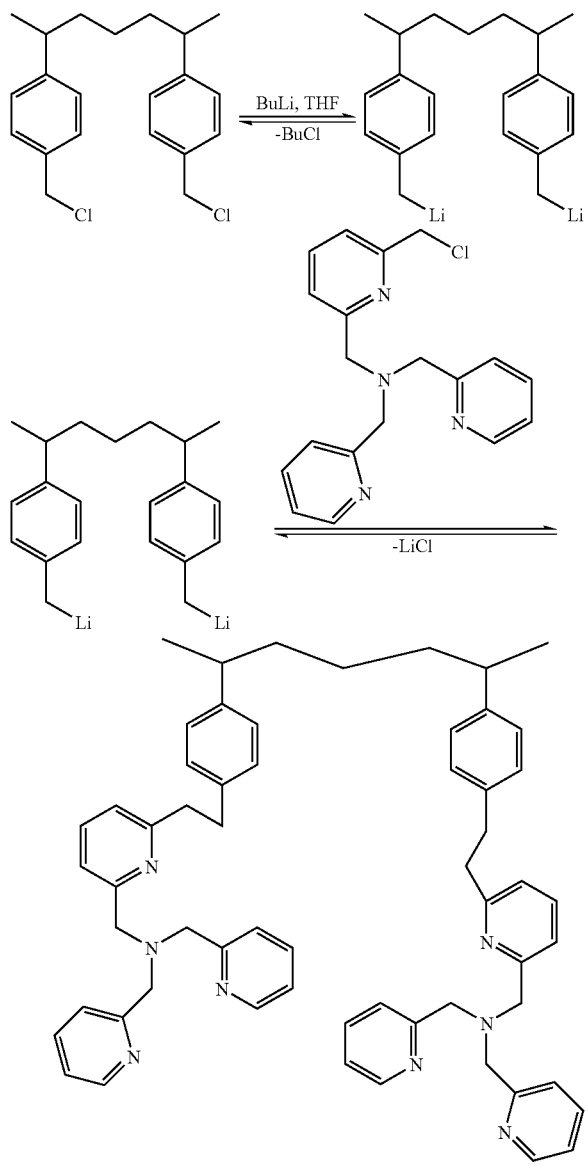

Example 5

Fixing of Tripodal Ligands

In a 250 ml three-necked flask 1 equivalent of the sodium alkoxide of ((6-hydroxymethyl-2-pyridyl)methyl)bis(2-pyridylmethyl)amine (HO-me₁tpa) were dissolved in 100 ml of tetrahydrofuran under nitrogen and this solution was added

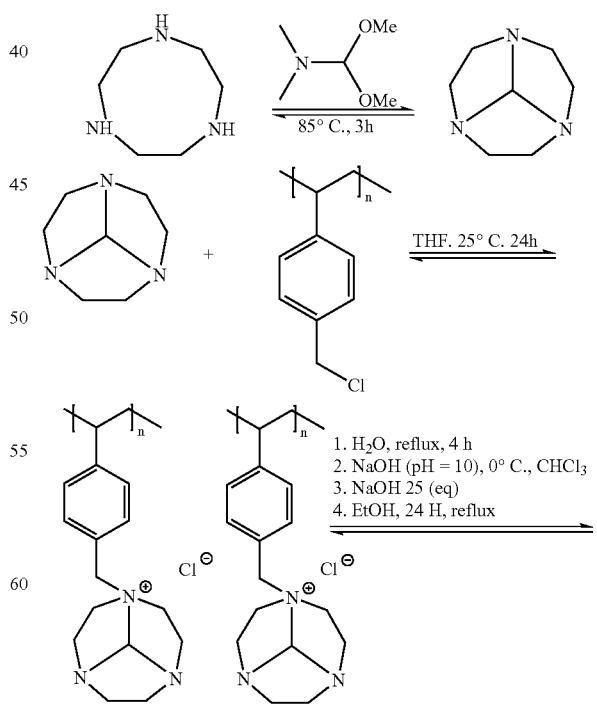

Fixing of the catalyst fix-TACN

-continued

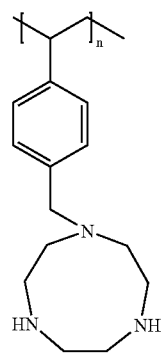

Example 7

Loading of the Fixed Ligands with Transition Metals

Ligands fixed on Merrifield resin (chloromethylated polystyrene) are suspended in 5 ml of acetonitrile and combined with an equimolar solution of $Mn(ClO_4)_2 \cdot 6H_2O$ of $Fe(ClO_4)_3$ or $Mn(OAc)_3$ (Fluka) in 5 ml of water and stirred for 10 minutes. The loaded Merrifield resin (chloromethylated polystyrene) is subsequently dried under reduced pressure.

Example 8

Investigation for Bleaching Activity (Morin Test)

In order to test different fixed complexes for their bleaching behavior the course of the extinction of a morin solution at 400 nm is observed over time. For these spectroscopic investigations an aqueous morin solution [5 mg morin/l, Fluka] was placed in a flow-through cuvette and the morin solution in the reaction vessel was admixed at a constant pH of 9.5 (by means of a pH-stat instrument or buffer) with 980 mg/l perborate monohydrate (Fluka), corresponding to the amount of 4.9 g/l in a standard laundry detergent formulation. The catalysts under test were insoluble. Two minutes after the start of the instrument the "beads" with the substances under test are added, so that in the reaction vessel the complexed transition metal is then present with a concentration of 0.25 mg/l. Passage of the products into the flow-through cuvette was prevented by means of a filter.

Results with Dipodal Ligand Systems

Fixed ligand prepared according to Example 3 and loading according to Example 7.
Table 1 shows maximum decoloring results.

TABLE 1

| Loading with ligand | Transition metal | Max. decoloring |
|---|---|---|
| Merrifield 1.5 mmol/bpa | $Fe^{3+}$ | 5% |
| Merrifield 2.5 mmol/bpa | $Mn^{2+}$ | 30% |
| Merrifield 2.5 mmol/bpa | $Mn^{3/4+}$ | 40% |
| Merrifield 1 mmol/bpa | $Mn^{2+}$ | 30% |
| Merrifield 5.5 mmol/bpa | $Mn^{2+}$ | 38% |
| Merrifield 2.5 mmol/bpa | $Mn^{3/4+}$ | 25% |
| Merrifield 5.5 mmol/bpa | $Mn^{3/4+}$ | 17% |
| Perborate | | 14% |

Results with Macrocyclic Ligand Systems

Fixed ligand prepared according to Example 6 and loading according to Example 7.

TABLE 2

| | Decoloring by Mn-tacn in [%] | |
|---|---|---|
| Time [min] | (Fixed) | (Dissolved) |
| 0 | 0 | 0 |
| 5 | 60 | 60 |
| 10 | 83 | 88 |
| 15 | 89 | 94 |
| 20 | 90 | 84 |
| 25 | 91 | 84 |
| 30 | 92 | 99 |

Fixed or heterogeneous catalyst systems show in some cases very high activities—even in comparison with homogeneous catalysts or perborate—in the catalytic decoloring or catalytic bleaching of morin (Table 2).

Example 9

Multiple Utilization of the Fixed Catalysts

To test various fixed complexes in respect of multiple utilization the course of the extinction of a morin solution at 400 nm over time is observed over 3 times 30 minutes. The ligand system used was a macrocyclic ligand system loaded with $Mn^{3+/4+}$; further detailes as described in Example 8. After each test the catalyst is isolated by filtration, dried and then used again. Table 3 shows multiple utilization data.

TABLE 3

| Time [min] | Decoloring 1st test | Decoloring 2nd test | Decoloring 3rd test | Perborate |
|---|---|---|---|---|
| 0 | 0 | 0 | 0 | 0 |
| 5 | 78 | 46 | 44 | 3 |
| 10 | 90 | 71 | 58 | 5 |
| 15 | 90 | 82 | 71 | 7 |
| 20 | 94 | 88 | 75 | 8 |
| 25 | 94 | 91 | 78 | 10 |
| 30 | 95 | 92 | 85 | 10 |

In the case of the third test decoloring of 85% was achieved with the same material, despite slight losses in recovery (Table 3). Multiple utilization is therefore conceivable even without renewed loading with transition metal.

Example 10

Washing Experiments/Detection of Transition Metals in the Washing Water

For the bleaching catalysts according to Examples 3 and 7 the manganese content emitted to the wash liquor was measured 500 mg/L of polymer-fixed catalysts were added to a wash liquor containing 980 mg/l perborate monohydrate, corresponding to 4.9 g/L laundry detergent formulation or commercial laundry detergent without transition metal bleaching catalysts (Persil color and Persil megaperls, Henkel KGaA) with the predefined dose. The manganese content (mg Mn/L) was determined by atomic absorption spectroscopy from samples after a 90-minute washing cycle at 60° C. without laundry in a laboratory launderometer (triple determination; Table 4 specifies the maximum values).

Table 4 shows concentration of transition metals in washing water.

TABLE 4

| Solution with Persil megaperls + catalysts | Time | |
|---|---|---|
| mg Mn/l | t = 0 | t = 90 min |
| | <0.05 | <0.05 |
| | 0.06 | 0.12 |
| | 0.07 | 0.12 |

Virtually no manganese was detectable in the washing water even after 90 minutes. Textile damage due to the attachment of the transition metal to the textiles can therefore be ruled out.

The disclosures of each patent, patent application, and publication cited or described in this document are hereby incorporated herein by reference, in their entireties.

Various modifications of the invention, in addition to those described herein, will be apparent to those skilled in the art from the foregoing description. Such modifications are also intended to fall within the scope of the appended claims.

What is claimed is:

1. A composition comprising:
   a bleaching catalyst covalently bonded to a support selected from the group consisting of polyvinyl chloride, polybutadiene, polychlorobutadiene, polyvinylidene chloride, polyacrylonitrile, polydichloromethyloxaisobutane, polyurethane, polystyrenes, polymethacrylates, polyvinyl alcohols, polyethylenimines, cellulose, chitosan, polyamides, polyamines, polyformaldehydes, polyethylene, polypropylene, polytetrafluoroethylene, polyisobutylene, polydimethylphenylene oxide, and polyisocyanates,
   wherein
      the support contains one or more organic ligands covalently bonded to the support via at least one nitrogen atom,
      the covalent bonds of the support, organic ligand, and bleaching catalyst are not cleaved in the presence of aqueous acid or base containing solutions, and
      wherein at least one organic ligand is a triazacyclononane ligand covalently bonded to the support via at least one nitrogen atom.

2. The composition of claim 1, further comprising at least one transition metal to form a bleaching catalyst complex.

3. The composition of claim 2, wherein the transition metal is in oxidation state +2, +3 or +4.

4. The composition of claim 2, wherein the transition metal is at least one of iron or manganese.

5. The composition of claim 1, wherein at least one organic ligand is a transition-metal-free ligand for scavenging transition metals.

6. The composition of claim 1, wherein at least one organic ligand is a monopodal, dipodal, tripodal, tetrapodal, pentapodal or hexapodal ligand.

7. The composition of claim 1, wherein at least one organic ligand is selected from the group consisting of bis(2-pyridylmethyl)amine, (2-pyridylmethyl)(2-(2-pyridyl)ethyl)amine, (2-pyridylmethyl)(3-(N,N-dimethylamino)propyl)amine, (2-pyridylmethyl)(2-(N,N-dimethylamino)ethyl)amine, (2-pyridylmethyl)(2-hydroxyethyl)amine, (2-pyridylmethyl)(3-hydroxypropyl)amine, (2-pyridylmethyl)(2-N-morpholinoethyl)amine, (2-pyridylmethyl)(2-N-piperidinoethyl)amine, (2-pyridylmethyl)(2-N-pyrrolidinoethyl)amine, (2-pyridylmethyl)(2-N-piperazinoethyl)amine, (2-hydroxybenzyl)(2-pyridylmethyl)amine, (2-hydroxybenzyl)(2-(2-pyridyl)ethyl)amine, (2-hydroxybenzyl)(3-(N,N-dimethylamino)propyl)amine, (2-hydroxybenzyl)2-(N,N-dimethylaminoethyl)amine, (2-hydroxybenzyl)(2-hydroxyethyl)amine, (2-hydroxybenzyl)(3-hydroxypropyl)amine, (2-hydroxybenzyl)(2-N-morpholinoethyl)amine, (2 hydroxybenzyl)(2-N-piperidinoethyl)amine, (2 hydroxybenzyl)(2-N-pyrrolidinoethyl)amine, (2 hydroxybenzyl)(2-N-piperazinoethyl)amine, ((6 methyl-2-pyridyl)methyl)bis(2-pyridylmethyl)amine, bis((6-methyl-2-pyridyl)methyl)(2-pyridylmethyl)amine, tris((6-methyl-2-pyridyl)methyl)amine, [(benzimidazol-2-yl)methyl][(6-methyl-2-pyridyl)methyl)(2-pyridyl)methyl]amine, bis[(benzimidazol-2-yl)methyl][(6-methyl-2-pyridyl)methyl)]amine, [(5,6-dimethylbenzimidazol-2-yl)methyl][(6-methyl-2-pyridyl)methyl)(2-pyridyl)methyl]amine, bis[(5,6-dimethylbenzimidazol-2-yl)methyl][(6-methyl-2-pyridyl)methyl)]amine, [(2-pyridyl)methyl(6-methyl-2-pyridyl)(2-quinolyl)methyl]amine, bis[(2-quinolyl)(6-methyl-2-pyridyl)methyl]amine, [(2-pyridyl)methyl](2-N-morpholinoethyl)][(6-methyl-2-pyridyl)methyl]amine, [(2-pyridyl)methyl](2-N-piperidinoethyl)][(6-methyl-2-pyridyl)methyl]amine, [2-(2-pyridyl)ethyl][(2-pyridyl)methyl])][(6-methyl-2-pyridyl)methyl]amine, [(2-pyridyl)methyl][2-(2-pyridyl)ethyl])][(6-methyl-2-pyridyl)methyl]amine, N,N,N',N'-tetrakis[2-benzimidazolylmethyl]-1,3-diamino-2-propanol, N,N,N',N'-tetrakis[2-(5,6-dimethyl)benzimidazolylmethyl]-1,3-diamino-2-propanol, N,N,N',N'-tetrakis[2-(2-hydroxyethyl)benzimidazolylmethyl]-1,3-diamino-2-propanol, and N,N,N',N'-tetrakis[2-(1-methyl)imidazolylmethyl]-1,3-diamino-2-propanol.

8. The composition of claim 1, wherein at least one organic ligand is selected from the group consisting of ligands containing pyridin-2-yl, ligands containing 2-aminoethyl, N-methyl-N,N',N'-tris(3-methylpyridin-2-ylmethyl)ethylene-1,2-diamine, and N-ethyl-N,N',N'-tris(3-methylpyridin-2-ylmethyl)ethylene-1,2-diamine.

9. The composition of claim 1, wherein the support is a polymer containing at least one functional group or substituent suitable for forming a covalent bond.

10. The composition of claim 9, wherein the polymer is chloromethylated polystyrene.

11. The composition of claim 1, wherein the support is a shaped article.

12. The composition of claim 1, wherein the support is at least one of a powder, a particle, an agglomerate, or a fiber.

13. The composition of claim 1, wherein the support is a particle having a particle diameter in a range from 20 μm and 1 mm.

14. The composition of claim 12, wherein the support is a cloth comprising the at least one fiber.

15. The composition of claim 1, wherein the composition activates at least one of peroxygen compounds or oxygen.

16. The composition of claim 1, wherein the composition activates at least one of organic peracids, hydrogen peroxide, perborate, or percarbonate.

17. The composition of claim 1, wherein the composition can be regenerated at a pH of between 7 and 14.

18. A bleach comprising the composition of claim 1.

19. A cleaning product comprising the composition of claim 1.

20. A detergent comprising the composition of claim 1 and at least one of anionic surfactants, cationic surfactants, amphoteric surfactants, builder substances, bleaches, bleach activators, bleach stabilizers, bleaching catalysts, enzymes, polymers, cobuilders, alkalizing agents, acidifying agents, antiredeposition agents, silver protectants, colorants, optical brighteners, UV stabilizers, fabric softeners, fragrances, soil repellents, anticrease substances, antibacterial substances, color protectants, discoloration inhibitors, vitamins, phyllosilicates, odor-complexing substances, rinse aids, foam inhibitors, foaming agents, preservatives, or auxiliaries.

21. A hair treatment comprising the composition of claim 1.

22. A cosmetic comprising the composition of claim 1.

23. A composition comprising:
  a bleaching catalyst covalently bonded to a polymeric support,
wherein
  the polymeric support contains at least one organic ligand selected from the group consisting of:
    bis(2-pyridylmethyl)amine, (2-pyridylmethyl)(2-(2-pyridyl)ethyl)amine, (2-pyridylmethyl)(3-(N,N-dimethylamino)propyl)amine, (2-pyridylmethyl)(2-(N,N-dimethylamino)ethyl)amine, (2-pyridylmethyl)(2-hydroxyethyl)amine, (2-pyridylmethyl)(3-hydroxypropyl)amine, (2-pyridylmethyl)(2-N-morpholinoethyl)amine, (2-pyridylmethyl)(2-N-piperidinoethyl)amine, (2-pyridylmethyl)(2-N-pyrrolidinoethyl)amine, (2-pyridylmethyl)(2-N-piperazinoethyl)amine, (2-hydroxybenzyl)(2-pyridylmethyl)amine, (2-hydroxybenzyl)(2-(2-pyridyl)ethyl)amine, (2-hydroxybenzyl)(3-(N,N-dimethylamino)propyl)amine, (2-hydroxybenzyl)2-(N,N-dimethylaminoethyl)amine, (2-hydroxybenzyl)(2-hydroxyethyl)amine, (2-hydroxybenzyl)(3-hydroxypropyl)amine, (2-hydroxybenzyl)(2-N-morpholinoethyl)amine, (2 hydroxybenzyl)(2-N-piperidinoethyl)amine, (2 hydroxybenzyl)(2-N-pyrrolidinoethyl)amine, (2 hydroxybenzyl)(2-N-piperazinoethyl)amine, ((6 methyl-2-pyridyl)methyl)bis(2-pyridylmethyl) amine, bis((6-methyl-2-pyridyl)methyl)(2-pyridylmethyl)amine, tris((6-methyl-2-pyridyl)methyl)amine, [(benzimidazol-2-yl)methyl][(6-methyl-2-pyridyl)methyl)(2-pyridyl)methyl]amine, bis[(benzimidazol-2-yl)methyl][(6-methyl-2-pyridyl)methyl)] amine, [(5,6-dimethylbenzimidazol-2-yl)methyl][(6-methyl-2-pyridyl)methyl)(2-pyridyl)methyl]amine, bis[(5,6-dimethylbenzimidazol-2-yl)methyl][(6-methyl-2-pyridyl)methyl)]amine, [(2-pyridyl)methyl(6-methyl-2-pyridyl)(2-quinolyl)methyl]amine, bis[(2-quinolyl)(6-methyl-2-pyridyl)methyl]amine, [(2-pyridyl)methyl](2-N-morpholinoethyl)][(6-methyl-2-pyridyl)methyl]amine, [(2-pyridyl)methyl](2-N-piperidinoethyl)][(6-methyl-2-pyridyl)methyl] amine, pmap[2-(2-pyridyl)ethyl][(2-pyridyl)methyl])][(6-methyl-2-pyridyl)methyl]amine, pmea [(2-pyridyl)methyl][2-(2-pyridyl)ethyl])][(6-methyl-2-pyridyl)methyl]amine, N,N,N',N'-tetrakis[2-benzimidazolylmethyl]-1,3-diamino-2-propanol, N,N,N',N'-tetrakis[2-(5,6-dimethyl)benzimidazolylmethyl]-1,3-diamino-2-propanol, N,N,N',N'-tetrakis[2-(2-hydroxyethyl)benzimidazolylmethyl]-1,3-diamino-2-propanol, and N,N,N',N'-tetrakis[2-(1-methyl)imidazolylmethyl]-1,3-diamino-2-propanol,
    covalently bonded to the support via at least one nitrogen atom,
  the polymeric support further contains at least one triazacyclononane ligand covalently bonded to the support via at least one nitrogen atom, and
  the covalent bonds of the support, organic ligand, or bleaching catalyst are not cleaved in the presence of aqueous acid or base containing solutions.

24. The composition of claim 1 wherein the support comprises polystyrene.

25. A detergent comprising the composition of claim 23 and at least one of anionic surfactants, cationic surfactants, amphoteric surfactants, builder substances, bleaches, bleach activators, bleach stabilizers, bleaching catalysts, enzymes, polymers, cobuilders, alkalizing agents, acidifying agents, antiredeposition agents, silver protectants, colorants, optical brighteners, UV stabilizers, fabric softeners, fragrances, soil repellents, anticrease substances, antibacterial substances, color protectants, discoloration inhibitors, vitamins, phyllosilicates, odor-complexing substances, rinse aids, foam inhibitors, foaming agents, preservatives, or auxiliaries.

26. A detergent comprising the composition of claim 1 and at least one of anionic surfactants, cationic surfactants, amphoteric surfactants, builder substances, bleaches, bleach activators, bleach stabilizers, bleaching catalysts, enzymes, polymers, cobuilders, alkalizing agents, acidifying agents, antiredeposition agents, silver protectants, colorants, optical brighteners, UV stabilizers, fabric softeners, fragrances, soil repellents, anticrease substances, antibacterial substances, color protectants, discoloration inhibitors, vitamins, phyllosilicates, odor-complexing substances, rinse aids, foam inhibitors, foaming agents, preservatives, or auxiliaries.

27. A method for the bleaching of a color stain during textile laundering comprising contacting oxygen or a peroxygen compound in the wash liquors during laundering with the composition of claim 1 for a time and under conditions effective to substantially reduce the color stain.

28. A method for the bleaching of a color stain during textile laundering comprising contacting oxygen or a peroxygen compound in the wash liquors during laundering with the composition of claim 23 for a time and under conditions effective to substantially reduce the color stain.

29. A method for the bleaching of a color stain during textile laundering comprising contacting oxygen or a peroxygen compound in the wash liquors during laundering with the composition of claim 1 for a time and under conditions effective to substantially reduce the color stain.

* * * * *